(12) United States Patent
Singh et al.

(10) Patent No.: US 6,759,538 B2
(45) Date of Patent: Jul. 6, 2004

(54) SUBSTITUTED DIPHENYL HETEROCYCLES USEFUL FOR TREATING HCV INFECTION

(75) Inventors: Rajinder Singh, Walnut Creek, CA (US); Dane Goff, Redwood, CA (US); Henry Lu, Foster City, CA (US); Sarkiz D. Issankani, San Jose, CA (US); Thomas Sun, Fremont, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 10/286,017

(22) Filed: Nov. 1, 2002

(65) Prior Publication Data

US 2003/0165561 A1 Sep. 4, 2003

Related U.S. Application Data

(60) Provisional application No. 60/350,107, filed on Nov. 2, 2001, and provisional application No. 60/405,472, filed on Aug. 23, 2002.

(51) Int. Cl.$^7$ .................. A61P 43/00; A61K 31/415; C07D 207/02
(52) U.S. Cl. .................. 548/240; 514/400; 514/406; 548/267.6; 548/375.1; 548/338.1
(58) Field of Search ................ 514/383, 400, 514/406; 548/267.6, 375.1, 338.1

(56) References Cited

U.S. PATENT DOCUMENTS

| 4,752,324 | A | 6/1988 | Thomas et al. |
| 5,151,441 | A | 9/1992 | Mueller et al. |
| 5,256,666 | A | 10/1993 | Mueller et al. |
| 5,463,071 | A | 10/1995 | Himmelsbach et al. |
| 5,814,627 | A | 9/1998 | Schwab et al. |
| 6,355,669 | B1 | 3/2002 | Yamauchi et al. |
| 2002/0035156 | A1 | 3/2002 | Roniker et al. |
| 2002/0049213 | A1 | 4/2002 | Weidner-Wells et al. |

FOREIGN PATENT DOCUMENTS

| EP | 563 686 A1 | 3/1993 |
| EP | 92/7992 A1 | 7/1999 |
| JP | 04124178 A | 4/1992 |
| WO | WO 93/17671 | 9/1993 |
| WO | WO 94/17059 | 6/1994 |
| WO | WO 95/24397 | 9/1995 |
| WO | WO 98/47509 | 10/1998 |
| WO | WO 99/04390 | 1/1999 |
| WO | WO 99/20309 | 4/1999 |
| WO | WO 00/45799 | 8/2000 |
| WO | WO 00/78726 A1 | 12/2000 |
| WO | WO 02/20436 A2 | 3/2002 |

OTHER PUBLICATIONS

Roth et al., "Zur Kondensation von Chalkonoxyden mit Hydroxylamin", Arch. Pharm. 294, 769–774 (1961).
Kazimierz Samula, "Oksymowanic Azachalkonow", Roczniki ChemII, Ann. Soc. Chim. Polonorum 45, 2063 (1971).
Kazimierz Samula, "Cyclization of Azachalcones and β–Hydroxyketones Oximes", Roczniki ChemII. Ann. Soc. Chim. Polonorum 48, 959–964 (1974).
Robert K. Howe et al., "Nitrile Oxide Cycloaddition Routes to 2–(Isoxazolyl)–benzoates and 2–(1,2,4–Oxadiazol–3–yl)benzoates", Heterocycl. Chem. 19(4), 721–726 (1982).
Elena Belgodere et al., "Studies on Isomeric Pyridylisoxazoles", Heterocycles, 20(3), 501–504 (1983).
Sandor Batori et al., "Photoinduced Ring Transformation of Pyrido–[1,2–b]pyridazinium–4–olate", Tetrahedron, 50(16), 4699–4708 (1994).
Takaki Kanbara et al., "Preparation of Soluble and Fluorescent Poly(arylene)s by 1,3–Dipolar Polycycloaddition and Properties of the Polymers", Polymer Bulletin, 36, 673–679 (1996).
Yi–Yin Ku et al., "Use of Iodoacetylene as a Dipolarphile in the Synthesis of 5–Iodoisoxazole Derivatives", Organic Letters, 3(26), 4185–4187 (2001).
Maybridge, plc, Trevillett, Tintagel, Catalogue No. RF01972, Cornwall PL34 OHW, England.
Maybridge, plc, Trevillett, Tintagel, Catalog No. RF01996, Cornwall PL34 OHW, England.

*Primary Examiner*—Joseph K. McKane
*Assistant Examiner*—Andrea D. Small
(74) *Attorney, Agent, or Firm*—Dorsey & Whitney LLC; Scott D. Rothenberger; Ann M. Caviani Pease

(57) ABSTRACT

The present invention relates to substituted diphenyl heterocycle compounds and pharmaceutical compositions thereof that inhibit replication of HCV virus. The present invention also relates to the use of the compounds and/or compositions to inhibit HCV replication and/or proliferation and to treat or prevent HCV infections.

34 Claims, 16 Drawing Sheets

Method G

SUBSTITUTED DIPHENYL HETEROCYCLES USEFUL FOR TREATING HCV INFECTION

1. CROSS-REFERENCES TO RELATED APPLICATIONS

Figure 1A:
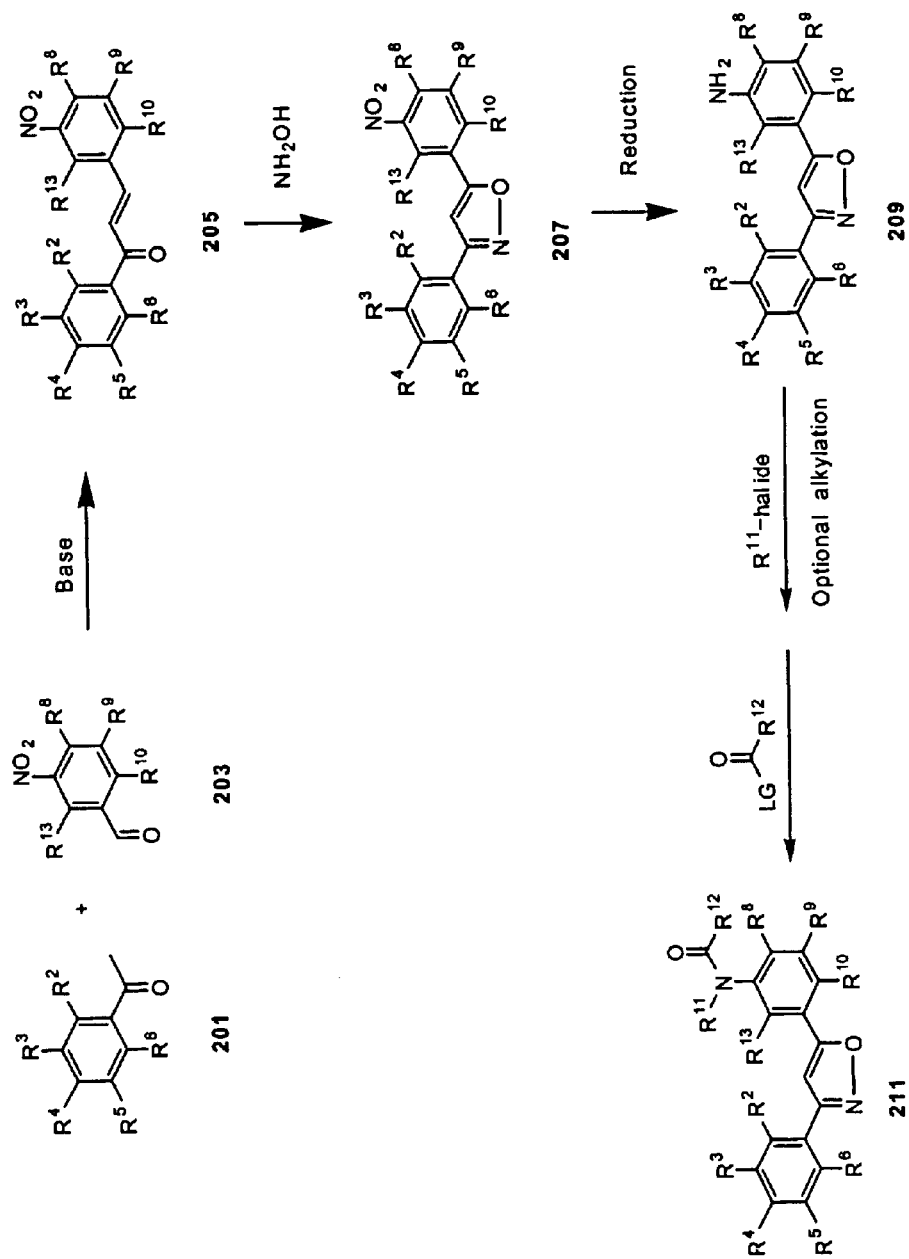

This application claims benefit under 35 U.S.C. §119(e) to U.S. Provisional Application Ser. No. 60/350,107, filed Nov. 2, 2001 and U.S. Provisional Application Ser. No. 60/405,472, filed Aug. 23, 2002.

2. FIELD OF INVENTION

The present invention relates to substituted diphenyl heterocycles and compositions thereof useful for treating or preventing Hepatitis C virus (HCV) infections. In particular, the present invention relates to substituted diphenyl isoxazole, pyrazole and oxadiazole compounds, compositions comprising the compounds and the use of such compounds and compositions to inhibit HCV replication and/or proliferation as a therapeutic approach towards the treatment and/or prevention of HCV infections in humans and animals.

3. BACKGROUND OF THE INVENTION

Hepatitis C virus (HCV) infection is a global human health problem with approximately 150,000 new reported cases each year in the United States alone. HCV is a single stranded RNA virus, which is the etiological agent identified in most cases of non-A, non-B post-transfusion and post-transplant hepatitis and is a common cause of acute sporadic hepatitis (Choo et al., Science 244:359, 1989; Kuo et al., Science 244:362, 1989; and Alter et al., in Current Perspective in Hepatology, p. 83, 1989). It is estimated that more than 50% of patients infected with HCV become chronically infected and 20% of those develop cirrhosis of the liver within 20 years (Davis et al., New Engl. J. Med. 321:1501, 1989; Alter et al., in Current Perspective in Hepatology, p. 83, 1989; Alter et al., New Engl. J. Med. 327:1899, 1992; and Dienstag Gastroenterology 85:430, 1983). Moreover, the only therapy available for treatment of HCV infection is interferon-α (INTRON® A, PEG-INTRON® A, Schering-Plough; ROFERON-A®, PEGASys®, Roche). Most patients are unresponsive, however, and among the responders, there is a high recurrence rate within 6–12 months after cessation of treatment (Liang et al., J. Med. Virol. 40:69, 1993). Ribavirin, a guanosine analog with broad spectrum activity against many RNA and DNA viruses, has been shown in clinical trials to be effective against chronic HCV infection when used in combination with interferon-α (see, e.g., Poynard et al., Lancet 352:1426–1432, 1998; Reichard et al., Lancet 351:83–87, 1998), and this combination therapy has been recently approved (REBETRON, Schering-Plough; see also Fried et al., 2002, N. Engl. J. Med. 347:975–982). However, the response rate is still at or below 50%. Therefore, additional compounds for treatment and prevention of HCV infection are needed.

4. SUMMARY OF THE INVENTION

In one aspect, the present invention provides substituted diphenyl heterocycles that are potent inhibitors of Hepatitis C virus ("HCV") replication and/or proliferation. In one embodiment, the compounds are substituted diphenyl isoxazole, pyrazole and/or oxadiazole compounds according to structural formula (I):

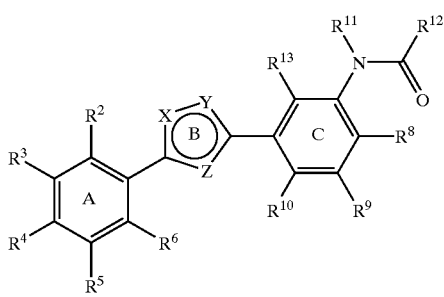

where Z is CH (isoxazoles, or pyrazoles) or N (oxadiazoles) and X and Y are each, independently of one another, O and N, provided that: (i) X and Y are not both O and (ii) when X and Y are each N, then Z is CH. The "A" phenyl ring includes at least one, and in many instances two, substituents positioned ortho to the point of attachment ($R^2$ and/or $R^6$) and optionally from 1 to 4 additional substituents, which may be the same or different. Although the "A" ring may include a single ortho ($R^2$ or $R^6$) substituent, compounds which include two ortho substituents ($R^2$ and $R^6$) are particularly active and useful. It is preferable that at least one of the substituent groups at positions $R^2$ and/or $R^6$ provide some steric bulk. For example, it is preferable that the $R^2$ and/or $R^6$ substituent be larger than a fluoro group.

The nature of the $R^2$ and/or $R^6$ substituents, as well as the optional substituents at positions $R^3$, $R^4$ and $R^5$, can vary widely. As a consequence, the "A" phenyl ring may be substituted with virtually any substituent groups, provided that at least one of $R^2$ or $R^6$ is other than hydrogen. When the "A" phenyl ring includes more than one substituent, the substituents may be the same or different. Typical substituent groups useful for substituting the "A" ring include, but are not limited to, branched, straight-chain or cyclic alkyls, mono- or polycyclic aryls, branched, straight-chain or cyclic heteroalkyls, mono- or polycyclic heteroaryls, halos, branched, straight-chain or cyclic haloalkyls, hydroxyls, oxos, thioxos, branched, straight-chain or cyclic alkoxys, branched, straight-chain or cyclic haloalkoxys, trifluoromethoxys, mono- or polycyclic aryloxys, mono- or polycyclic heteroaryloxys, ethers, alcohols, sulfides, thioethers, sulfanyls (thiols), imines, azos, azides, amines (primary, secondary and tertiary), nitriles (any isomer), cyanates (any isomer), thiocyanates (any isomer), nitrosos, nitros, diazos, sulfoxides, sulfonyls, sulfonic acids, sulfamides, sulfonamides, sulfamic esters, aldehydes, ketones, carboxylic acids, esters, amides, amidines, formadines, amino acids, acetylenes, carbamates, lactones, lactams, glucosides, gluconurides, sulfones, ketals, acetals, thioketals, oximes, oxamic acids, oxamic esters, etc., and combinations of these groups.

These substituent groups may be further substituted at one or more available carbon or heteroatoms with the same or different additional substituents, which may be selected from the substituents described above. Any reactive functionalities in the groups used to substituted the "A" phenyl ring may be masked with a protecting group or a progroup, as is well-known in the art.

The substituent groups may be attached directly to the phenyl ring, or they may be spaced away from the ring by way of a linker. The nature of the linker can vary widely, and can include virtually any combination of atoms or groups useful for spacing one molecular moiety from another. For example, the linker may be an acyclic hydrocarbon bridge (e.g, a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3] naphthaleno, and the like), a simple acyclic heteroatomic or heteroalkyldiyl bridge (e.g., —O—, —S—, —S—O—, —NH—, —PH—, —C(O)—, —C(O)NH—, —S(O)—, —S(O)$_2$—, —S(O)NH—, —S(O)$_2$NH—, —O—CH$_2$—, —CH$_2$—O—CH$_2$—, —O—CH=CH—CH$_2$—, and the like), a monocyclic or polycyclic heteroaryl bridge (e.g., [3,4]furano, pyridino, thiopheno, piperidino, piperazino, pyrizidino, pyrrolidino, and the like) or combinations of such bridges. In one embodiment, the "A" ring is substituted at both $R^2$ and $R^6$ with the same or different halo, alkyl, substituted alkyl, alkoxy, substituted alkoxy, methoxy, haloalkyl, trifluoromethyl, 5–6 membered cycloheteroalkyl or substituted 5–6 membered cycloheteroalkyl group.

The "C" ring is substituted at the meta position with a group of the formula —NR$^{11}$C(O)R$^{12}$, where $R^{11}$ is hydrogen or lower alkyl and $R^{12}$ is monohalomethyl or dihalomethyl. The "C" ring may optionally include from 1 to 4 additional substituents ($R^8$, $R^9$, $R^{10}$ and/or $R^{13}$), which may be the same or different. As for the "A" phenyl ring, the nature of the optional $R^8$, $R^9$, $R^{10}$ and $R^{13}$ substituents can vary broadly. Groups useful for substituting the "C" phenyl ring are the same as those described for the "A" phenyl ring, supra. In one embodiment, the "C" ring does not include optional substituents, such that $R^8$, $R^9$, $R^{10}$ and $R^{13}$ are each hydrogen.

As will be recognized by skilled artisans, the actual electron distribution or double bonding pattern of the "B" ring will depend upon the identities of substituents X and Y. As illustrated, structural formula (I) is specifically intended to include at least the following six structures:

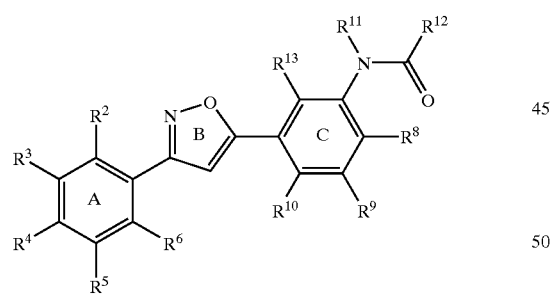

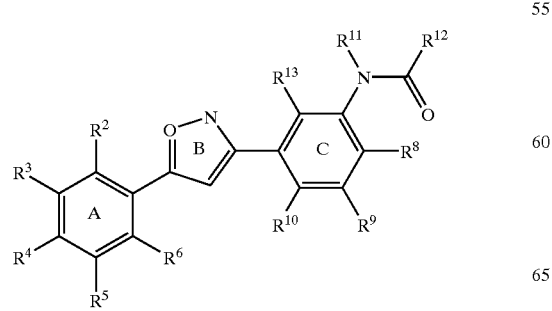

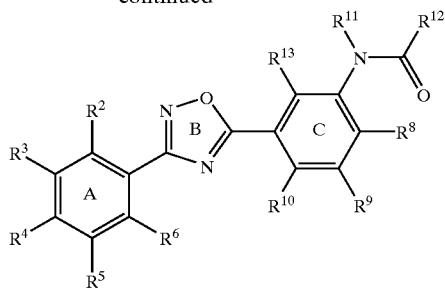

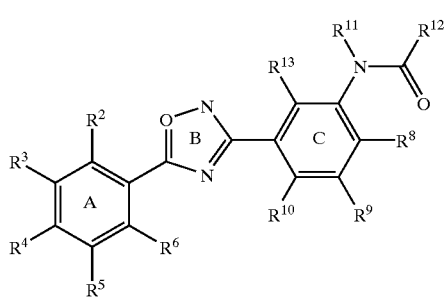

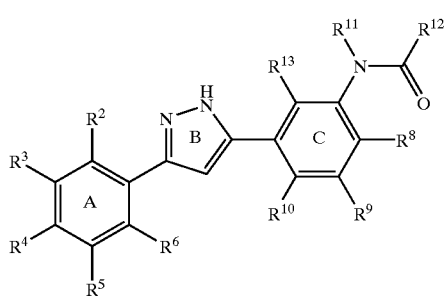

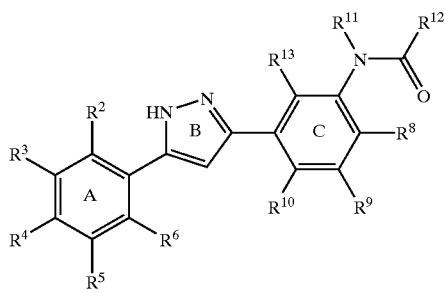

In another aspect, the invention provides starting and intermediate compounds useful for synthesizing the compounds of the invention. Representative starting and intermediate compounds useful for synthesizing isoxazole and pyrazole compounds of the invention include compounds 201, 203, 205, 207, 209, 223, 225, 227, 229, 231, 245, 247, 248a, 248b, 249, 257 and 259 as depicted in FIGS. 1–7. Representative starting and intermediate compounds useful for synthesizing oxadiazole compounds of the invention include compounds 265, 267, 269, 271, 285, 287 and 289 as depicted in FIGS. 1–7.

In one embodiment, the intermediates are compounds according to structural formula (II):

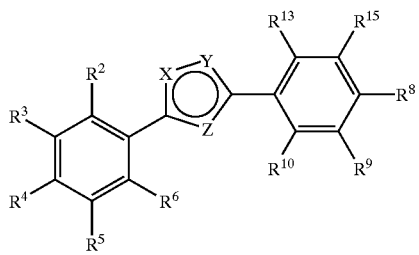

wherein $R^{15}$ is $NO_2$ or NHR, where R is hydrogen, lower alkyl or a protecting group and X, Y, Z, $R^2$, $R^3$, $R^4$, $R^5$, $R^6$, $R^8$, $R^9$, $R^{10}$ and $R^{13}$ are as previously defined for structural formula (I) and subject to the same provisos. Like the compounds of structural formula (I), in the compounds of structural formula (II) the double bonding pattern will depend upon the identities of substituents X and Y.

In another aspect, the invention provides methods of making the substituted diphenyl heterocycle compounds of structural formula (I) or (II). Specific exemplary embodiments of the methods are illustrated in FIGS. 1–7. In one embodiment, the method for synthesizing compounds according to structural formula (I) comprises optionally alkylating a compound according to structural formula (II) in which $R^{15}$ is NHR with an alkylating agent (e.g., $R^{11}$-halide) followed by optional deprotection and acylation with an acylating agent of the formula LG—C(O)—$R^{12}$, where "LG" represents a leaving group or an activating group and $R^{12}$ is as previously defined in connection with the compounds of formula (I).

In another aspect, the present invention provides compositions comprising the compounds of the invention. The compositions generally comprise a substituted diphenyl isoxazole, pyrazole or oxadiazole of the invention, or a salt, hydrate, solvate, N-oxide or prodrug thereof and a suitable excipient, carrier or diluent. The composition may be formulated for veterinary uses or for use in humans.

The compounds of the invention are potent inhibitors of HCV replication and/or proliferation. Accordingly, in still another aspect, the present invention provides methods of inhibiting HCV replication and/or proliferation, comprising contacting a Hepatitis C virion with an amount of a compound or composition of the invention effective to inhibit its replication or proliferation. The methods may be practiced either in vitro or in vivo, and may be used as a therapeutic approach towards the treatment and/or prevention of HCV infections.

In a final aspect, the present invention provides methods of treating and/or preventing HCV infections. The methods generally involve administering to a subject that has an HCV infection or that is at risk of developing an HCV infection an amount of a compound or composition of the invention effective to treat or prevent the HCV infection. The method may be practiced in animals in veterinary contexts or in humans.

5. BRIEF DESCRIPTION OF THE FIGURES

FIGS. 1–7 provide exemplary synthetic schemes for synthesizing the compounds of the invention.

6. DETAILED DESCRIPTION OF THE PREFERRED EMBODIMENTS

6.1 Definitions

As used herein, the following terms are intended to have the following meanings:

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon—carbon bonds, groups having one or more double carbon—carbon bonds, groups having one or more triple carbon—carbon bonds and groups having mixtures of single, double and triple carbon—carbon bonds. Where a specific level of saturation is intended, the expressions "alkanyl," "alkenyl," and "alkynyl" are used. Preferably, an alkyl group comprises from 1 to 15 carbon atoms ($C_1$–$C_{15}$ alkyl), more preferably from 1 to 10 carbon atoms ($C_1$–$C_{10}$ alkyl) and even more preferably from 1 to 6 carbon atoms ($C_1$–$C_6$ alkyl or lower alkyl).

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon—carbon double bond derived by the removal of one hydrogen atom from a single carbon atom of a parent alkene. The group may be in either the cis or trans conformation about the double bond (s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon—carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group comprises from 1 to 6 carbon atoms (C1–C6 alkyldiyl). Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno," by itself or as part of another substituent, refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1–C6) or (C1–C3) alkyleno. Also preferred are straight-chain saturated alkano groups, e.g., methano, ethano, propano, butano, and the like.

"Alkoxy," by itself or as part of another substituent, refers to a radical of the formula —OR, where R is an alkyl or cycloalkyl group as defined herein. Representative examples alkoxy groups include, but are not limited to, methoxy, ethoxy, propoxy, isopropoxy, butoxy, tert-butoxy, cyclopropyloxy, cyclopentyloxy, cyclohexyloxy and the like.

"Alkoxycarbonyl," by itself or as part of another substituent, refers to a radical of the formula —C(O)-alkoxy, where alkoxy is as defined herein.

"Alkylthio," by itself or as part of another substituent, refers to a radical of the formula —SR, where R is an alkyl or cycloalkyl group as defined herein. Representative examples of Alkylthio groups include, but are not limited to, methylthio, ethylthio, propylthio, isopropylthio, butylthio tert-butylthio, cyclopropylthio, cyclopentylthio, cyclohexylthio, and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms ($C_6$–$C_{20}$ aryl), more preferably from 6 to 15 carbon atoms ($C_6$–$C_{15}$ aryl) and even more preferably from 6 to 10 carbon atoms ($C_6$–$C_{10}$ aryl).

"Arylalkyl," by itself or as part of another substituent, refers to an acyclic alkyl group in which one of the hydrogen atoms bonded to a carbon atom, typically a terminal or sp$^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_6$–$C_{30}$) arylalkyl, e.g., the alkanyl, alkenyl or alkynyl moiety of the arylalkyl group is ($C_1$–$C_{10}$) alkyl and the aryl moiety is ($C_6$–$C_{20}$) aryl, more preferably, an arylalkyl group is ($C_6$–$C_{20}$) arylalkyl, e.g., the alkanyl, alkenyl or alkynyl moiety of the arylalkyl group is ($C_1$–$C_8$) alkyl and the aryl moiety is ($C_6$–$C_{12}$) aryl, and even more preferably, an arylalkyl group is ($C_6$–$C_{15}$) arylalkyl, e.g., the alkanyl, alkenyl or alkynyl moiety of the arylalkyl group is ($C_1$–$C_5$) alkyl and the aryl moiety is ($C_6$–$C_{10}$) aryl.

"Aryloxy," by itself or as part of another substituent, refers to a radical of the formula —O-aryl, where aryl is as defined herein.

"Arylalkyloxy, by itself or as part of another substituent, refers to a radical of the formula —O-arylalkyl, where arylalkyl is as defined herein.

"Aryloxycarbonyl," by itself or as part of another substituent, refers to a radical of the formula —C(O)—O-aryl, where aryl is as defined herein.

"Carbamoyl," by itself or as part of another substituent, refers to a radical of the formula —C(O)NR'R", where R' and R" are each, independently of one another, selected from the group consisting of hydrogen, alkyl and cycloalkyl as defined herein, or alternatively, R' and R", taken together with the nitrogen atom to which they are bonded, form a 5-, 6- or 7-membered cycloheteroalkyl ring as defined herein, which may optionally include from 1 to 4 of the same or different additional heteroatoms selected from the group consisting of O, S and N.

"Compounds of the invention" refers to compounds encompassed by the various descriptions and structural formulae disclosed herein. The compounds of the invention may be identified by either their chemical structure and/or chemical name. When the chemical structure and chemical name conflict, the chemical structure is determinative of the identity of the compound. The compounds of the invention may contain one or more chiral centers and/or double bonds and therefore may exist as stereoisomers, such as double-bond isomers (i.e., geometric isomers), rotamers, enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention may also include isotopically labeled compounds where one or more atoms have an atomic mass different from the atomic mass conventionally found in nature. Examples of isotopes that may be incorporated into the compounds of the invention include, but are not limited to, $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. Compounds of the invention may exist in unsolvated forms as well as solvated forms, including hydrated forms and as N-oxides. In general, the hydrated, solvated and N-oxide forms are within the scope of the present invention. Certain compounds of the present invention may exist in multiple crystalline or amorphous forms. In general, all physical forms are equivalent for the uses contemplated by the present invention and are intended to be within the scope of the present invention.

"Cycloalkyl," by itself or as part of another substituent, refers to a saturated or unsaturated cyclic alkyl radical, as defined herein. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. Preferably, the cycloalkyl group comprises from 3 to 10 ring atoms ($C_3$–$C_{10}$ cycloalkyl) and more preferably from 3 to 7 ring atoms ($C_3$–$C_7$ cycloalkyl).

"Cycloheteroalkyl," by itself or as part of another substituent, refers to a saturated or unsaturated cyclic alkyl radical in which one or more carbon atoms (and optionally any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, and the like. Preferably, the cycloheteroalkyl group comprises from 3 to 10 ring atoms (3–10 membered cycloheteroalkyl) and more preferably from 5 to 7 ring atoms (5–7 membered cycloheteroalkyl).

A cycloheteroalkyl group may be substituted at a heteroatom, for example, a nitrogen atom, with a lower alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "cycloheteroalkyl." A cycloheteralkyl group may be attached to the remainder of the molecule via a ring carbon atom or a ring heteroatom.

"Dialkylamino" or "Monoalkylamino," by themselves or as part of other substituents, refer to radicals of the formula —NRR and —NHR, respectively, where each R is independently selected from the group consisting of alkyl and cycloalkyl, as defined herein. Representative examples of dialkylamino groups include, but are not limited to, dimethylamino, methylethylamino, di-(1-methylethyl)amino, (cyclohexyl)(methyl)amino, (cyclohexyl)(ethyl)amino, (cyclohexyl)(propyl)amino and the like. Representative examples of monalkylamino groups include, but are not limited to, methylamino, ethylamino, propylamino, isopropylamino, cyclohexylamino, and the like.

"Halogen" or "Halo," by themselves or as part of another substituent, refer to a fluoro, chloro, bromo and/or iodo radical.

"Haloalkyl," by itself or as part of another substituent, refers to an alkyl group as defined herein in which one or more of the hydrogen atoms is replaced with a halo group. The term "haloalkyl" is specifically meant to include monohaloalkyls, dihaloalkyls, trihaloalkyls, etc. up to perhaloalkyls. The halo groups substituting a haloalkyl can be the same, or they can be different. For example, the expression "($C_1$–$C_2$) haloalkyl" includes 1-fluoromethyl, 1-fluoro-2-chloroethyl, difluoromethyl, trifluoromethyl, 1-fluoroethyl, 1,1-difluoroethyl, 1,2-difluoroethyl, 1,1,1-trifluoroethyl, perfluoroethyl, etc.

"Haloalkyloxy," by itself or as part of another substituent, refers to a group of the formula —O-haloalkyl, where haloalkyl is as defined herein.

"Heteroalkyl," "Heteroalkanyl," "Heteroalkenyl," "Heteroalkynyl," "Heteroalkyldiyl" and "Heteroalkyleno," by themselves or as part of other substituents, refer to alkyl, alkanyl, alkenyl, alkynyl, alkyldiyl and alkyleno groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, O, S, N, Si, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Examples of such heteroalkyl, heteroalkanyl, heteroalkenyl and/or heteroalkynyl groups include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$, —CH$_3$, —CH$_2$—CH$_2$—S(O)—CH$_3$, —CH$_2$—CH$_2$—S(O)$_2$—CH$_3$, —CH=CH—O—CH$_3$, —CH$_2$—CH=N—O—CH$_3$, and —CH$_2$—CH$_2$—O—C=CH. For heteroalkyldiyl and heteroalkyleno groups, the heteratom or heteratomic group can also occupy either or both chain termini. For such groups, no orientation of the group is implied.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group comprises from 5 to 20 ring atoms (5–20 membered heteroaryl), more preferably from 5 to 10 ring atoms (5–10 membered heteroaryl). Preferred heteroaryl groups are those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In preferred embodiments, the heteroarylalkyl group is a 6–21 membered heteroarylalkyl, e.g., the alkanyl, alkenyl or alkynyl moiety of the heteroarylalkyl is (C1–C6) alkyl and the heteroaryl moiety is a 5–15-membered heteroaryl. In particularly preferred embodiments, the heteroarylalkyl is a 6–13 membered heteroarylalkyl, e.g., the alkanyl, alkenyl or alkynyl moiety is (C1–C3) alkyl and the heteroaryl moiety is a 5–10 membered heteroaryl.

"Parent Aromatic Ring System" refers to an unsaturated cyclic or polycyclic ring system having a conjugated $\pi$ electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the; same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Pharmaceutically acceptable salt" refers to a salt of a compound of the invention which is made with counterions understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galactunoric acids and the like (see, e.g., Berge et al., 1977, *J. Pharm. Sci.* 66:1–19).

"Pharmaceutically acceptable vehicle" refers to a diluent, adjuvant, excipient or carrier with which a compound of the invention is administered.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1–8, 1971–1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (e.g., methyl and ethyl esters, acetate or propionate groups or glycol esters) or alkylated such as benzyl and trityl ethers, as well as alkyl ethers, tetrahydropyranyl ethers, trialkylsilyl ethers (e.g., TMS or TIPPS groups) and allyl ethers.

"Prodrug" refers to a derivative of an active compound (drug) that undergoes a transformation under the conditions of use, such as within the body, to release an active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

A wide variety of progroups, as well as the resultant promoieties, suitable for masking functional groups in active compounds to yield prodrugs are well-known in the art. For example, a hydroxyl functional group may be masked as a sulfonate, ester or carbonate promoiety, which may be hydrolyzed in vitro to provide the hydroxyl group. An amino functional group may be masked as an amide, imine, phosphinyl, phosphonyl, phosphoryl or sulfenyl promoiety, which may be hydrolyzed in vivo to provide the amino group. A carboxyl group may be masked as an ester (including silyl esters and thioesters), amide or hydrazide promoicty, which may be hydrolyzed in vivo to provide the carboxyl group. Other specific examples of suitable progroups and their respective promoieties will be apparent to those of skill in the art.

"Progroup" refers to a type of protecting group that, when used to mask a functional group within an active drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —R$^a$, halo, —O$^-$, =O, —OR$^b$, —SR$^b$, —S$^-$, =S, —NR$^c$R$^c$, =NR$^b$, =N—OR$^b$, trihalomethyl, —CF$_3$, —CN, —OCN, —SCN, —NO, —NO$_2$, =N$_2$, —N$_3$, —S(O)$_2$R$^b$, —S(O)$_2$O$^-$, —S(O)$_2$OR$^b$, —OS(O)$_2$R$^b$, —OS(O)$_2$O$^-$, —OS(O)$_2$OR$^b$, —P(O)(O$^-$)$_2$, —P(O)(OR$^b$)(O$^-$), —P(O)(OR$^b$)(OR$^b$), —C(O)R$^b$, —C(S)R$^b$, —C(NR$^b$)R$^b$, —C(O)O$^-$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)O$^-$, —OC(O)OR$^b$, —OC(S)OR$^b$, —NR$^b$C(O)R$^b$, —NR$^b$C(O)R$^b$, —NR$^b$C(O)O$^-$, NR$^c$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$ is selected from the group consisting of alkyl, cycloalkyl, heteroalkyl, cycloheteroalkyl, aryl, arylalkyl, heteroaryl and heteroarylalkyl; each R$^b$ is independently hydrogen or R$^a$; and each R$^c$ is independently R$^b$ or alternatively, the two R$^c$s are taken together with the nitrogen atom to which they are bonded form a 5-, 6- or 7-membered cycloheteroalkyl which may optionally include from 1 to 4 of the same or different additional heteroatoms selected from the group consisting of O, N and S. As specific examples, —NR$^c$R$^c$ is meant to include —NH$_2$, —NH-alkyl, N-pyrrolidinyl and N-morpholinyl.

Similarly, substituent groups useful for substituting unsaturated carbon atoms in the specified group or radical include, but are not limited to, —Ra, halo, —O$^-$, —OR$^b$, —SR$^b$, —S$^-$, —NR$^c$R$^c$, trihalomethyl, —CF$_3$, —CN, —OCN, —SCN, —NO, —NO$_2$, —N$_3$, —S(O)$_2$R$^b$, —S(O)$_2$O, —S(O)$_2$OR$^b$, —OS(O)$_2$R$^b$, —OS(O)$_2$O$^-$, —OS(O)$_2$OR$^b$, —P(O)(O$^-$)$_2$, —P(O)(OR$^b$)(O$^-$), —P(O)(OR$^b$)(OR$^b$), —C(O)R$^b$, —C(S)R$^b$, —C(NR$^b$)R$^b$, —C(O)O$^-$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)O$^-$, —OC(O)OR$^b$, —OC(S)OR$^b$, —NR$^b$C(O)R$^b$, —NR$^b$C(S)R$^b$, —NR$^b$C(O)O$^-$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$, R$^b$ and R$^c$ are as previously defined.

Substituent groups useful for substituting nitrogen atoms in heteroalkyl and cycloheteroalkyl groups include, but are not limited to, —R$^a$, —O$^-$, —OR$^b$, —SR$^b$, —S$^-$, —NR$^c$R$^c$, trihalomethyl, —CF$_3$, —CN, —NO, —NO$_2$, —S(O)$_2$R$^b$, —S(O)$_2$O$^-$, —S(O)$_2$OR$^b$, —OS(O)$_2$R$^b$, —OS(O)$_2$O$^-$, —OS(O)$_2$OR$^b$, —P(O)(O$^-$)$_2$, —P(O)(OR$^b$)(O$^-$), —P(O)(OR$^b$)(OR$^b$), —C(O)R$^b$, —C(S)R$^b$, —C(NR$^b$)R$^b$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)OR$^b$, —OC(S)OR$^b$, —NR$^b$C(O)R$^b$, —NR$^b$C(S)R$^b$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$, R$^b$ and R$^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Sulfamoyl," by itself or as part of another substituent, refers to a radical of the formula —S(O)$_2$NR'R", where R' and R" are each, independently of one another, selected from the group consisting of hydrogen, alkyl and cycloalkyl as defined herein, or alternatively, R' and R", taken together with the nitrogen atom to which they are bonded, form a 5-, 6- or 7-membered cycloheteroalkyl ring as defined herein, which may optionally include from 1 to 4 of the same or different additional heteroatoms selected from the group consisting of O, S and N.

6.2 The Compounds

The invention provides substituted diphenyl heterocycle compounds that are potent inhibitors of HCV replication and/or proliferation. In one embodiment, the compounds of the invention are substituted diphenyl isoxazoles, pyrazoles and oxadiazoles according to structural formula (I):

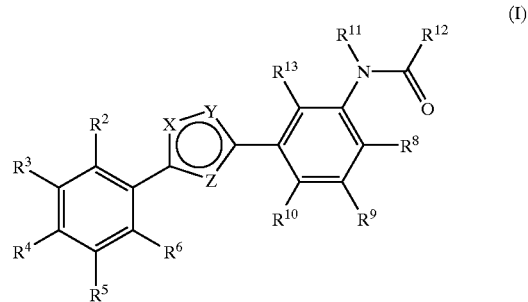

including the pharmaceutically acceptable salts, hydrates, solvates and N-oxides thereof, wherein:

X and Y are each, independently of one another, N or O, provided that X and Y are not both O;

Z is N or —CH—, provided that Z is —CH— when X and Y are both N;

$R^2$, $R^3$, $R^4$, $R^5$, $R^6$, $R^8$, $R^9$, $R^{10}$ and $R^{13}$ are each, independently of one another, selected from the group consisting of hydrogen, —OH, —SH, —CN, —NO$_2$, halo, fluoro, chloro, bromo, iodo, lower alkyl, substituted lower alkyl, lower heteroalkyl, substituted lower heteroalkyl, cycloalkyl, substituted cycloalkyl, cycloheteroalkyl, substituted cycloheteroalkyl, lower haloalkyl, monohalomethyl, dihalomethyl, trihalomethyl, trifluoromethyl, lower alkylthio, substituted lower alkylthio, lower alkoxy, substituted lower alkoxy, methoxy, substituted methoxy, lower heteroalkoxy, substituted lower heteroalkoxy, cycloalkoxy, substituted cycloalkoxy, cycloheteroalkoxy, substituted cycloheteroalkoxy, lower haloalkoxy, monohalomethoxy, dihalomethoxy, trihalomethoxy, trifluoromethoxy, amino, lower di- or monoalkylamino, substituted lower di- or monoalkylamino, aryl, substituted aryl, aryloxy, substituted aryloxy, phenoxy, substituted phenoxy, arylalkyl, substituted arylalkyl, arylalkyloxy, substituted arylalkyloxy, benzyl, benzyloxy, heteroaryl, substituted heteroaryl, heteroaryloxy, substituted heteroaryloxy, heteroarylalkyl, substituted heteroarylalkyl, heteroarylalkyloxy, substituted heteroarylalkyloxy, carboxyl, lower alkoxycarbonyl, substituted lower alkoxycarbonyl, aryloxycarbonyl, substituted aryloxycarbonyl, arylalkyloxycarbonyl, substituted arylalkyloxycarbonyl, carbamate, substituted carbamate, carbamoyl, substituted carbamoyl, sulfamoyl, substituted sulfamoyl and a group of the formula —L—$R^{14}$, where "L" is a linker and $R^{14}$ is cycloalkyl, substituted cycloalkyl, cycloheteroalkyl or substituted cycloheteroalkyl, provided that at least one of $R^2$ or $R^6$ is other than hydrogen;

$R^{11}$ is hydrogen or lower alkyl; and $R^{12}$ is monohalomethyl or dihalomethyl.

In the compounds of formula (I), one alternative group for substituents $R^2$, $R^3$, $R^4$, $R^5$, $R^6$, $R^8$, $R^9$, $R^{10}$ and $R^{13}$ is a group of the formula —L—$R^{14}$, where "L" is a linker. The linker may be any group of atoms suitable for attaching the $R^{14}$ moiety to the illustrated phenyl group. Suitable linkers include, but are not limited to, moieties selected from the group consisting of —$(CH_2)_{1-6}$—, O, S, —C(O)—, —$SO_2$—, —NH—, —NHC(O)—, —C(O)—, —$SO_2NH$— and combinations thereof. In one embodiment, "L" is selected from the group consisting of —$(CH_2)_{1-3}$—, —O—$(CH_2)_{1-3}$—, —S—$(CH_2)_{1-3}$— and —$SO_2$—.

In such L—$R^{14}$ moieties, $R^{14}$ is as defined above. In one embodiment, $R^{14}$ is selected from the group consisting of morpholinyl, N-morpholinyl, piperazinyl, N-piperazinyl, N-methyl-N-piperazinyl, imidazolinyl, N-imidazolidinyl, N-methyl-N-imidazolidinyl, piperidinyl, N-piperidinyl, pyrrolidinyl, N-pyrrolidinyl, pyrazolidinyl, N-pyrazolidinyl and N-methyl-N-pyrazolidinyl.

In the compounds of formula (I), specific examples of substituent groups when $R^2$, $R^3$, $R^4$, $R^5$, $R^6$, $R^8$, $R^9$, $R^{10}$ and/or $R^{13}$ are a substituted alkyl group include methyl, ethyl or propyl groups substituted with a single substituent selected from the group consisting of halo, fluoro, chloro, bromo, hydroxy, lower alkoxy, —CN, —$NO_2$, —C(O)$OR^e$, —OC(O)$OR^e$, —C(O)$NR^fR^g$ and —OC(O)$NR^fR^g$, where each $R^e$ is independently hydrogen, lower alkyl or cycloalkyl; and $R^f$ and $R^g$ are each, independently of one another, selected from the group consisting of hydrogen, lower alkyl and cycloalkyl or, alternatively, $R^f$ and $R^g$, taken together with the nitrogen atom to which they are bonded form a 5-, 6- or 7-membered cycloheteroalkyl ring which may optionally include from 1 to 4 of the same or different additional heteroatoms selected from the group consisting of O, S and N. Further specific examples of substituent groups when $R^2$, $R^3$, $R^4$, $R^5$, $R^6$, $R^8$, $R^9$, $R^{10}$ and/or $R^{13}$ are a substituted alkyl group include —$CH_2$—$R^{17}$, where $R^{17}$ is halo, Br, —OH, lower alkoxy, —CN, $NO_2$, —C(O)$R^e$, —OC(O)$R^e$, —C(O)$NR^fR^g$ and —OC(O)$NR^fR^g$, where $R^e$, $R^f$ and $R^g$ are as defined above.

Specific examples of substituent groups when $R^2$, $R^3$, $R^4$, $R^5$, $R^6$, $R^8$, $R^9$, $R^{10}$ and/or $R^{13}$ are a substituted lower alkoxy group include lower alkoxy groups substituted at the terminal methyl group with a substituent selected from the group consisting of halo, —OH, —CN, —$NO_2$, —C(O)$R^e$, —OC(O)$R^e$, —C(O)$NR^fR^g$ and —OC(O)$NR^fR^g$, where $R^e$, $R^f$ and $R^g$ are as previously defined.

Specific examples of substituent groups when $R^2$, $R^3$, $R^4$, $R^5$, $R^6$, $R^8$, $R^9$, $R^{10}$ and/or $R^{13}$ are aryl or heteroaryl groups include phenyl, 5- or 6-membered heteroaryl, furanyl, imidazolyl, isothiazolyl, isoxazolyl, pyranyl, pyrazinyl, pyrazolyl, pyridazinyl, pyridinyl, pyrimidinyl, pyrrolyl and thiophenyl. The various heteroaryl groups may be connected to the remainder of the molecule via any available carbon atom or heteroatom. In one embodiment, heteroaryl groups containing ring nitrogen atoms are attached to the remainder of the molecule via a ring nitrogen atom. The heteroaryl groups may also be substituted at one or more ring nitrogen atoms with a lower alkyl, lower alkanyl or methyl group.

Specific examples of substituent groups when $R^2$, $R^3$, $R^4$, $R^5$, $R^6$, $R^8$, $R^9$, $R^{10}$ and/or $R^{13}$ are carbamoyl or substituted carbamoyl groups include groups of the formula —C(O)$NR^hR^i$, where $R^h$ and $R^i$ are taken together with the nitrogen atom to which they are bonded to form a 5- or 6-membered cycloheteroalkyl ring which may optionally include from 1 to 4 of the same or different additional heteratoms selected from O, S and N and which is optionally substituted at one or more ring carbon or heteratoms with a substituent selected from the group consisting of lower alkyl, lower alkanyl, methyl, —OH, =O, —C(O)$OR^e$, —C(O)$NR^fR^g$, —OC(O)$R^e$, —C(O)$NR^fR^g$ and aryl, where $R^e$, $R^f$ and $R^g$ are as previously defined. Further specific examples include sulfamoyl or substituted sulfamoyl groups of the formula —C(O)$NR^hR^i$, where $NR^hR^i$ is selected from the group consisting of N-methyl-piperazine, 4-oxo-piperidine, 4-amino-piperdine, 4-(mono-or dialkylamino) piperidine and 4-hydroxy-piperdine.

Specific examples of substituent groups when $R^2$, $R^3$, $R^4$, $R^5$, $R^6$, $R^8$, $R^9$, $R^{10}$ and/or $R^{13}$ are a substituted mono- or dialkylamino group include those mono or dialkylamino groups in which at least one of the alkyl moieties is substituted, preferably at a terminal methyl group, with a substituent selected from the group consisting of —OH and —$NR^eR^e$, where each $R^e$ is as previously defined. Specific examples of such substituted mono- and dialkylamino groups include —N($R^k$)—$(CH_2)_{1-3}$—$NR^kR^k$ and —N($R^k$)—$(CH_2)_{1-3}$—$OR^k$, where each $R^k$ is independently hydrogen, lower alkyl or methyl.

Specific examples of substituent groups when $R^2$, $R^3$, $R^4$, $R^5$, $R^6$, $R^8$, $R^9$, $R^{10}$ and/or $R^{13}$ is a cycloheteroalkyl or substituted cycloheteroalkyl group include 5- or 6-membered cycloheteroalkyl, imidazolidinyl, morpholinyl, piperazinyl, piperadinyl, pyrazolidinyl and pyrrolidinyl, wherein the ring may be optionally substituted at a ring carbon atom with a substituent selected from the group consisting of —$OR^e$, —$NR^fR^g$ and —C(O)$OR^e$, where $R^e$, $R^f$ and $R^g$ are as previously defined. The cycloheteroalkyl or substituted cycloheteroalkyl may be attached to the remainder of the molecule via any available ring carbon or heteroatom. In one embodiment, the cycloheteroalkyl or substituted cycloheteroalkyl is attached to the remainder of the molecule via a ring nitrogen atom. Further specific examples of substituted cycloheteroalkyls suitable as $R^2$, $R^3$, $R^4$, $R^5$, $R^6$, $R^8$, $R^9$, $R^{10}$ and/or $R^{13}$ substituents include N-piperidinyl substituted at the 4-position, or N-pyrrolidinyl substituted at the 3-position, with a lower alkoxycarbonyl, amino, mono- or dialkylamino or N-piperidinyl group.

Additional specific examples of $R^2$, $R^3$, $R^4$, $R^5$, $R^6$, $R^8$, $R^9$, $R^{10}$ and $R^{13}$ as well as specific combinations of substituents for the "A" and "C" phenyl rings are provided in TABLE 1, infra.

In one embodiment of the compounds of structural formula (I), Z is —CH— such that the compounds are isoxazoles or pyrazoles. In another embodiment of the compounds of structural formula (I), Z is N such that the compounds are oxadiazoles. In another embodiment, the compounds of structural formula (I) are isoxazoles.

In another embodiment of the compounds of structural formula (I), three of $R^8$, $R^9$, $R^{10}$ and $R^{13}$ are hydrogen. In a specific embodiment, $R^9$, $R^{10}$ and $R^{13}$ are each hydrogen.

In yet another embodiment of the compounds of structural formula (I), $R^8$, $R^9$, $R^{10}$ and $R^{13}$ are each, independently of one another, selected from the group consisting of hydrogen, halo, fluoro, chloro, bromo, iodo, sulfamoyl, lower alkylthio, lower haloalkyl, monohalomethyl, dihalomethyl, trihalomethyl, trifluoromethyl and —L—$R^{14}$; where L is —(CH$_2$)$_{1-3}$— or —O—(CH$_2$)$_{1-3}$— and $R^{14}$ is a 5- or 6-membered cycloheteroalkyl or N-morpholinyl. In one specific embodiment, three of $R^8$, $R^9$, $R^{10}$ and $R^{13}$ are hydrogen. In another specific embodiment, $R^9$, $R^{10}$ and $R^{13}$ are each hydrogen.

In yet another embodiment of the compounds of structural formula (I), $R^2$ and/or $R^6$ are each, independently of one another, selected from the group consisting of —OH, —NO$_2$, halo, fluoro, chloro, bromo, iodo, lower alkyl, methyl, lower heteroalkyl, (C3–C6) cycloalkyl, 5- or 6-membered cycloheteroalkyl, N-morpholinyl, N-methyl-N-piperazinyl, N-piperadinyl, substituted N-piperadinyl, 4-(N-piperadinyl)-N-piperadinyl, 4-amino-N-piperadinyl, lower alkoxy, methoxy, ethoxy, lower alkylthio, methylthio, lower haloalkyl, monohalomethyl, dihalomethyl, trihalomethyl, trifluoromethyl, lower haloalkyloxy, monohalomethoxy, dihalomethoxy, trihalomethoxy, trifluoromethoxy, aryl, phenyl, arylalkyl, benzyl, aryloxy, phenoxy, arylalkyloxy, benzyloxy, 5- or 6-membered heteroaryl, lower alkyloxycarbonyl, sulfamoyl and —L—$R^{14}$, where L is —(CH$_2$)$_{1-3}$— or —O—(CH$_2$)$_{1-3}$— and $R^{14}$ is a 5- or 6-membered cycloheteroalkyl or N-morpholinyl.

In another embodiment of the compounds of structural formula (I), $R^3$ and $R^5$ are each, independently of one another, selected from the group consisting of hydrogen, halo, fluoro, chloro, lower alkoxyl, lower alkanyloxy, carboxyl, lower alkanyloxycarbonyl, monohalomethyl, dihalomethyl, trihalomethyl and trifluoromethyl.

In still another embodiment of the compounds of structural formula (I), $R^4$ is selected from the group consisting of hydrogen, lower dialkylamino, lower dialkaylamino, dimethylamino, halo, fluoro, chloro and —L—$R^{14}$, where L is —O—(CH$_2$)$_{1-3}$— and $R^{14}$ is 6-membered cycloheteroalkyl, N-morpholinyl or N-piperazinyl.

In yet another embodiment of the compounds of structural formula (I), $R^3$, $R^4$, $R^5$, $R^8$, $R^9$, $R^{10}$ and $R^{13}$ are each hydrogen. Preferably, in this embodiment, $R^2$ and $R^6$ are each, independently of one another, selected from the group consisting of hydroxyl, chloro, fluoro, methoxy, ethoxy, trifluoromethyl, trifluoromethoxy and N-morpholinyl. In a specific embodiment, $R^2$ and $R^6$ are the same or different halo or are each chloro. In another specific embodiment, $R^2$ is fluoro and $R^6$ is trifluoromethyl. Preferably, in the above embodiments, Z is —CH— and/or X is N and Y is O.

In still another embodiment, the compounds of the invention are compounds according to structural formulae (Ia), (Ib), (Ic) and/or (Id):

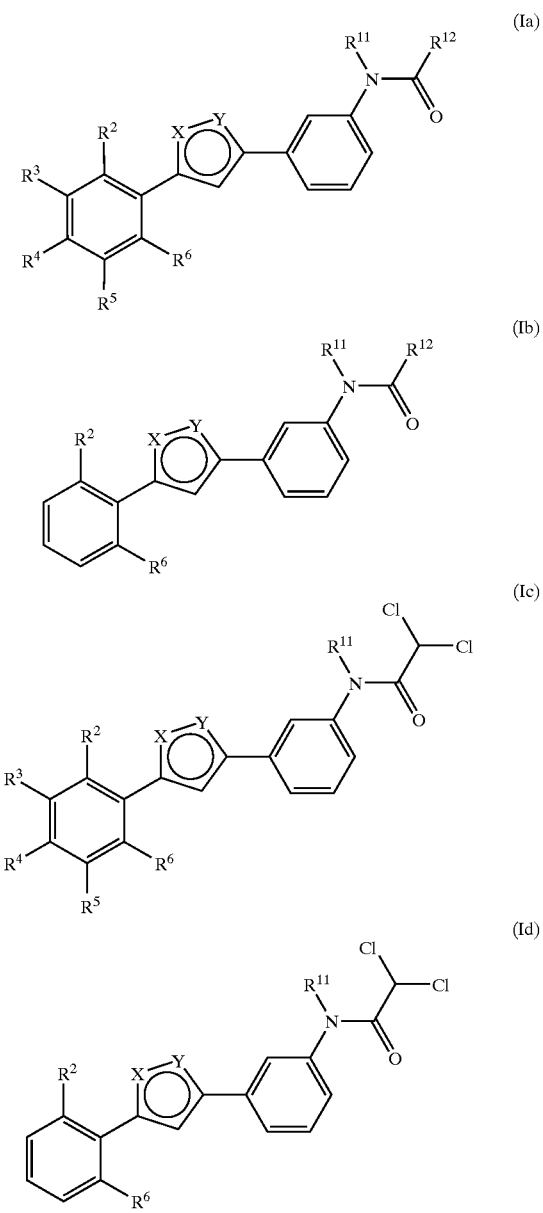

including the pharmaceutically acceptable salts, hydrates, solvates and N-oxides thereof, wherein X, Y, $R^2$, $R^3$, $R^4$, $R^5$, $R^6$, $R^{11}$ and $R^{12}$ are as previously defined for structural formula (I) and subject to the same provisos. In one embodiment, the compounds of structural formula (Ia), (Ib), (Ic) and/or (Id) have one or more features selected from the group consisting of:

X is N and Y is O;

X is O and Y is N;

$R^{11}$ is hydrogen or methyl;

$R^2$ and $R^6$ are each, independently of one another, selected from the group consisting of hydrogen, hydroxyl, halo, lower alkyl, methyl, lower alkoxy, methoxy, monohalomethyl, dihalomethyl, trihalomethyl, trifluoromethyl, trifluoromethoxy, and N-morpholinyl, provided that at least one of $R^2$ or $R^6$ is other than hydrogen;

$R^3$ and $R^5$ are each hydrogen; and $R^4$ is hydrogen or —L—$R^{14}$, where L is —(CH$_2$)$_{1-3}$— and $R^{14}$ is 6-membered cycloheteroalkyl, preferably comprising from 1 to 2 of the same or different heteroatoms selected from O and N.

Exemplary compounds of the invention are provided in TABLE 1. Also included in the invention are the various regioisomers of the compounds described herein, including the various regioisomers of the compounds of structural formula (I), (Ia), (Ib), (Ic), (Id) and TABLE 1.

Those of skill in the art will appreciate that the compounds of the invention described herein may include functional groups that can be masked with progroups to create prodrugs. Such prodrugs are usually, but need not be, pharmacologically inactive until converted into their active drug form. In the prodrugs of the invention, any available functional moiety may be masked with a progroup to yield a prodrug. Myriad progroups suitable for masking such functional groups to yield promoieties that are cleavable under the desired conditions of use are known in the art. Specific examples are described supra.

6.3 Methods of Synthesis

The compounds of the invention may be obtained via synthetic methods illustrated in FIGS. 1–7. It should be understood that in FIGS. 1–7, $R^2$, $R^3$, $R^4$, $R^5$, $R^6$, $R^7$, $R^8$, $R^9$, $R^{10}$, $R^{11}$, $R^{12}$ and $R^{13}$ are as previously defined for structural formula (I).

Starting materials useful for preparing compounds of the invention and intermediates thereof are commercially available or can be prepared by well-known synthetic methods (see, e.g., Harrison et al., "Compendium of Synthetic Organic Methods", Vols. 1–8 (John Wiley and Sons, 1971–1996); "Beilstein Handbook of Organic Chemistry," Beilstein Institute of Organic Chemistry, Frankfurt, Germany; Feiser et al., "Reagents for Organic Synthesis," Volumes 1–21, Wiley Interscience; Trost et al., "Comprehensive Organic Synthesis," Pergamon Press, 1991; "Theilheimer's Synthetic Methods of Organic Chemistry," Volumes 1–45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," 3d Edition, John Wiley & Sons, 1995). Other methods for synthesis of the compounds described herein and/or starting materials are either described in the art or will be readily apparent to the skilled artisan. Alternatives to the reagents and/or protecting groups illustrated in FIGS. 1–7 may be found in the references provided above and in other compendiums well known to the skilled artisan. Guidance for selecting suitable protecting groups can be found, for example, in Greene & Wuts, "Protective Groups in Organic Synthesis," Wiley Interscience, 1999. Accordingly, the synthetic methods and strategy presented herein are illustrative rather than comprehensive.

One method for synthesizing substituted diphenyl isoxazoles according to structural formula (I) (when Z is —CH—) is provided in FIG. 1A. Referring to FIG. 1A, aldol condensation of methyl ketone 201 with benzaldehyde 203 under basic conditions, followed by in situ dehydration, provides α-β unsaturated enone 205, which may be readily converted to isoxazole 207 by treatment with hydroxylamine. Reduction of 207 yields the amino isoxazole 209, which may be optionally alkylated with $R^{11}$-halide and acylated with LG—C(O)—$R^{12}$ yield 211. In FIG. 1A and throughout the remaining FIGS. 2–7, "LG" represents a leaving or activating group, regardless of the moiety to which it is attached. Myriad suitable leaving and activating groups are known to those of skill in the art. Specific examples useful in the various methods described herein include, but are not limited to, halo, cyano, acyloxy and the myriad other leaving groups known to those of skill in the art to be useful in the formation of amide bonds.

Figure 1B:
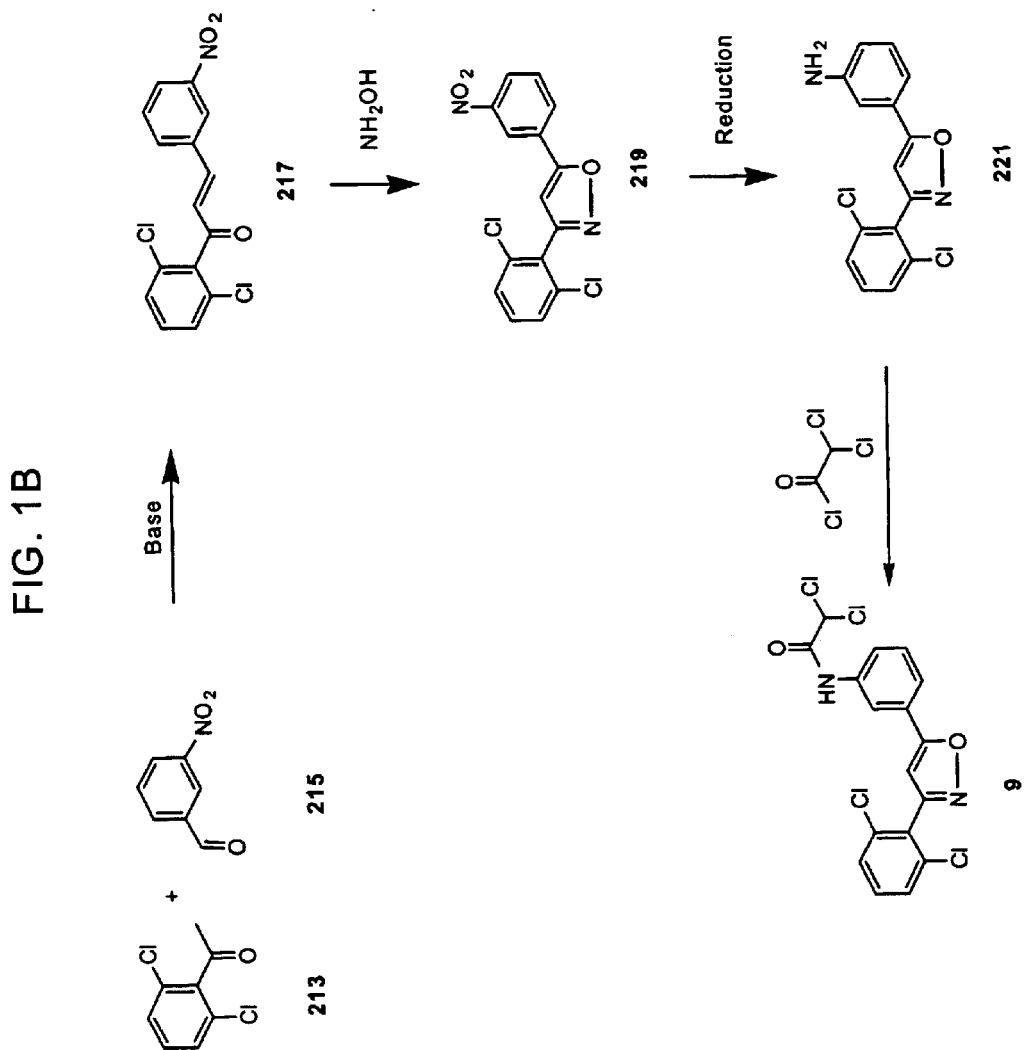

A specific example of the synthetic method of FIG. 1A is illustrated for the preparation of diphenyl isoxazole 9 in FIG. 1B.

Figure 2A:
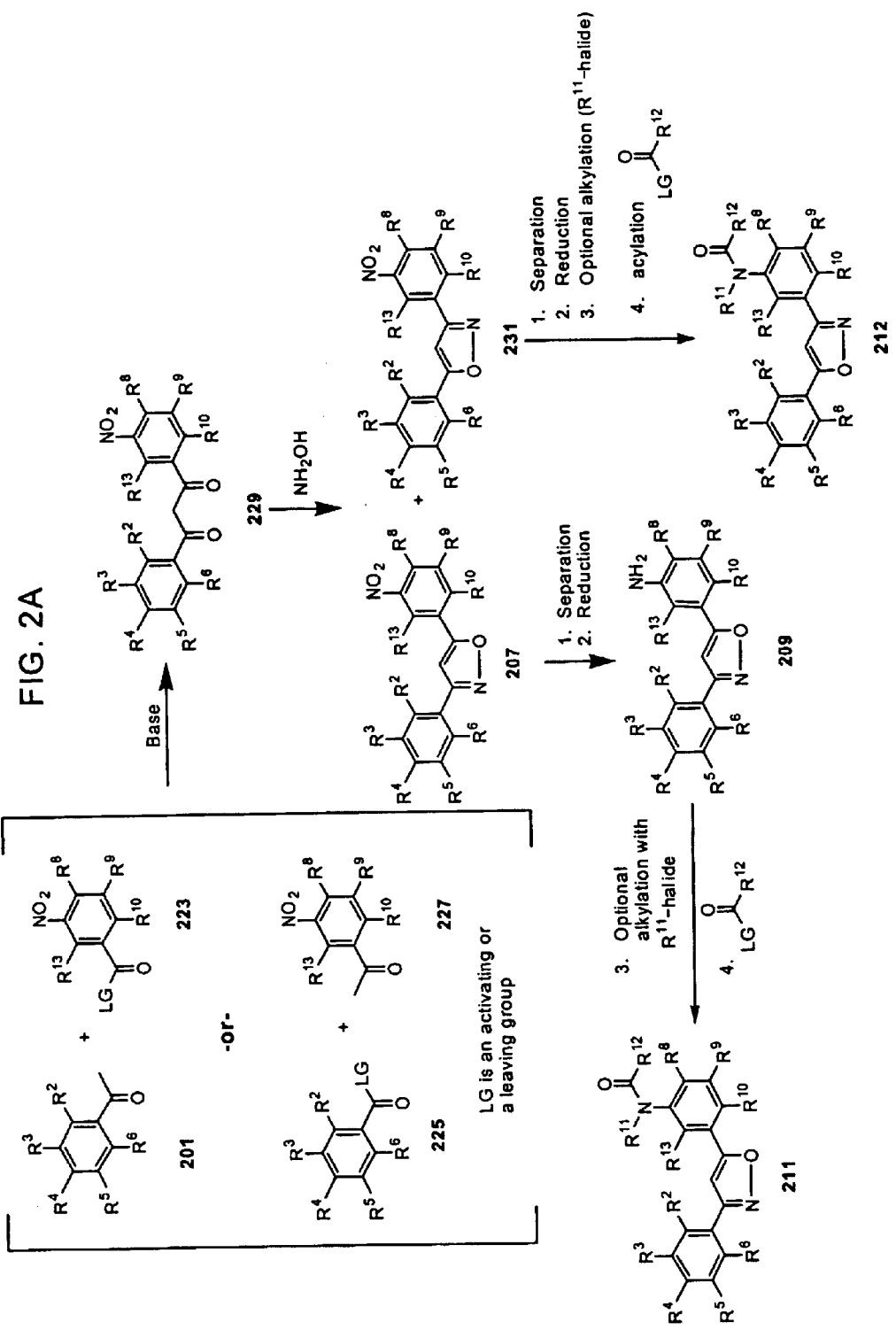
Figure 2B:
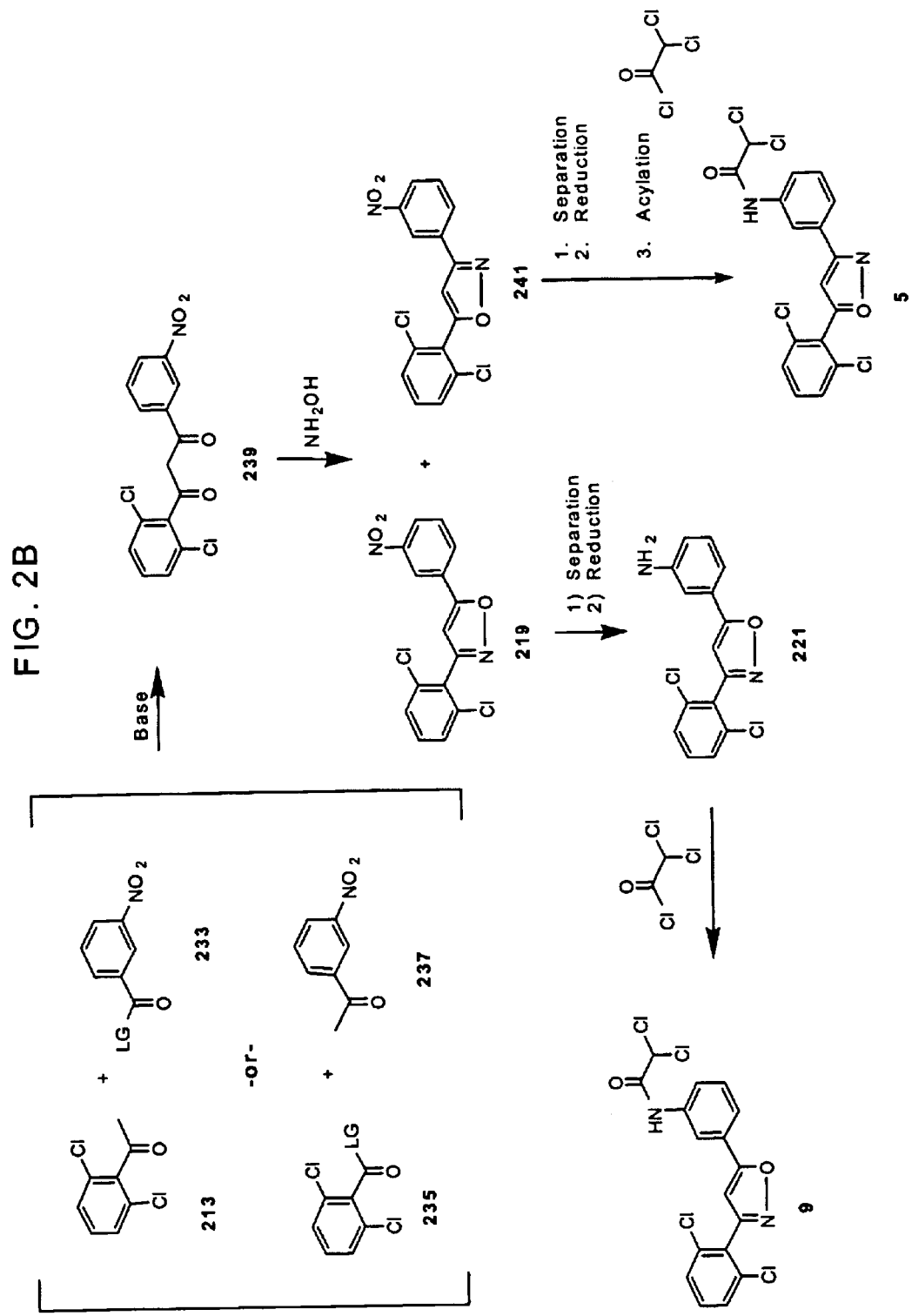

Another method for synthesizing substituted isoxazoles of structural formula (I) (when Z is —CH—) is provided in FIG. 2A. Claisen condensation of methyl ketone 201 with ester 223 under basic conditions provides 1,3 diketone 229, which may be converted to a mixture of isoxazoles 207 and 231 by treatment with hydroxylamine. Isolation and subsequent reduction of 207 yields the amino isoxazole 209, which may be transformed to the isoxazole 211 as previously described or by other well known synthetic methods. It should be noted that isoxazole 231 may be isolated and converted to the corresponding regioisomer of isoxazole 211 (compound 212) by the same synthetic pathway. A specific example of the synthetic method of FIG. 2A is illustrated for the preparation of diphenyl isoxazole 9 and its corresponding regioisomers 5 in FIG. 2B.

In alternative embodiment of the pathway illustrated in FIG. 2A, ester 225 is condensed with methyl ketone 227 to provide 1,3 diketone 229, which is then carried through the remainder of the synthetic pathway as previously described.

Figure 3A:
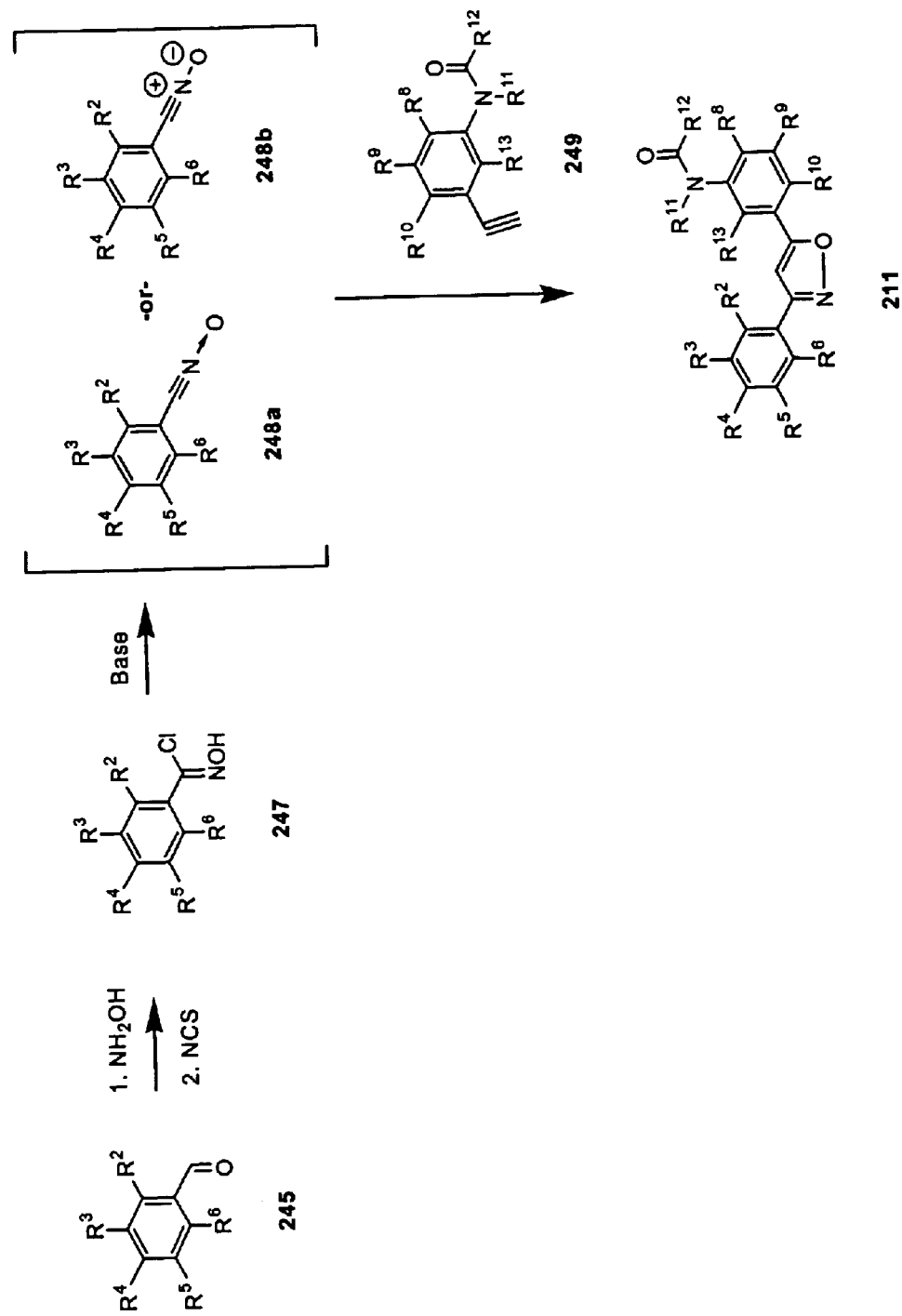
Figure 3B:
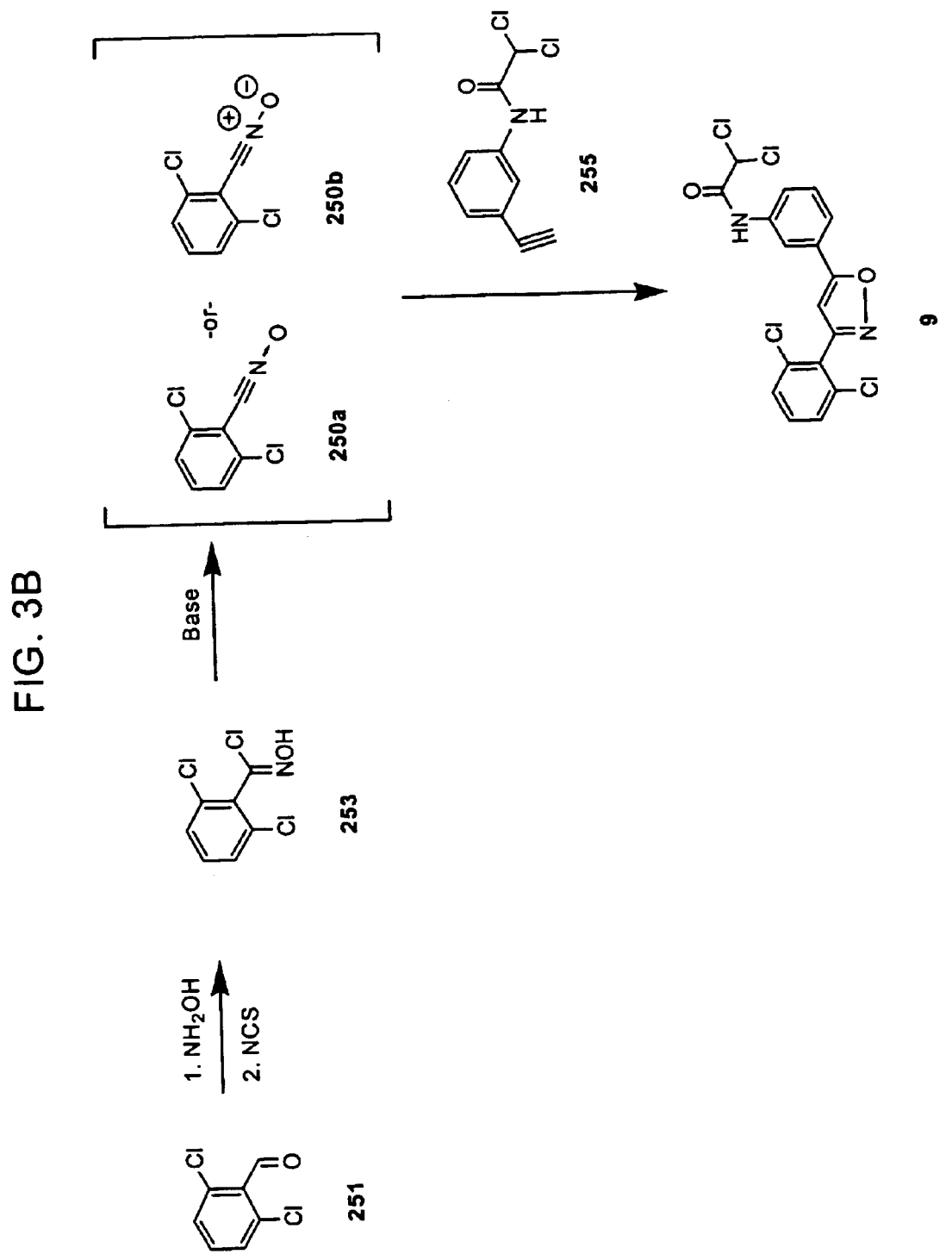

Still another method for synthesizing substituted isoxazoles of structural formula (I) (when Z is —CH—) is provided in FIG. 3A. Nucleophilic addition of hydroxylamine to benzaldehyde 245 provides an intermediate oxime, which may be converted by treatment with N-chlorosuccinimide (NCS) or other methods known in the art to the α-chlorooxime 247. Dehydrohalogenation of α-chlorooxime 247 in the presence of a base yields nitrile oxide 248a or 248b, which undergoes 1,3 dipolar cycloaddition in the presence of acetylene 249 to provide the desired isoxazole 211. As will be recognized by skilled artisans, the nitrile oxide 248a or 248b can be isolated prior to cycloaddition with acetylene 249 or, alternatively, acetylene 249 may be added directly to the reaction mixture without first isolating the nitrile oxide 248a or 248b. Acetylene 249 may be readily prepared from commercially available precursors by well known synthetic methods. Specific methods are provided in FIGS. 7A and 7B. A specific example of the synthetic method of FIG. 3A is illustrated for the preparation of diphenyl isoxazole 9 in FIG. 3B.

Figure 3C:
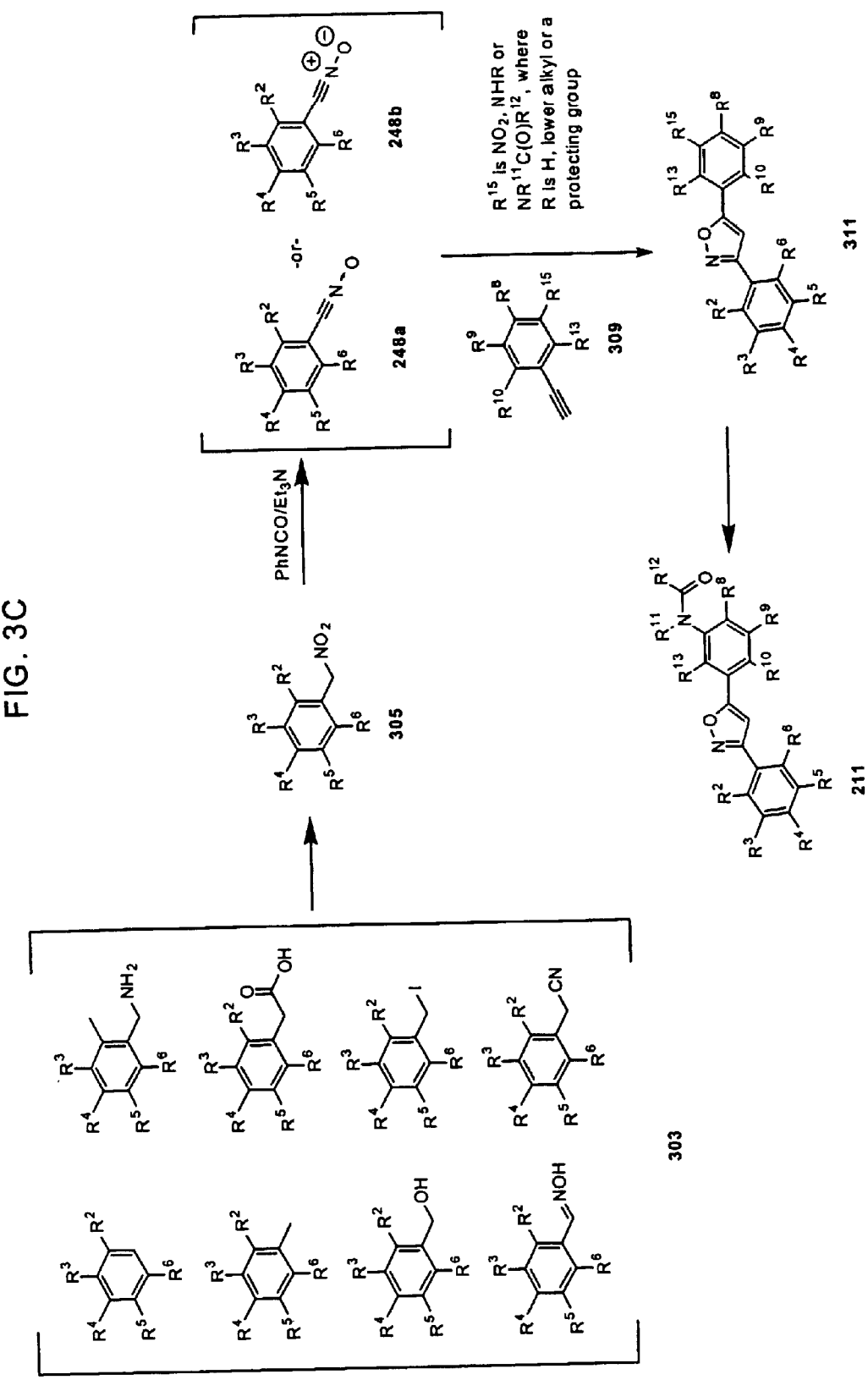

Methods for preparing nitrile oxide 248a or 248b are illustrated in FIG. 3C. Referring to FIG. 3C, myriad different types of benzylic compounds 303 are converted to the benzylic nitro compound 305 using standard techniques. Treatment with phenyl isocyanate in the presence of a weak base yields nitrile oxide 248a or 248b. 1,3-Dipolar cycloaddition with acetylene 309 yields isoxazole 311. In acetylene 309 and isoxazole 311, $R^{15}$ is —$NO_2$, —NHR or —$NR^{11}C(O)R^{12}$, where R is hydrogen, lower alkyl or a protecting group and $R^{11}$ and $R^{12}$ are as previously defined for structural formula (I). Depending upon the identity of $R^{15}$, isoxazole 311 is then converted to isoxazole 211 using the previously described methods.

Figure 4A:
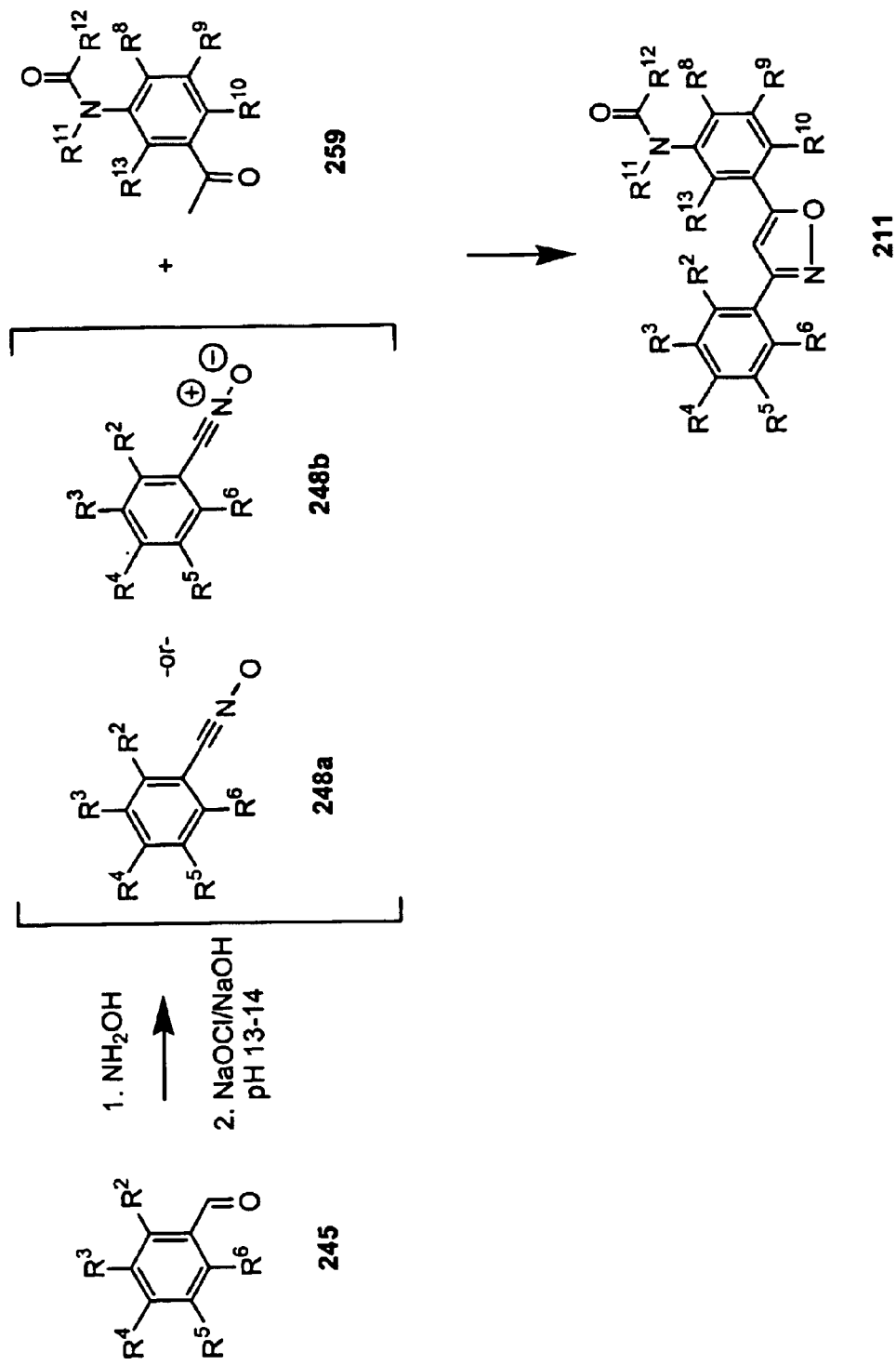
Figure 4B:
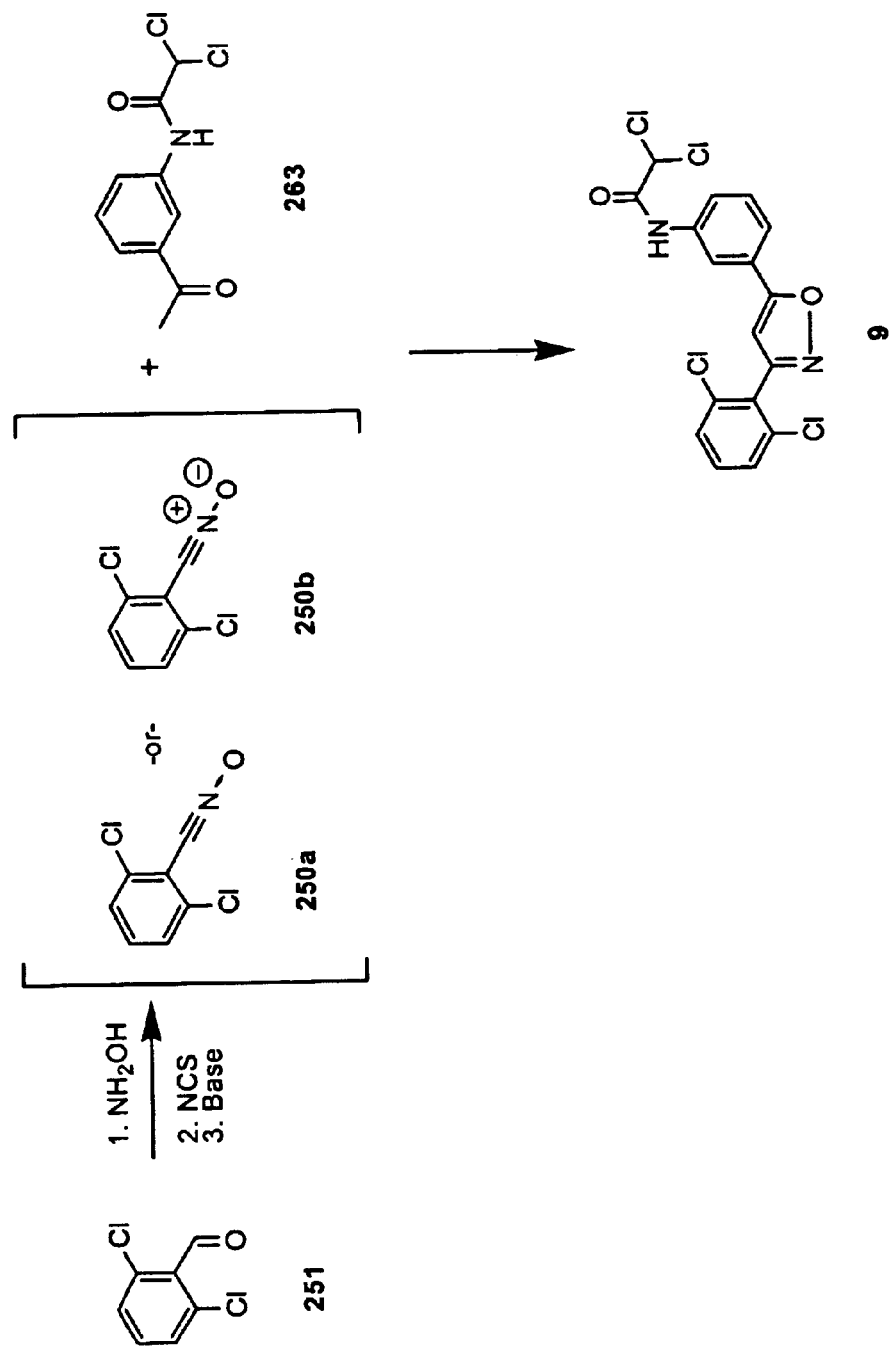
Figure 4C:
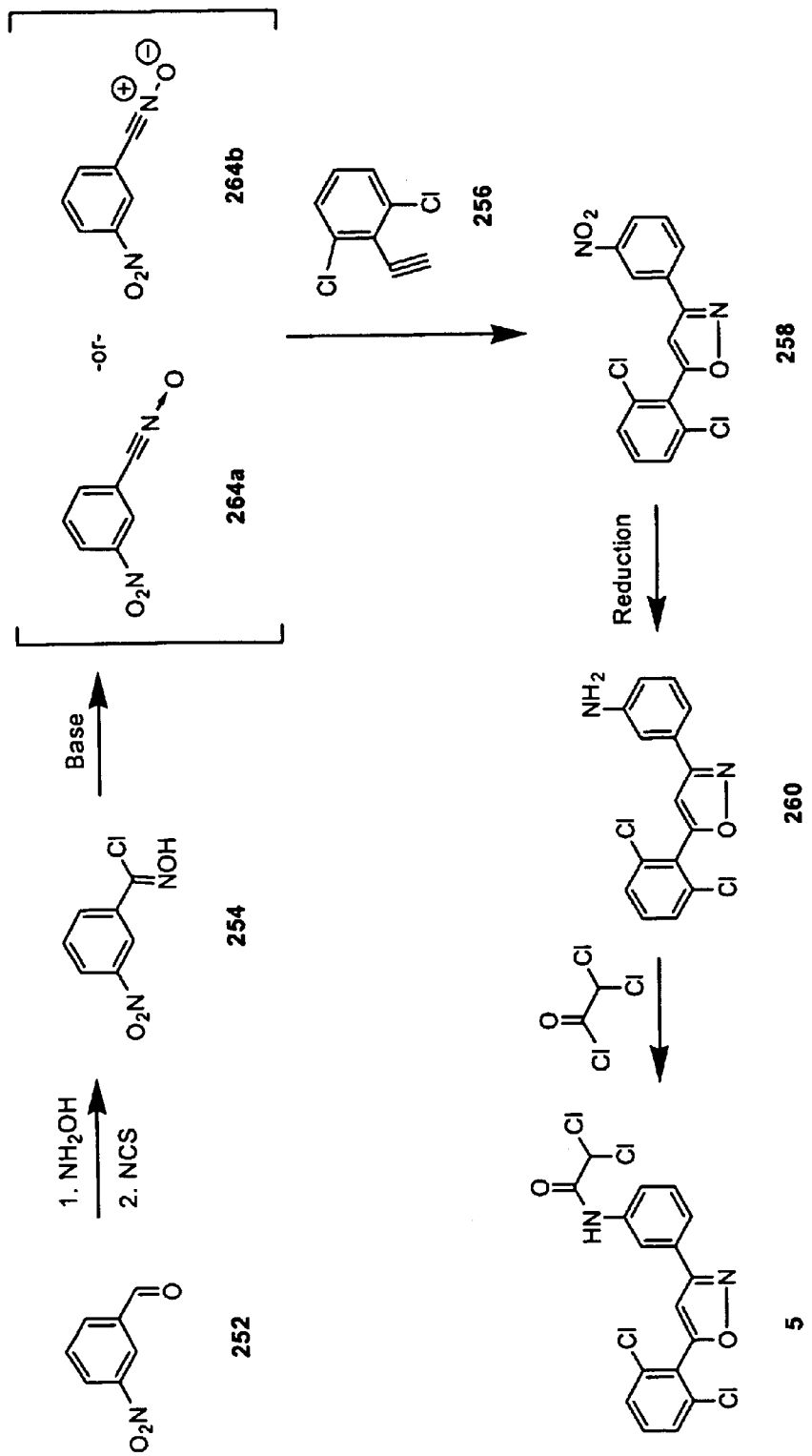

Still another method for synthesizing substituted isoxazoles of structural formula (I) (when Z is —CH—) is provided in FIG. 4A. Nucleophilic addition of hydroxylamine to benzaldehyde 245 provides an intermediate oxime, which may be directly converted to nitrile oxide 248a or 248b with NaOCl in the presence of NaOH. 1,3 Dipolar cycloaddition of nitrile oxide 248a or 248b to methyl ketone 259 provides desired isoxazole 211. Methyl ketone 259 may be readily prepared from commercially available precursors by well known synthetic methods. A specific example of the synthetic method of FIG. 4A is illustrated for the preparation of diphenyl isoxazole 9 in FIG. 4B.

The methods described in FIGS. 1–4 above may be readily adapted for the synthesis of pyrazoles by substituting hydrazine for hydroxylamine in the reaction sequence. Further, those of skill in the art will appreciate that isoxazole regioisomers of those depicted in the above FIGS. 1–4 may be synthesized by merely interchanging the reactive functionalities of the two different aromatic rings. An example of this approach is depicted in FIG. 4C for "reverse" isoxazole 5. As can be seen in FIG. 4C, interchanging the chlorooxime and alkyne functionalities of the two different aromatic rings (i.e., rings A and C) provides the regioisomeric isoxazole 5 (compare 253 and 255 with 254 and 256). Further, certain synthetic schemes may provide both isoxazole regioisomers (e.g., FIGS. 2A and 2B) directly, which may be isolated from one another using standard techniques.

Figure 5A:
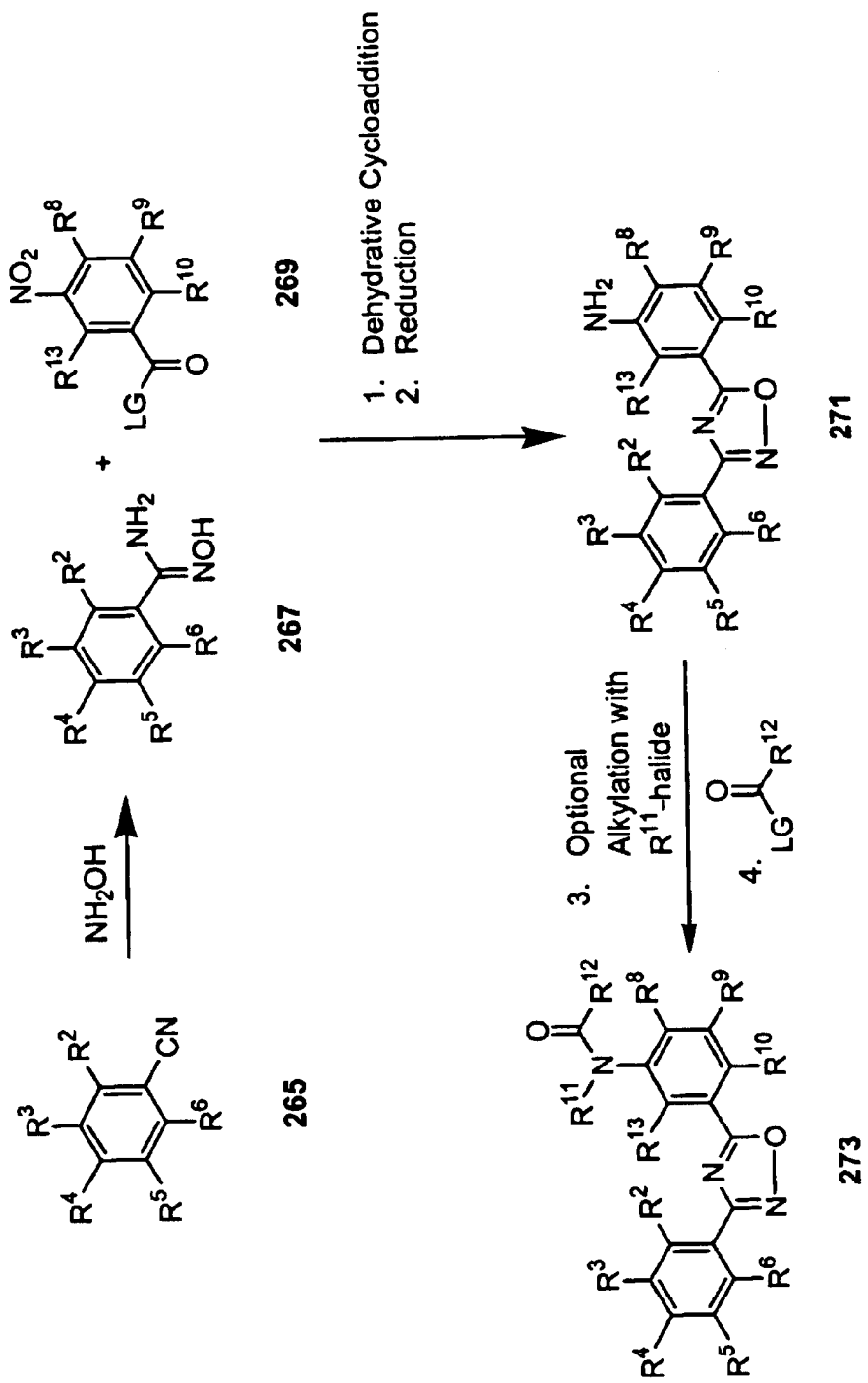
Figure 5B:
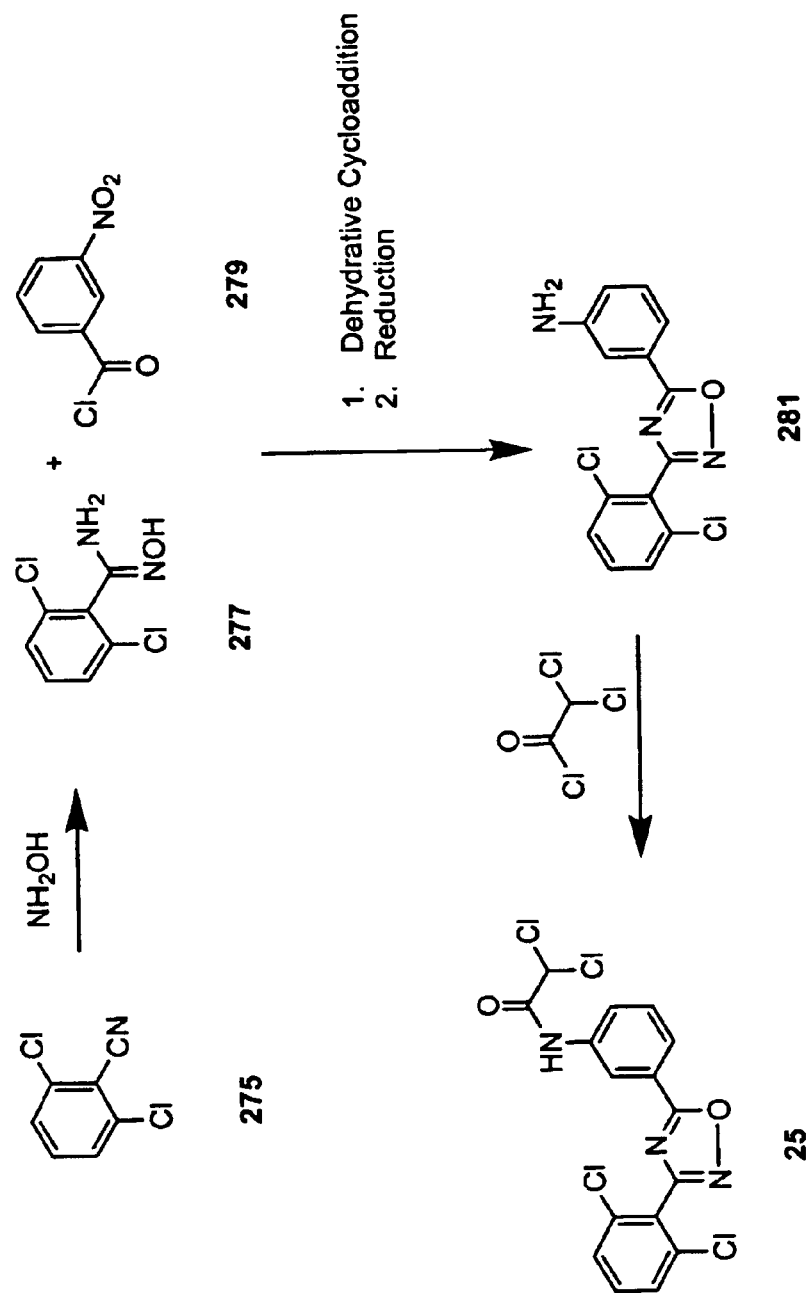

One method for synthesizing substituted oxadiazoles of structural formula (I) (when Z is —N—) is provided in FIG. 5A. Referring to FIG. 5A, nucleophilic addition of hydroxylamine to phenyl cyanide 265 yields the amide oxime 267, which may be condensed with compound 269 to provide oxadiazole 271 after dehydrative cyclization and reduction. Amino oxadiazole 271 may be optionally alkylated followed by acylation, as described above, to yield oxadiazole 273. A specific example of the synthetic method of FIG. 5A is illustrated for the preparation of diphenyl oxadiazole 25 in FIG. 5B.

Figure 6A:
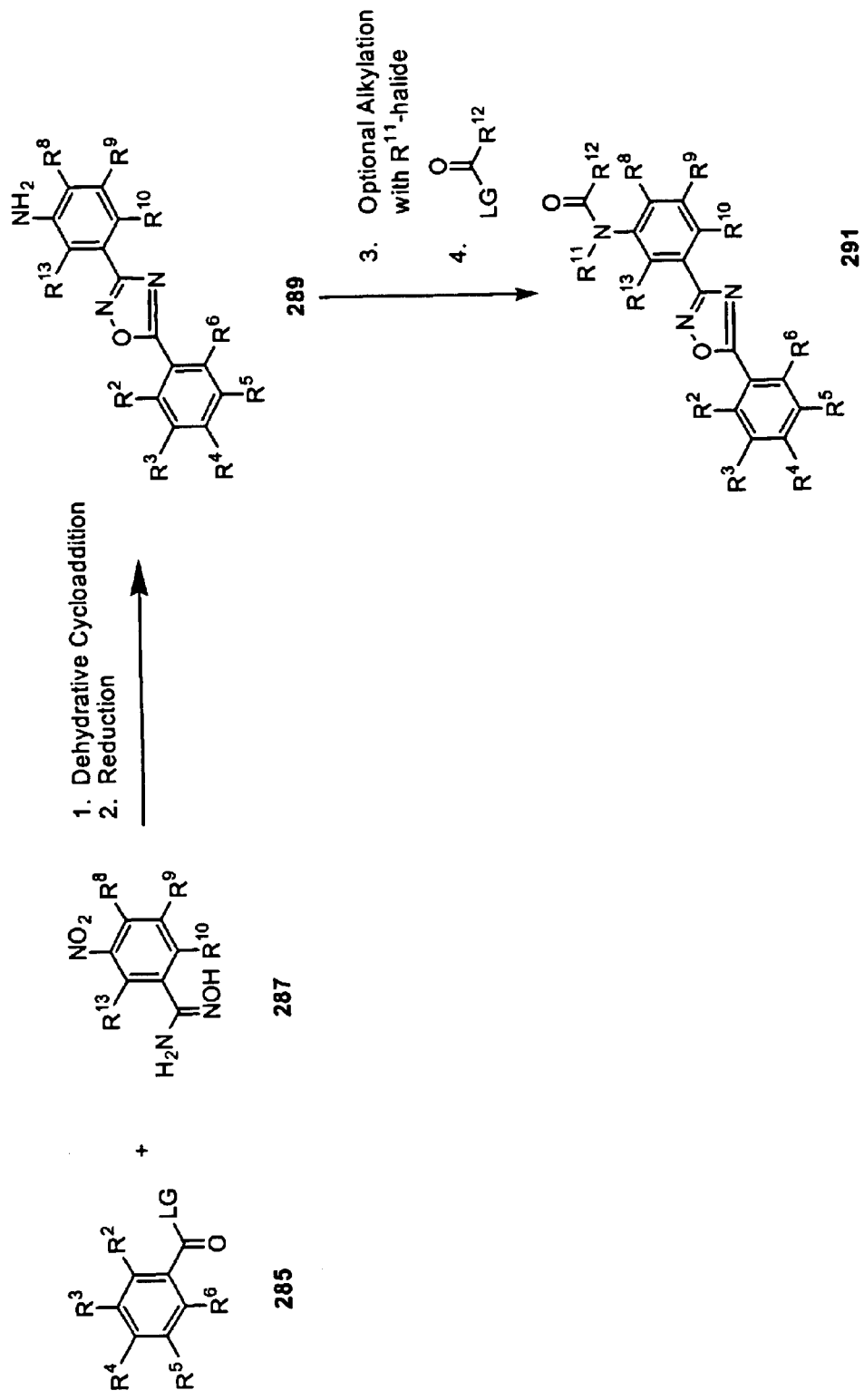
Figure 6B:
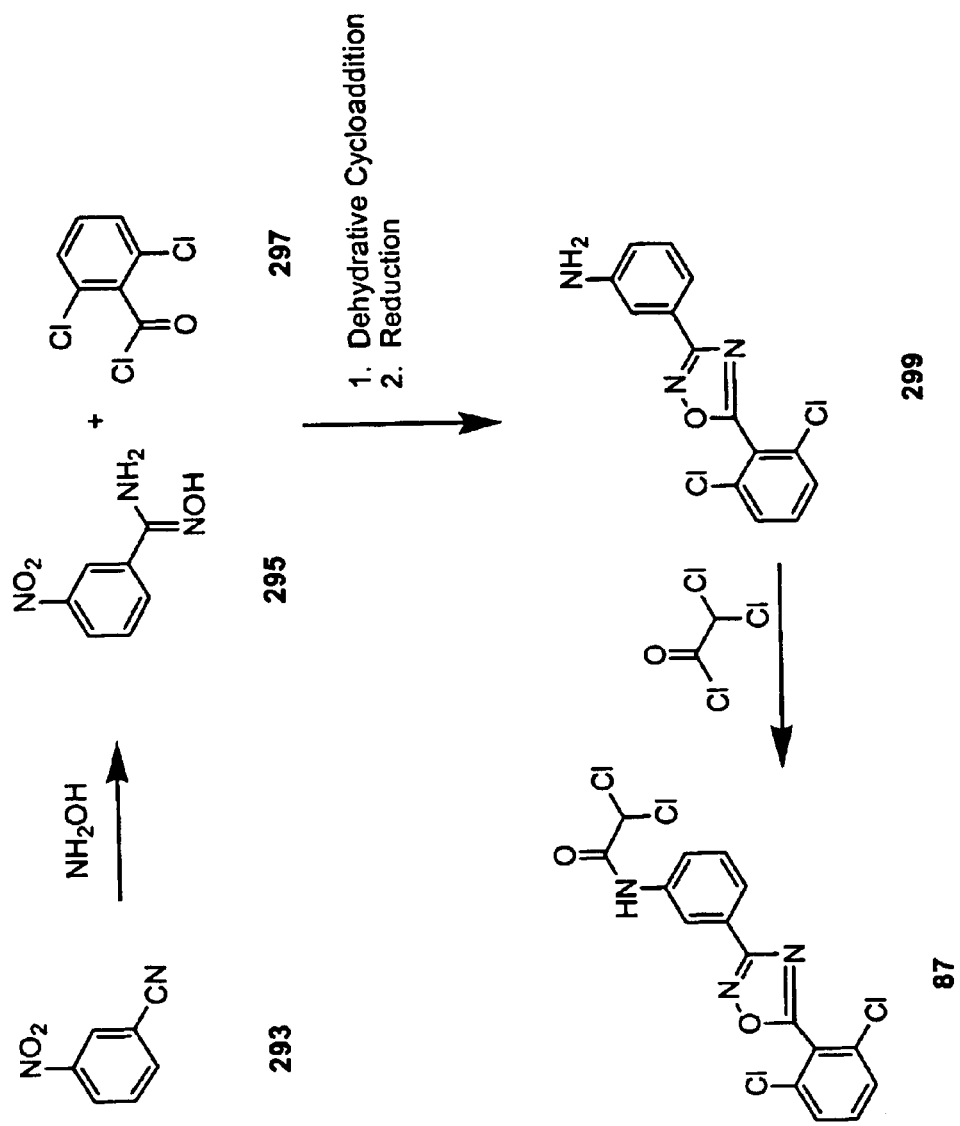

Another method for synthesizing substituted oxadiazoles of structural formula (I) (when Z is —N—), which are regioisomers of those prepared above, is provided in FIG. 6A. Referring to FIG. 6A, amide oxime 287, (prepared by condensation of hydroxyl amine with a phenyl cyanide), may be condensed with acylating agent 285, which may be an acyl chloride, to provide oxadiazole 289 after dehydrative cyclization and reduction. Amino oxadiazole 289 may be transformed by the previously described methods to final product 291. A specific example of the synthetic method of FIG. 6A is illustrated for the preparation of diphenyl oxadiazole 87 in FIG. 6B.

Figure 7A:
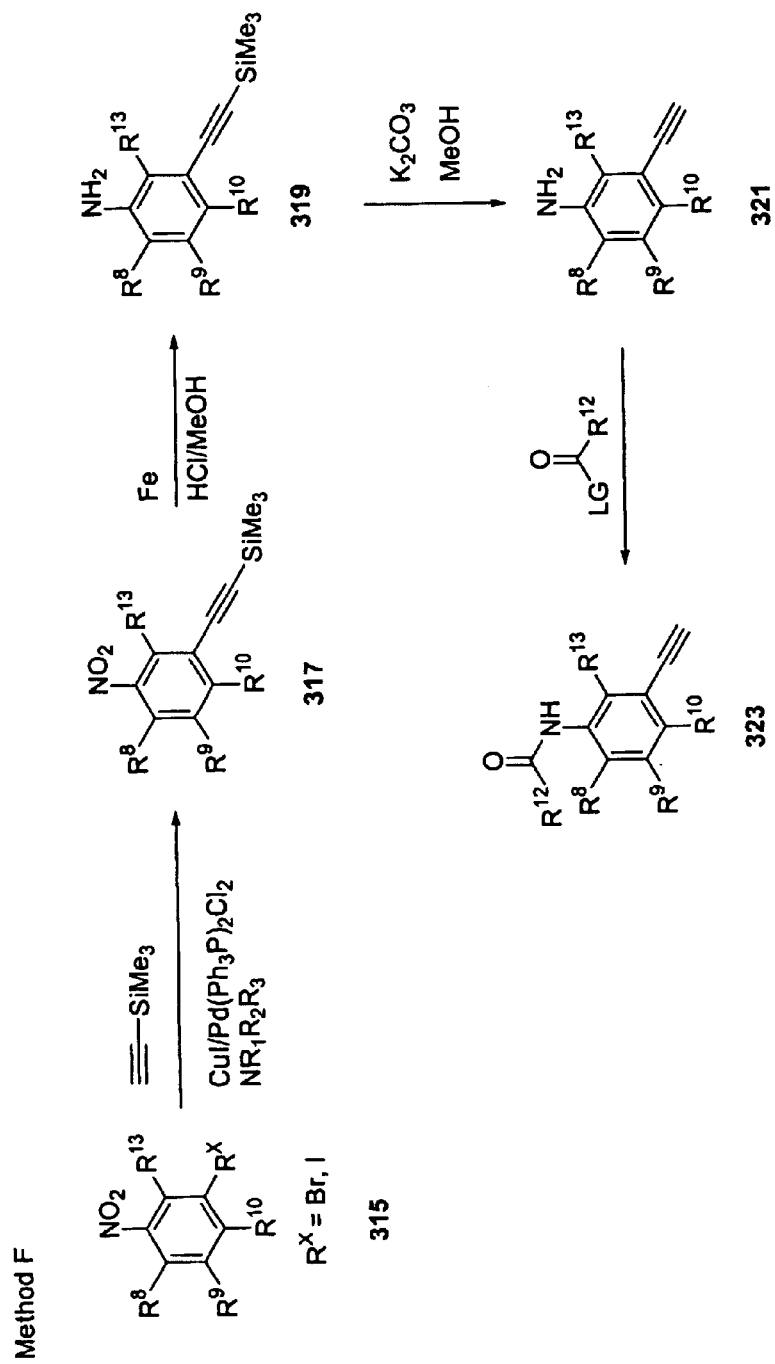
Figure 7B:
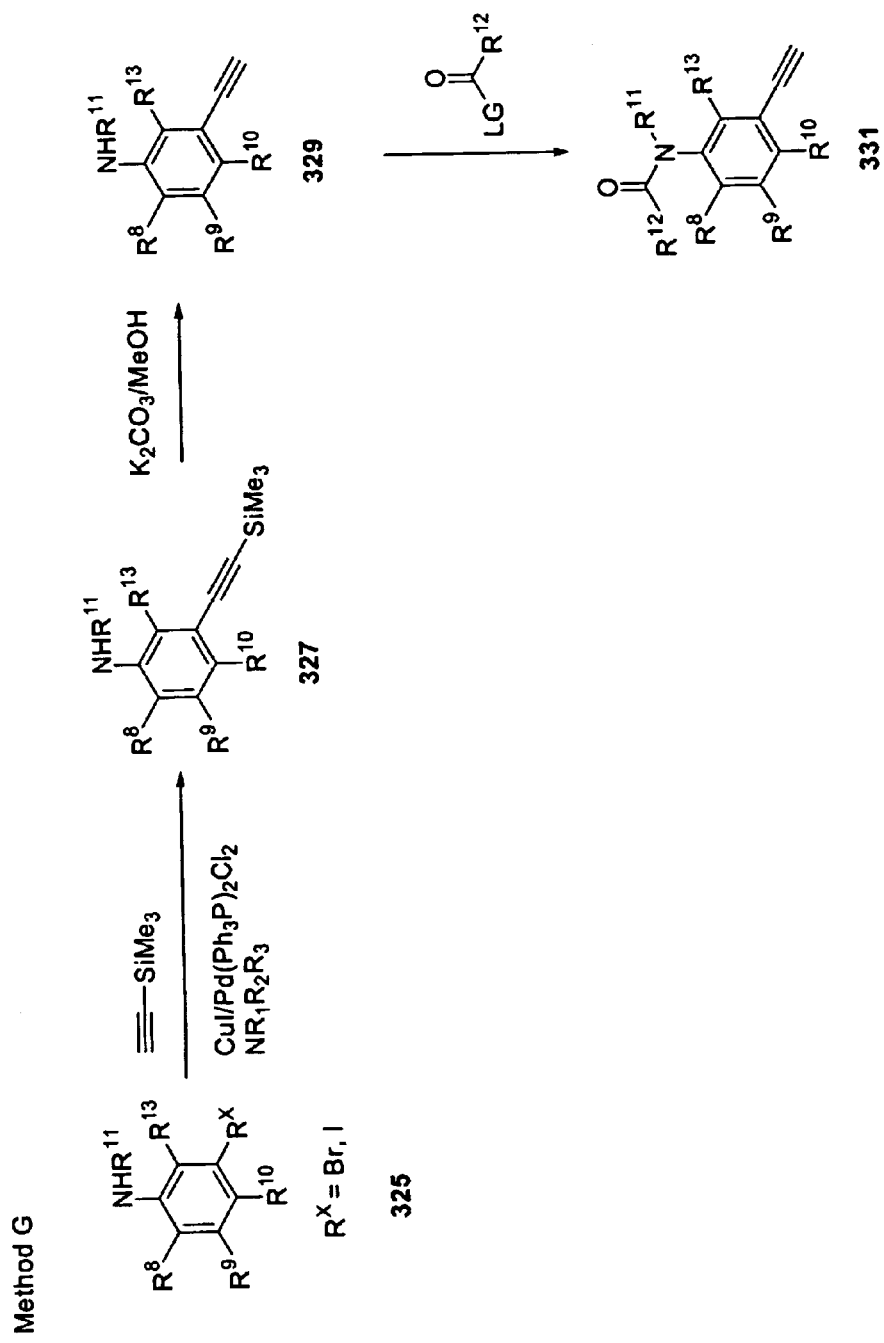

FIGS. 7A and 7B, which describe the preparation of acetylene compounds, are discussed in the Examples section.

In FIGS. 1–7, substituents $R^2$, $R^3$, $R^4$, $R^5$, $R^6$, $R^8$, $R^9$, $R^{10}$ and $R^{13}$ may include reactive functional groups that require protection during synthesis. Selection of suitable protecting groups will depend on the identity of the functional group and the synthesis method employed, and will be apparent to those of skill in the art. Guidance for selecting suitable protecting groups can be found in Greene & Wuts, supra, and the various other references cited therein.

Further guidance for carrying out 1,3-dipolar cycloaddition reactions, also named 1,3-dipolar additions, [3+2] cyclizations or [3+2] cycloadditions, can be found in "Cycloaddition Reactions in Organic Synthesis", (Kobayashi, S. and Jorgensen, K. A., Editors), 2002, Wiley-VCH Publishers, pp. 1–332 pages (specifically, Chapters 6 and 7 on [3+2] cycloadditions and 1,3-dipolar additions, pp. 211–248 and 249–300) "1,3-Dipolar Cycloaddition", *Chemistry of Heterocyclic Compounds*, Vol. 59, (Padwa, A. and Pearson, W., Editors), 2002, John Wiley, New York, pp. 1–940; "Nitrile Oxides, Nitrones, Nitronates in Organic Synthesis: Novel Strategies in Synthesis", Torssel, K. B. G., 1988, VCH Publishers, New York, pp. 1–332; Barnes & Spriggs, 1945, *J. Am. Chem Soc.* 67:134; and Anjaneyulu et al., 1995, *Indian J. Chem.*, Sect. 5 34(11):933–938).

Further guidance for synthesizing isoxozoles may be found in M. Sutharchanadevi, R. Murugan in *Comprehensive Heterocyclic Chemistry II*, A. R. Katritzky, C. W. Rees, E. F. V. Scriven, Eds.; Pergamon Press, Oxford, Vol. 3, p. 221; R. Grünager, P, Vita-Finzi in *Heterocyclic Compounds*, Vol. 49, *Isoxazoles, Part one*, John Wiley and Sons, New York, 1991; K. B. G. Torssell, *Nitrile Oxides, Nitrones, and Nitronates in Organic Synthesis*, VCH Publishers, New York, 1988; Y-Y. Ku, T. Grieme, P. Sharma, Y.-M. Pu, P. Raje, H. Morton, S. King *Organic Letters*, 2001, 3, 4185; V. G. Desai, S. G. Tilve *Synth. Comm.*, 1999, 29, 3017; X. Wei, J. Fang, Y. Hu, H. Hu *Synthesis*, 1992, 1205; C. Kashima, N. Yoshihara, S. Shirai *Heterocycles*, 1981, 16, 145; A. S. R. Anjaneyulu, G. S. Rani, K. G. Annapurna, U. V. Mallavadhani, Y. L. N. Murthy *Indian J. Chem. Sect B*, 1995, 34, 933; R. P. Barnes, A. S. Spriggs, *J. Am. Chem. Soc.*, 1945, 67, 134; A. Alberola, L. Calvo, A. G. Ortega, M. L. Sábada, M. C. Sañudo, S. G. Granda, E. G. Rodriguez *Heterocycles*, 1999, 51, 2675; X. Wang, J. Tan, K. Grozinger *Tetrahedron Lett.* 2000, 41, 4713; A. R. Katritzky, M. Wang, S. Zhang, M. V. Voronkov *J. Org. Chem.*, 2001, 66, 6787; and J. Bohrisch, M. Pätzel, C. Mügge, J. Liebscher *Synthesis*, 1991, 1153. Further guidance for synthesizing pyrazoles may be found in J. Elguero in *Comprehensive Heterocyclic Chemistry II*, A. R. Katritzky, C. W. Reees, E. F. V. Scriven., Eds.; Pergamon Press, Oxford, 1996; Vol. 3, p.1.

6.4 Assays for Modulation of HCV

The compounds of the invention are potent inhibitors of HCV replication and/or proliferation. The activity of the compounds of the invention can be confirmed in in vitro assays suitable for measuring inhibition of viral or retroviral replication and/or proliferation. The assays may investigate any parameter that is directly or indirectly under the influence of HCV, including, but not limited to, protein-RNA binding, translation, transcription, genome replication, protein processing, viral particle formation, infectivity, viral transduction, etc. Such assays are well-known in the art. Regardless of the parameter being investigated, in one embodiment, to examine the extent of inhibition, samples, cells, tissues, etc. comprising an HCV replicon or HCV RNA are treated with a potential inhibitory compound (test compound) and the value for the parameter compared to control cells (untreated or treated with a vehicle or other placebo). Control samples are assigned a relative activity value of 100%. Inhibition is achieved when the activity value of the test compound relative to the control is about 90%, preferably 50%, and more preferably 25–0%.

Alternatively, the extent of inhibition may be determined based upon the $IC_{50}$ of the compound in the particular assay, as will be described in more detail, below.

In one embodiment, the inhibitory activity of the compounds can be confirmed in a replicon assay that assesses the ability of a test compound to block or inhibit HCV replication in replicon cells. One example of a suitable replicon assay is the liver cell-line Huh 7-based replicon assay described in Lohmann et al., 1999, Science 285:110–113. A specific example of this replicon assay which utilizes luciferase translation is provided in the Examples Section. In one embodiment of this assay, the amount of test compound that yields a 50% reduction in translation as compared to a control cell ($IC_{50}$) may be determined.

Alternatively, the inhibitory activity of the compounds can be confirmed using a quantitative Western immunoblot assay utilizing antibodies specific for HCV non-structural proteins, such as NS3, NS4A NS5A and NS5B. In one embodiment of this assay, replicon cells are treated with varying concentrations of test compound to determine the concentration of test compound that yields a 50% reduction in the amount of a non-structural protein produced as compared to a control sample ($IC_{50}$). A single non-structural protein may be quantified or multiple non-structural proteins may be quantified. Antibodies suitable for carrying out such immunoblot assays are available commercially (e.g., from BIODESIGN International, Saco, Me.).

Alternatively, the inhibitory activity of the compounds may be confirmed in an HCV infection assay, such as the HCV infection assay described in Fournier et al., 1998, J. Gen. Virol. 79(10):2367:2374, the disclosure of which is incorporated herein by reference. In one embodiment of this assay, the amount of test compound that yields a 50% reduction in HCV replication or proliferation as compared to a control cell ($IC_{50}$) may be determined. The extent of HCV replication may be determined by quantifying the amount of HCV RNA present in HCV infected cells. A specific method for carrying out such an assay is provided in the Examples section.

As yet another example, the inhibitory activity of the compounds can be confirmed using an assay that quantifies the amount of HCV RNA transcribed in treated replicon cells using, for example, a Taqman assay (Roche Molecular, Alameda, Calif.). In one embodiment of this assay, the amount of test compound that yields a 50% reduction in transcription of one or more HCV RNAs as compared to a control sample ($IC_{50}$) may be determined.

Regardless of the assay used, active compounds are generally those which exhibit $IC_{50}$s in the particular assay in the range of about 1 mM or less. Compounds which exhibit lower $IC_{50}$s, for example, in the range of about 100 $\mu$M, 10 $\mu$M, 1 $\mu$M, 100 nM, 10 nM, 1 nM, or even lower, are particularly useful for as therapeutics or prophylactics to treat or prevent HCV infections.

6.5 Uses and Administration

Owing to their ability to inhibit HCV replication, the compounds of the invention and/or compositions thereof can be used in a variety of contexts. For example, the compounds of the invention can be used as controls in in vitro assays to identify additional more or less potent anti HCV compounds. As another example, the compounds of the invention and/or compositions thereof can be used as preservatives or disinfectants in clinical settings to prevent medical instruments and supplies from becoming infected with HCV virus. When used in this context, the compound of the invention and/or composition thereof may be applied to the instrument to be disinfected at a concentration that is a multiple, for example 1x, 2x, 3x, 4x, 5x or even higher, of the measured $IC_{50}$ for the compound.

In a specific embodiment, the compounds and/or compositions can be used to "disinfect" organs for transplantation. For example, a liver or portion thereof being prepared for transplantation can be perfused with a solution comprising an inhibitory compound of the invention prior to implanting the organ into the recipient. This method has proven successful with lamuvidine (3TC, Epivir®, Epivir-HB®) for reducing the incidence of hepatitis B virus (HBV) infection following liver transplant surgery/therapy. Quite interestingly, it has been found that such perfusion therapy not only protects a liver recipient free of HBV infection (HBV−) from contracting HBV from a liver received from an HBV+ donor, but it also protects a liver from an HBV− donor transplanted into an HBV+ recipient from attack by HBV. The compounds of the invention may be used in a similar manner prior to organ or liver transplantation.

The compounds of the invention and/or compositions thereof find particular use in the treatment and/or prevention of HCV infections in animals and humans. When used in this context, the compounds may be administered per se, but are typically formulated and administered in the form of a pharmaceutical composition. The exact composition will depend upon, among other things, the method of administration and will apparent to those of skill in the art. A wide variety of suitable pharmaceutical compositions are described, for example, in Remington's Pharmaceutical Sciences, 20$^{th}$ ed., 2001).

Formulations suitable for oral administration can consist of (a) liquid solutions, such as an effective amount of the active compound suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, subcutaneous administration and intravenous administration are the preferred methods of administration. A specific example of a suitable solution formulation may comprise from about 0.5–100 mg/ml compound and about 1000 mg/ml propylene glycol in water. Another specific example of a suitable solution formulation may comprise from about 0.5–100 mg/ml compound and from about 800–1000 mg/ml polyethylene glycol 400 (PEG 400) in water.

A specific example of a suitable suspension formulation may include from about 0.5–30 mg/ml compound and one or more excipients selected from the group consisting of: about 200 mg/ml ethanol, about 1000 mg/ml vegetable oil (e.g., corn oil), about 600–1000 mg/ml fruit juice (e.g., grapefruit juice), about 400–800 mg/ml milk, about 0.1 mg/ml carboxymethylcellulose (or microcrystalline cellulose), about 0.5 mg/ml benzyl alcohol (or a combination of benzyl alcohol and benzalkonium chloride) and about 40–50 mM buffer, pH 7 (e.g., phosphate buffer, acetate buffer or citrate buffer or, alternatively 5% dextrose may be used in place of the buffer) in water.

A specific example of a suitable liposome suspension formulation may comprise from about 0.5–30 mg/ml compound, about 100–200 mg/ml lecithin (or other phospholipid or mixture of phospholipids) and optionally about 5 mg/ml cholesterol in water. For subcutaneous administration of compound 9, a liposome suspension formulation including 5 mg/ml compound in water with 100 mg/ml lecithin and 5 mg/ml compound in water with 100 mg/ml lecithin and 5 mg/ml cholesterol provides good results. This formulation may be used for other compounds of the invention.

The formulations of compounds can be presented in unit-dose or multi-dose sealed containers, such as ampules and vials. Injection solutions and suspensions can be prepared from sterile powders, granules, and tablets of the kind previously described.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents, discussed in more detail, below.

In therapeutic use for the treatment of HCV infection, the compounds utilized in the pharmaceutical method of the invention are administered to patients diagnosed with HCV infection at dosage levels suitable to achieve therapeutic benefit. By therapeutic benefit is meant that the administration of compound leads to a beneficial effect in the patient over time. For example, therapeutic benefit is achieved when the HCV titer or load in the patient is either reduced or stops increasing. Therapeutic benefit is also achieved if the administration of compound slows or halts altogether the onset of the organ damage that or other adverse symptoms typically accompany HCV infections, regardless of the HCV titer or load in the patient.

The compounds of the invention and/or compositions thereof may also be administered prophylactically in patients who are at risk of developing HCV infection, or who have been exposed to HCV, to prevent the development of HCV infection. For example, the compounds of the invention and/or compositions thereof may be administered to hospital workers accidentally stuck with needles while working with HCV patients to lower the risk of, or avoid altogether, developing an HCV infection.

Initial dosages suitable for administration to humans may be determined from in vitro assays or animal models. For example, an initial dosage may be formulated to achieve a serum concentration that includes the $IC_{50}$ of the particular compound being administered, as measured in an in vitro assay. Alternatively, an initial dosage for humans may be based upon dosages found to be effective in animal models of HCV infection. Exemplary suitable model systems are described, for example, in Muchmore, 2001, Immunol. Rev. 183:86–93 and Lanford & Bigger, 2002, Virology, 293:1–9, and the referenced cited therein. As one example, the initial dosage may be in the range of about 0.01 mg/kg/day to about 200 mg/kg/day, or about 0.1 mg/kg/day to about 100 mg/kg/day, or about 1 mg/kg/day to about 50 mg/kg/day, or about 10 mg/kg/day to about 50 mg/kg/day, can also be used. The dosages, however, may be varied depending upon the requirements of the patient, the severity of the condition being treated, and the compound being employed. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

6.6 Combination Therapy

In certain embodiments of the present invention, the compounds of the invention and/or compositions thereof can be used in combination therapy with at least one other therapeutic agent. A compound of the invention and/or composition thereof and the therapeutic agent can act additively or, more preferably, synergistically. The compound of the invention and/or a composition thereof may be administered concurrently with the administration of the other therapeutic agent(s), or it may be administered prior to or subsequent to administration of the other therapeutic agent(s).

In one embodiment, the compounds of the invention and/or compositions thereof are used in combination therapy with other antiviral agents or other therapies known to be effective in the treatment or prevention of HCV. As a specific example, the compounds of the invention and/or compositions thereof may be used in combination with known antivirals, such as ribavirin (see, e.g., U.S. Pat. No. 4,530,901). As another specific example, the compounds of the invention and/or compositions thereof may also be administered in combination with one or more of the compounds described in any of the following: U.S. Pat. No. 6,143,715; U.S. Pat. No. 6,323,180; U.S. Pat. No. 6,329,379; U.S. Pat. No. 6,329,417; U.S. Pat. No. 6,410,531; U.S. Pat. No. 6,420,380; and U.S. Pat. No. 6,448,281.

Yet another specific example, the compounds of the invention and/or compositions thereof may be used in combination with interferons such as α-interferon, β-interferon and/or γ-interferon. The interferons may be unmodified, or may be modified with moieties such as polyethylene glycol (pegylated interferons). Many suitable unpegylated and pegylated interferons are available commercially, and include, by way of example and not limitation, recombinant interferon alpha-2b such as Intron-A interferon available from Schering Corporation, Kenilworth, N.J., recombinant interferon alpha-2a such as Roferon interferon available from Hoffmann-La Roche, Nutley, N.J., recombinant interferon alpha-2C such as Berofor alpha 2 interferon available from Bochringer Ingelheim Pharmaceutical, Inc., Ridgefield, Conn., interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain, or a consensus alpha interferon such as those described in U.S. Pat. Nos. 4,897,471 and 4,695,623 (especially Examples 7, 8 or 9 thereof) and the specific product available from Amgen, Inc., Newbury Park, Calif., or interferon alpha-n3 a mixture of natural alpha interferons made by Interferon Sciences and available from the Purdue Frederick Co., Norwalk, Conn., under the Alferon Tradename, pegylated interferon-2b available from Schering Corporation, Kenilworth, N.J. under the tradename PEG-Intron A and pegylated interferon-2a available from Hoffman-LaRoche, Nutley, N.J. under the tradename Pegasys.

As yet another specific example, the compounds of the invention and/or compositions thereof may be administered in combination with both ribovirin and an interferon.

7. EXAMPLES

The following examples are provided by way of illustration only and not by way of limitation. Those of skill in the art will readily recognize a variety of noncritical parameters that could be changed or modified to yield essentially similar results 7.1 Compound Syntheses The compounds of TABLE 1 were synthesized according to the methods described below or illustrated in FIGS. 1–7. Melting points were obtained on an Electrothermal IA9100 series digital melting point apparatus. All Melting points are uncorrected. NMR spectra were obtained on a 300 MHz Varian Mercury system. LC-MS was performed on a Waters Micromass ZQ instrument with electrospray ionization. The HPLC component was a Waters Model 2690 Separation module coupled to a Waters Model 996 photodiode array detector. The specific LC-MS method used to analyze particular compounds, indicated for each compound in parentheses, are provided below:

Method W

This method utilized a 2.1×250 mm 5 µM C-18 Altima reversed phase column (Alltech) with a flow rate of 0.25 mL/min and a gradient of 5–85% acetonitrile with water containing 0.1% trifluoroacetic acid over 36 min. The gradient then ramps to 100% acetonitrile over 0.5 min and continues at 100% acetonitrile for 3.5 min.

Method X

This method utilized a 2.1×250 mm 5 µM C-18 Altima reversed phase column (Alltech) with a flow rate of 0.25 mL/min and a gradient of 5–85% acetonitrile with water containing 0.1% trifluoroacetic acid over 15 min. The gradient then ramps to 100% acetonitrile over 0.5 min and continues at 100% acetonitrile for 2.5 min.

Method Y

This method utilized a 2.1×150 mm Agilent Zorbax 5 µM C-18 reversed phase column with a flow rate of 0.3 mL/min and a gradient of 10–100% acetonitrile with water containing 0.1% trifluoroacetic acid over 16 min, then continuing for 2 min with 100% acetonitrile.

Method Z

This method utilized a 2.1×5 mm Agilent Zorbax 5 µM C-18 reversed phase column with a flow rate of 0.5 mL/min and a gradient of 5–100% acetonitrile with water containing 0.1% trifluoroacetic acid over 8 min, then continuing for 2 min with 100% acetonitrile.

Synthesis of 2,2-Dichloro-N-[3-[3-(2,6-dichlorophenyl)-5-isoxazolyl]phenyl] Acetamide (Compound 9)

Synthesis of 2,6-Dichloro-N-hydroxybenzenecarboximidoyl Chloride

The general procedure of R. K. Howe et al, *J. Org. Chem.*, 1980, 45, 3916–3918 was followed. 2,6-Dichlorobenzaldoxime (25.1 gm, 0.132 mol) was dissolved in DMF (150 mL). Then N-chlorosuccinimide (approximately 1.5 g) was added. After several minutes the reaction was heated until the internal temperature reached 50° C. Then the remainder of the N-chlorosuccinimide was added in small portions to a total of 17.6 g (0.132 mol), keeping the reaction temperature at 40–50° C. After the addition was complete, the reaction was allowed to stir for 0.5 h, then was diluted with 600 mL of water. The mixture was extracted twice with ether. The combined ether extracts were washed three times with water, dried over anhydrous sodium sulfate, filtered and concentrated under reduced pressure. The residue was concentrated under vacuum to give the title α-chlorooxime as a white solid (m.p. 89–90° C). NMR (300 MHz, CDCl$_3$): 7.98 (s, 1H, exchanges with D$_2$O), 7.3–7.4 ppm (m, 3H).

Synthesis of 2,2-Dichloro-N-(3-ethynylphenyl) Acetamide

3-Ethynylaniline (2.61 g, 22.3 mmol) was dissolved in anhydrous dichloromethane (20 mL) with triethylamine (3.1 mL, 22.3 mmol). The mixture was cooled in an ice-bath under nitrogen, then a solution of dichloroacetyl chloride (2.21 mL, 23 mmol) in anhydrous dichloromethane (20 mL) was added dropwise. After the addition was completed the ice-bath was removed and the mixture was stirred at room temperature for 2 h. The reaction mixture was then washed successively with water, 10% hydrochloric acid and saturated sodium bicarbonate solution. The organic solution was dried over anhydrous sodium sulfate, filtered and concentrated under reduced pressure to give the title compound as a beige solid (m.p. 99–100° C.). NMR (300 MHz, CDCl$_3$): 8.05 (broad s, 1H, NH), 7.69 (s, 1H), 7.62 (m, 1H), 7.33 (m, 2H), 6.04 (s, 1H), 3.10 ppm (s, 1H, acetylenic).

Synthesis of 2,2-Dichloro-N-[3-[3-(2,6-dichlorophenyl)-5-isoxazolyl]phenyl] Acetamide (Compound 9)

2,6-Dichloro-N-hydroxybenzenecarboximidoyl chloride (2.72 g, 95.6 mmol) and 2,2-dichloro-N-(3-ethynylphenyl) acetamide (2.5 g, 110 mmol) were dissolved in anhydrous THF (40 mL) and triethylamine (1.8 mL). The mixture was stirred at room temperature for 1h then heated at reflux for 5 h to generate the 2,6-dichlorophenyl nitrile oxide intermediate, which reacted by a 1,3-dipolar cycloaddition reaction with 2,2-dichloro-N-(3-ethynylphenyl) acetamide. The solvent was removed under reduced pressure. The residue was dissolved in ethyl acetate and washed successively with water and brine. The ethyl acetate solution was dried over anhydrous sodium sulfate, filtered and concentrated under reduced pressure. The resulting solid was purified by column chromatography on silica gel, eluting with 8:2 hexanes-ethyl acetate. The appropriate fractions were combined and then crystallized from hexanes-ethyl acetate to give 2,2-dichloro-N-[3-[3-(2,6-dichlorophenyl)-5-isoxazolyl]phenyl] acetamide as a white crystalline solid, 1.80 g (m.p. 167° C.). NMR (300 MHz, CDCl$_3$): 8.21 (broad s, 1H, NH), 8.08 (m, 1H), 7.71 (m, 2H), 7.52 (t, 1H), 7.42–7.46 (m, 2H), 7.32–7.38 (m, 1H), 6.69 (s, 1H), 6.07 ppm (s, 1H). MW=416 confirmed by LC-MS, t$_r$=36.9 min (Method W) MH$^+$=415–419.

Oxime Formation (Step 1 of FIG. 3A)

Method A

Referring to FIG. 3A, the aldehyde starting material 245 was dissolved in pyridine solvent, and 1.0–1.2 equivalents of solid hydroxylamine hydrochloride was added in one portion and the homogeneous mixture was stirred overnight at room temperature. The mixture was concentrated under reduced pressure. The residue was dissolved in ethyl acetate and this solution was washed with either 1N hydrochloric acid followed by saturated brine, or by saturated brine alone. The ethyl acetate solution was then dried over anhydrous sodium sulfate, filtered and concentrated under reduced pressure to yield the desired oxime, 247.

Method B

By the general procedure of R. K. Howe, et al *J. Heterocyclic Chem.*, 1982, 19, 721–726 the aldehyde starting material 245 and a molar equivalent amount of hydroxylamine hydrochloride were dissolved in 30% aqueous methanol and stirred at 10–20° C. for 1 h. The solution was cooled to 0° C. for 1 h whereupon the solid oxime (not illustrated) precipitated. The solid oxime was then isolated by filtration followed by air-drying.

Method C

By the general procedure of R. K. Howe, et al, *J. Org. Chem.*, 1980, 45, 3916–3918 the aldehyde starting material 245 in 1:1 ethanol-water was treated with 1.1 equivalents of hydroxylamine hydrochloride and 2.5 equivalents of aqueous sodium hydroxide with cooling. The mixture was then stirred at room temperature for 1 h. The reaction mixture was extracted with ether, which was discarded and the aqueous layer was separated and acidified to pH 6 with concentrated hydrochloric acid with cooling. The aqueous layer was extracted with ether and the ether layers were separated. The combined ether layers were dried over anhydrous sodium sulfate, filtered and concentrated under reduced pressure to yield the desired solid oximes.

α-Chlorooxime Formation (Step 2 of FIG. 3A; Compound 247)

Method D

Again referring to FIG. 3A, the general procedure described by R. K. Howe, et al, *J. Org. Chem.*, 1980, 45, 3916–3918 was followed. The oxime was dissolved in DMF and 0.1 molar equivalent of N-chlorosuccinimide was added and the mixture was heated to 50° C. to initiate the reaction. The remaining 0.9 molar equivalent of N-chlorosuccinimide was added in small portions keeping the reaction temperature under 50° C. After the addition was completed, the mixture was stirred for 0.5 h and then diluted with water. The mixture was extracted with ether and the combined ether extracts were washed with water and brine. The ether layer was dried over anhydrous sodium sulfate, filtered and concentrated under reduced pressure to yield the desired α-chlorooxime 247.

Method E

The general procedure described by R. K. Howe, et al, *J. Org. Chem.*, 1980, 45, 3916–3918 was followed. The oxime was dissolved in DMF and 0.1 molar equivalent of N-chlorosuccinimide was added and the mixture was heated to 50° C. to initiate the reaction. The remaining 0.9 molar equivalent of N-chlorosuccinimide was added in small portions keeping the reaction temperature under 50° C. After the addition was complete the mixture was stirred for 3 h at room temperature. The resulting DMF solution containing the desired α-chlorooxime 247 was used immediately in the next step.

General Procedures for the Preparation of 2-Haloor 2,2-Dihalo-N-(3-ethynylphenyl) Acetamides (FIGS. 7A & 7B)

Method F (FIG. 7A)

Step 1. Acetylenic Cross-Coupling Reactions

Referring to FIG. 7A, the appropriately substituted m-bromonitrobenzene 315 or substituted m-iodonitrobenzene was dissolved in a suitable solvent such as p-dioxane or THF and then treated with at least five molar equivalents of a suitable amine base, which could be triethylamine, diethylamine or diisopropylethylamine. Alternatively, the amine base alone could be used as the solvent. A stream of argon gas was then bubbled through the solution for several minutes, followed by the addition of dichlorobis(triphenylphosphine) palladium (II) (3–4 mole percent), CuI (6–8 mole percent) and finally trimethylsilylacetylene (1.2–1.3 molar equivalents). The reaction mixture was then heated at 50–80° C. until the reaction was complete, as monitored by TLC or LC-MS. When the more reactive substituted m-iodonitrobenzenes were used, the acetylenic cross-coupling reaction could be performed at room temperature. If the reaction appeared sluggish, additional trimethylsilylacetylene was added. This general procedure is known in the literature as the Sonogashira coupling (K. Sonogashira et. al., *Tetrahedron Lett.*, 1975, 4467). The reaction mixture was then diluted with ethyl acetate and this solution was washed several times with brine. Alternatively, the crude reaction mixture was filtered over a pad of Celite, then diluted with ethyl acetate and washed with brine. The organic layer so obtained was dried over anhydrous sodium sulfate, filtered and concentrated to dryness under reduced pressure. The residue was purified by column chromatography on silica gel, eluting with mixtures of ethyl acetate and hexanes to give the desired substituted m-(trimethylsilylethynyl) nitrobenzenes 317.

Step 2. Reduction of the Nitro Group to Amines

The substituted m-(trimethylsilylethynyl) nitrobenzene 317 prepared in Step 1 was dissolved in a mixture of 10–15 volume percent of concentrated hydrochloric acid in methanol. Then, iron powder (Aldrich Chemical Co.) (5–10 molar equivalents) was added and the mixture was heated at 70–80° C. for 3–4 h. This reaction can be highly exothermic when performed on a large scale. After cooling to room temperature, the reaction mixture was filtered over Celite and the filtrate was concentrated under reduced pressure. The residue was dissolved in ethyl acetate and then carefully washed with either aqueous sodium hydroxide or aqueous sodium bicarbonate solution. The aqueous layer was discarded and the organic layer was washed with brine, dried over anhydrous sodium sulfate, filtered and concentrated to dryness under reduced pressure. If necessary the crude product could be purified by column chromatography on silica gel, eluting with mixtures of hexanes and ethyl acetate to give the desired substituted m-(trimethylsilylethynyl) anilines 319.

Step 3. Removal of the Trimethylsilyl Group from the Acetylenes

The substituted m-(trimethylsilylethynyl) aniline 319 prepared in Step 2 was dissolved in methanol containing 2–5% water. If the solubility of the aniline in methanol was poor, an appropriate amount of tetrahydrofuran (THF) was used as a co-solvent. Then anhydrous potassium carbonate (1 molar equivalent) was added and the mixture was stirred at room temperature for 1–24 h until the reaction was complete by TLC analysis. The reaction mixture was concentrated under reduced pressure and the residue was dissolved in ethyl acetate and washed with brine. The organic layer was dried over anhydrous sodium sulfate, filtered and concentrated under reduced pressure. The substituted m-aminophenylacetylenes 321 could be purified by column chromatography on silica gel, eluting with hexanes and ethyl acetate, if necessary.

Step 4. Introduction of the Haloacetamide or Dihaloacetamide Side Chains

The substituted m-aminophenylacetylene 321 prepared in Step 3 was dissolved in dichloromethane. Triethylamine (1.3 molar equivalents) was added and the solution was cooled in an ice-bath under nitrogen. Then a solution of acetylating reagent LG—C(O)—R$^{12}$ (e.g, haloacetyl chloride or dihaloacetyl chloride; 1.0 molar equivalent) in dichloromethane was added dropwise. After the addition was complete, the reaction was allowed to stir 0.5–1 h at 0° C. and then allowed to warm to room temperature. After a total of 1–4 h reaction time the reaction mixture was diluted with water. The organic layer was separated and further washed with saturated aqueous sodium bicarbonate solution and brine. The organic layer was dried over anhydrous sodium sulfate, filtered and concentrated under reduced pressure to give the substituted acetamide compound 323.

Alternatively, the substituted m-aminophenylacetylene 321 starting material was dissolved in dichloromethane and treated successively with 1-(3-dimethylaminopropyl)-3-ethylcarbodiimide hydrochloride (1 molar equivalent), a compound of the formula R$^{12}$—C(O)OH (e.g., a halo- or dihaloacetic acid; 1 molar equivalent) and finally triethylamine (1 molar equivalent). The reaction mixture was then stirred at room temperature until the substituted m-aminophenylacetylene starting material 321 was consumed as determined by TLC analysis. The mixture was washed with water and the organic layer was dried over anhydrous sodium sulfate, filtered and concentrated to dryness under reduced pressure to give the acetamide 323.

Method G (FIG. 7B)

Referring to FIG. 7B, an appropriately substituted m-iodoaniline or m-bromoaniline starting material 325 was coupled with trimethylsilylacetylene as described in Step 1 of Method F. The resulting substituted m-(trimethylsilylethynyl) aniline 327 was then deprotected using the procedure described in Step 3 of Method F to give the substituted m-aminophenylacetylene 329 which was then converted to the desired acetamide 331 as described in Step 4 of Method F.

1,3-Dipolar Cycloaddition Reactions to make Isoxazoles (FIG. 3A; 247→211)

Method H

Referring again to FIG. 3A, the α-chlorooxime 247 and 1.0 molar equivalent of the appropriate phenylacetylene were dissolved in either anhydrous THF or DMF and 1.3 molar equivalents of triethylamine was added. The α-chlorooxime immediately reacted with triethylamine to produce the corresponding phenyl nitrile oxide intermediate (248a or 248b) and also produced a precipitate of triethylamine hydrochloride. The heterogeneous mixture was then heated at 70–80° C. for 3–6 h to induce the 1,3-dipolar cycloaddition reaction of the phenyl nitrile oxide with the phenylacetylene 249. The solvent was removed by concentration under reduced pressure. The residue was dissolved in ethyl acetate and this solution was washed with aqueous sodium bicarbonate solution followed by water and brine. The ethyl acetate layers were dried over anhydrous sodium sulfate, filtered and concentrated under reduced pressure to yield the crude product 211. This material was further purified by column chromatography on silica gel, eluting with hexanes-ethyl acetate or by HPLC chromatography on a C-18 reversed phase column (mobile phase acetonitrile-water-trifluoroacetic acid). The isolated isoxazoles 211 were either crystallized or characterized as solids by spectral analysis.

In the same manner, the compounds listed below were made from the corresponding α-chlorooximes and the corresponding phenylacetylenes (the structures of the compounds are provided in TABLE 1).

Compound 1: 2,2-Dichloro-N-[3-[3-(2,6-dichlorophenyl)-5-isoxazolyl]-6-fluorophenyl] Acetamide; MW=434 confirmed by LC-MS, t$_r$=37.75 min (Method W) MH$^+$=433–437

Compound 3: 2,2-Dichloro-N-[3-[3-(2,3-dichlorophenyl)-5-isoxazolyl]phenyl] Acetamide; MW=412 confirmed by LC-MS, t$_r$=38.96 min (Method W) MH$^+$=411–415

Compound 5: 2,2-Dichloro-N-[3-[5-(2,6-dichlorophenyl)-3-isoxazolyl]phenyl] Acetamide; MW=416 confirmed by LC-MS, t$_r$=37.92 min (Method W) MH$^+$=415–419

Compound 7: 2,2-Dichloro-N-[3-[3-[2-chloro-6-(N-morpholino)phenyl]-5-isoxazolyl]phenyl] Acetamide; MW=462 confirmed by LC-MS, t$_r$=35.50 min (Method W) MH$^+$=461–465

Compound 9: 2,2-Dichloro-N-[3-[3-(2,6-dichlorophenyl)-5-isoxazolyl]phenyl] Acetamide; MW=416 confirmed by LC-MS, t$_r$=36.90 min (Method W) MH$^+$=415–419

Compound 11: 2,2-Dichloro-N-[3-[3-(2-fluoro-6-thiomethylphenyl)-5-isoxazolyl]phenyl] Acetamide; MW=411 confirmed by LC-MS, t$_r$=35.96 min (Method W) MH$^+$=410–414

Compound 13: 2,2-Dichloro-N-[3-[3-(2,6-dichlorophenyl)-5-isoxazolyl]-4-fluorophenyl] Acetamide; MW=434 confirmed by LC-MS, t$_r$=38.82 min (Method W) MH$^+$=433–437

Compound 15: 2,2-Dichloro-N-[3-[3-(2-chloro-6-fluoro-3-methylphenyl)-5-isoxazolyl]phenyl] Acetamide; MW=414 confirmed by LC-MS, t$_r$=28.91 min (Method X) MH$^+$=413–417

Compound 21: 2,2-Dichloro-N-[3-[3-[2-fluoro-(6-N-morpholinosulfamoyl)phenyl]-5-isoxazolyl]-phenyl] Acetamide; MW=514 confirmed by LC-MS, t$_r$=32.30 min (Method W) MH$^+$=513–517

Compound 23: 2,2-Dichloro-N-[3-[3-[2,6-dimethyl-4-(N-morpholino-2-ethyleneoxy)phenyl]-5-isoxazolyl]phenyl] Acetamide; MW=543 confirmed by LC-MS, t$_r$=27.59 min (Method X) MH$^+$=542–546

Compound 25: 2,2-Dichloro-N-[3-[3-(2,6-dichlorophenyl)-5-(1,2,4-oxadiazolyl)]phenyl] Acetamide; MW=417 confirmed by LC-MS, t$_r$=20.70 min (Method X) MH$^+$=416–420

Compound 27: 2,2-Dichloro-N-[3-[3-(2-chloro-6-fluorophenyl)-5-isoxazolyl]phenyl] Acetamide; MW=400 confirmed by LC-MS, t$_r$=35.94 min (Method W) MH$^+$=399–403

Compound 29: 2,2-Dibromo-N-[3-[3-(2,6-dichlorophenyl)-5-isoxazolyl]phenyl] Acetamide; MW=505 confirmed by LC-MS, t$_r$=33.30 min (Method W) MH$^+$=503–507

Compound 31: 2,2-Dichloro-N-[3-[3-(2-chloro-6-methylphenyl)-5-isoxazolyl]phenyl] Acetamide; MW=396 confirmed by LC-MS, t$_r$=33.26 min (Method W) MH$^+$=393–397

Compound 33: 2,2-Dichloro-N-[3-[3-(2-trifluoromethylphenyl)-5-isoxazolyl]phenyl] Acetamide; MW=415 confirmed by LC-MS, t$_r$=32.10 min (Method W) MH$^+$=414–418

Compound 35: 2,2-Dichloro-N-[3-[3-(2-hydroxy-6-trifluoromethylphenyl)-5-isoxazolyl]phenyl] Acetamide; MW=431 confirmed by LC-MS, t$_r$=13.80 min (Method Y) MH$^+$=430–434

Compound 37: 2,2-Dichloro-N-[3-[3-[2-(N-morpholino)-6-trifluoromethylphenyl)-5-isoxazolyl]phenyl] Acetamide; MW=500 confirmed by LC-MS, t$_r$=36.23 min (Method W) MH$^+$=499–503

Compound 39: 2,2-Dichloro-N-[3-[3-(2-chloro-6-isopropylphenyl)-5-isoxazolyl]phenyl] Acetamide; MW=424 confirmed by LC-MS, $t_r$=21.72 min (Method X) MH$^+$=423–427

Compound 41: 2,2-Dichloro-N-[3-[3-(2-fluoro-6-trifluoromethylphenyl)-5-isoxazolyl]phenyl] Acetamide; MW=433 confirmed by LC-MS, $t_r$=21.05 min (Method Y) MH$^+$=432–436

Compound 43: 2,2-Dichloro-N-[3-[3-(2-fluoro-6-methoxyphenyl)-5-isoxazolyl]phenyl] Acetamide; MW=395 confirmed by LC-MS, $t_r$=34.73 min (Method W) MH$^+$=494–498

Compound 45: 2,2-Dichloro-N-[3-[3-(2-difluoromethoxyphenyl)-5-isoxazolyl]phenyl] Acetamide; MW=413 confirmed by LC-MS, $t_r$=7.48 min (Method Z) MH$^+$=412–416

Compound 47: 2,2-Dichloro-N-[3-[3-(2,6-dimethylphenyl)-5-isoxazolyl]phenyl] Acetamide; MW=375 confirmed by LC-MS, $t_r$=20.69 min (Method X) MH$^+$=373–378

Compound 49: 2,2-Dichloro-N-[3-[3-(2-fluoro-6-iodophenyl)-5-isoxazolyl]phenyl] Acetamide; MW=491 confirmed by LC-MS, $t_r$=37.19 min (Method W) MH$^+$=490–494

Compound 51: 2,2-Dichloro-N-[3-[3-(6-chloro-2-fluoro-3-methylphenyl)-5-isoxazolyl]phenyl] Acetamide; MW=414 confirmed by LC-MS, $t_r$=38.16 min (Method W) MH$^+$=413–417

Compound 53: 2,2-Dichloro-N-[3-[3-(2-chloro-3,6-difluorophenyl)-5-isoxazolyl]phenyl] Acetamide; MW=418 confirmed by LC-MS, $t_r$=21.25 min (Method Y) MH$^+$=417–421

Compound 57: 2,2-Dicbloro-N-[3-[3-(2,6-dichlorophenyl)-5-isoxazolyl]phenyl]-N-methyl Acetamide; MW=430 confirmed by LC-MS, $t_r$=20.70 min (Method X) MH$^+$=429–433

Compound 61: 2,2-Dichloro-N-[3-[3-(2-ethoxyphenyl)-5-isoxazolyl]phenyl] Acetamide; MW=391 confirmed by LC-MS, $t_r$=7.66 min (Method Z) MH$^+$=390–394

Compound 63: 2,2-Dichloro-N-[3-[3-(2-isopropylphenyl)-5-isoxazolyl]phenyl] Acetamide; MW=389 confirmed by LC-MS, $t_r$=35.37 min (Method W) MH$^+$=388–392

Compound 65: 2,2-Dichloro-N-[3-[3-(2,6-dichloro-4-dimethylaminophenyl)-5-isoxazolyl]phenyl] Acetamide; MW=496 confirmed by LC-MS, $t_r$=40.10 min (Method W) MH$^+$=495–499

Compound 67: 2-Chloro-N-[3-[3-(2,6-dichlorophenyl)-5-isoxazolyl]phenyl] Acetamide; MW=382 confirmed by LC-MS, $t_r$=34.27 min (Method W) MH$^+$=379–383

Compound 69: 2,2-Dichloro-N-[3-[3-(2,4,6-trimethylphenyl)-5-isoxazolyl]phenyl] Acetamide; MW=389 confirmed by LC-MS, $t_r$=38.76 min (Method W) MH$^+$=388–392

Compound 73: 2,2-Dichloro-N-[3-[3-[2,6-dichloro-4-(N-morpholinopropyleneoxy)phenyl]-5-isoxazolyl]-phenyl] Acetamide; MW=559 confirmed by LC-MS, $t_r$=27.30 min (Method W) MH$^+$=558–562

Compound 75: 2,2-Dichloro-N-[3-[3-[2,6-dichloro-4-(N-morpholinoethyleneoxy)phenyl]-5-isoxazolyl]-phenyl] Acetamide; MW=545 confirmed by LC-MS, $t_r$=26.10 min (Method W) MH$^+$=544–548

Compound 77: 2,2-Dichloro-N-[3-[3-(2-methoxy-6-trifluoromethylphenyl)-5-isoxazolyl]phenyl] Acetamide; MW=445 confirmed by LC-MS, $t_r$=35.02 min (Method W) MH$^+$=444–448

Compound 79: 2,2-Dichloro-N-[3-[3-(2-chloro-6-cyclopropylphenyl)-5-isoxazolyl]phenyl] Acetamide; MW=422 confirmed by LC-MS, $t_r$=38.28 min (Method W) MH$^+$=421–425

Compound 81: 2,2-Dichloro-N-[3-[3-(2-chloro-6-methoxyphenyl)-5-isoxazolyl]phenyl] Acetamide; MW=412 confirmed by LC-MS, $t_r$=34.75 min (Method W) MH$^+$=411–415

Compound 83: 2,2-Dichloro-N-[3-[3-(2-chloro-6-hydroxyphenyl)-5-isoxazolyl]phenyl] Acetamide; MW=398 confirmed by LC-MS, $t_r$=18.04 min (Method X) MH$^+$=397–401

Compound 85: 2,2-Dichloro-N-[3-[3-(2-methyl-6-trifluoromethylphenyl)-5-isoxazolyl]phenyl] Acetamide; MW=429 confirmed by LC-MS, $t_r$=18.83 min (Method X) MH$^+$=428–432

Compound 87: 2,2-Dichloro-N-[3-[5-(2,6-dichlorophenyl)-3-(1,2,4-oxadiazolyl)]phenyl] Acetamide; MW=417 confirmed by LC-MS, $t_r$=18.30 min (Method X) MH$^+$+Na= 439–443

Compound 89: 2,2-Dichloro-N-[3-[3-(2-cyclopropyl-6-trifluoromethylphenyl)-5-isoxazolyl]phenyl] Acetamide; MW=455 confirmed by LC-MS, $t_r$=19.45 min (Method X) MH$^+$=454–458

Compound 91: 2,2-Dichloro-N-[3-[3-(2-methoxy-6-methylphenyl)-5-isoxazolyl]phenyl] Acetamide; MW=391 confirmed by LC-MS, $t_r$=34.99 min (Method W) MH$^+$=390–394

Compound 93: 2,2-Dichloro-N-[3-[3-(2-isopropyl-6-trifluoromethylphenyl)-5-isoxazolyl]phenyl] Acetamide; MW=457 confirmed by LC-MS, $t_r$=18.11 min (Method X) MH$^+$=456–460

Compound 95: 2,2-Dichloro-N-[3-[3-[2-chloro-6-(N-morpholino-2-ethyleneoxy)phenyl]-5-isoxazolyl]-phenyl] Acetamide; MW=511 confirmed by LC-MS, $t_r$=10.49 min (Method Y) MH$^+$=510–514

Compound 97: 2,2-Dichloro-N-[3-[3-(2-chloro-6-cyclopentylphenyl)-5-isoxazolyl]phenyl] Acetamide; MW=450 confirmed by LC-MS, $t_r$=22.35 min (Method X) MH$^+$=449–453

Compound 99: 2,2-Dichloro-N-[3-[3-[2-chloro-6-(4-methylpiperazino)phenyl]-5-isoxazolyl]phenyl] Acetamide; MW=480 confirmed by LC-MS, $t_r$=25.83 min (Method W) MH$^+$=479–483

Compound 101: 2-Iodo-N-[3-[3-(2,6-dichlorophenyl)-5-isoxazolyl]phenyl] Acetamide; MW=473 confirmed by LC-MS, $t_r$=35.62 min (Method W) MH$^+$=472–476

Compound 103: 2,2-Dichloro-N-[3-[3-(2-chloro-6-n-butylphenyl)-5-isoxazolyl]phenyl] Acetamide; MW=438 confirmed by LC-MS, $t_r$=22.15 min (Method X) MH$^+$=437–441

Compound 105: 2,2-Dichloro-N-[3-[3-(2-cyclopentyl-6-trifluoromethylphenyl)-5-isoxazolyl]phenyl] Acetamide; MW=383 confirmed by LC-MS, $t_r$=37.74 min (Method W) MH$^+$=382–386

Compound 107: 2,2-Dichloro-N-[3-[3-(2,6-dichlorophenyl)-5-isoxazolyl]-4-(N-morpholinosulfamoyl)-phenyl] Acetamide; MW=565 confirmed by LC-MS, $t_r$=32.23 min (Method W) MH$^+$=564–568

Compound 109: 2,2-Dichloro-N-[3-[3-[2-trifluoromethyl-6-(4-methylpiperazino)phenyl]-5-isoxazolyl]-phenyl] Acetamide; MW=513 confirmed by LC-MS, $t_r$=26.18 min (Method W) MH$^+$=512–516

Compound 111: 2,2-Dichloro-N-[3-[3-(2-chloro-6-cyclohexylphenyl)-5-isoxazolyl]phenyl] Acetamide; MW=464 confirmed by LC-MS, $t_r$=22.70 min (Method W) MH$^+$=463–467

Compound 113: 2,2-Dichloro-N-[3-[3-(2-trifluoromethoxyphenyl)-5-isoxazolyl]phenyl] Acetamide; MW=431 confirmed by LC-MS, $t_r$=34.26 min (Method W) MH$^+$=430–434

Compound 115: 2,2-Dichloro-N-[3-[3-(2-carbomethoxy) phenyl-5-isoxazolyl]phenyl] Acetamide; MW=405 confirmed by LC-MS, $t_r$=7.08 min (method z) MH$^+$=404–408

Compound 117: 2,2-Dichloro-N-[3-[3-[2-chloro-6-(N-imidazolyl)phenyl]-5-isoxazolyl]phenyl] Acetamide; MW=448 confirmed by LC-MS, $t_r$=24.72 min (Method W) MH$^+$=447–451

Compound 119: 2,2-Dichloro-N-[3-[3-(2-isopropyloxyphenyl)-5-isoxazolyl]phenyl] Acetamide; MW=405 confirmed by LC-MS, $t_r$=34.78 min (Method W) MH$^+$=404–408

Compound 121: 2,2-Dichloro-N-[3-[3-(2,6-diisopropylphenyl)-5-isoxazolyl]phenyl] Acetamide; MW=431 confirmed by LC-MS, $t_r$=22.32 min (Method X) MH$^+$=430–434

Compound 123: 2,2-Dichloro-N-[3-[3-(2-phenyl)phenyl-5-isoxazolyl]phenyl] Acetamide; MW=424 confirmed by LC-MS, $t_r$=21.48 min (Method X) MH$^+$=423–427

Compound 125: 2,2-Dichloro-N-[3-[3-[2,6-dichloro-4-(N-piperidinylethylenoxy) phenyl]-5-isoxazolyl]-phenyl] Acetamide; MW=543 confirmed by LC-MS, $t_r$=27.59 min (Method W) MH$^+$=542–546

Compound 121: 2,2-Dichloro-N-[3-[3-(2,6-dichlorophenyl)-5-isoxazolyl]-4-methoxyphenyl] Acetamide; MW=446 confirmed by LC-MS, $t_r$=36.71 min (Method W) MH$^+$=445–449

Compound 129: 2,2-Dichloro-N-[3-[3-(2-cyclopentylphenyl)-5-isoxazolyl]phenyl] Acetamide; MW=415 confirmed by LC-MS, $t_r$=22.24 min (Method X) MH$^+$=414–418

Compound 131: 2-Dichloro-N-[3-[3-[2-chloro-6-(N,N-dimethylethylene-N'-methylamino)phenyl]-5-isoxazolyl]-phenyl] Acetamide; MW=482 confirmed by LC-MS, $t_r$=26.06 min (Method W) MH$^+$=481–485

Compound 132: (±)-2,2-Dichloro-N-[3-[3-[2-chloro-6-(3-dimethylamino-N-pyrrolidino)phenyl]-5-isoxazolyl]-phenyl] Acetamide; MW=494 confirmed by LC-MS, $t_r$=30.00 min (Method W) MH$^+$=493–497

Compound 135: 2,2-Dichloro-N-[3-[3-(3-carbomethoxy-2,6-dichlorophenyl)-5-isoxazolyl]phenyl] Acetamide; MW=474 confirmed by LC-MS, $t_r$=35.61 min (Method W) MH$^+$=473–477

Compound 137: 2,2-Dichloro-N-[3-[3-(2,3,6-trichlorophenyl)-5-isoxazolyl]phenyl] Acetamide; MW=451 confirmed by LC-MS, $t_r$=28.75 min (Method X) MH$^+$=450–454

Compound 139: 2,2-Dichloro-N-[3-[3-(3-carboxy-2,6-dichlorophenyl)-5-isoxazolyl]phenyl] Acetamide; MW=460 confirmed by LC-MS, $t_r$=31.46 min (Method W) MH$^+$=459–463

Compound 141: 2,2-Dichloro-N-[3-[3-(2-chloro-5-trifluoromethylphenyl)-5-isoxazolyl]phenyl] Acetamide; MW=450 confirmed by LC-MS, $t_r$=22.11 min (Method X) MH$^+$=449–453

Compound 143: 2,2-Dichloro-N-[3-[3-[2,4-dichloro-6-(N-morpholino-2-ethyleneoxy)phenyl]-5-isoxazolyl]-phenyl] Acetamide; MW=545 confirmed by LC-MS, $t_r$=28.25 min (Method X) MH$^+$=544–548

Compound 145: 2,2-Difluoro-N-[3-[3-(2,6-dichlorophenyl)-5-isoxazolyl]phenyl] Acetamide; MW=383 confirmed by LC-MS, $t_r$=35.58 min (Method W) MH$^+$=382–386

Compound 149: 2,2-Dichloro-N-[3-[3-(2,6-difluoro-3-methylphenyl)-5-isoxazolyl]phenyl] Acetamide; MW=397 confirmed by LC-MS, $t_r$=37.13 min (Method W) MH$^+$=396–400

Compound 151: 2,2-Dichloro-N-[3-[3-[2-chloro-6-(4-carboethoxypiperidino)phenyl]-5-isoxazolyl]-phenyl] Acetamide; MW=537 confirmed by LC-MS, $t_r$=39.98 min (Method W) MH$^+$=536–540

Compound 153: 2,2-Dichloro-N-[3-[3-(2-fluoro-6-methylsulfonyl)phenyl-5-isoxazolyl]phenyl] Acetamide; MW=443 confirmed by LC-MS, $t_r$=6.62 min (method z) MH$^+$=441–445

Compound 155: 2,2-Dichloro-N-[3-[3-[2-(N-morpholinomethyl)phenyl]-5-isoxazolyl]phenyl] Acetamide; MW=446 confirmed by LC-MS, $t_r$=23.63 min (Method W) MH$^+$=445–449

Compound 157: 2,2-Dichloro-N-[3-[3-(2-carboxyphenyl)-5-isoxazolyl]phenyl] Acetamide; MW=391 confirmed by LC-MS, $t_r$=6.40 min (Method Z) MH$^+$=390–394

Compound 159: 2,2-Dichloro-N-[3-[3-(2,4-dichlorophenyl)-5-isoxazolyl]phenyl] Acetamide Compound 161: 2,2-Dichloro-N-[3-[3-(2-benzyloxyphenyl)-5-isoxazolyl]phenyl] Acetamide; MW=453 confirmed by LC-MS, $t_r$=39.69 min (Method W) MH$^+$=452–456

Compound 163: 2,2-Dichloro-N-[3-[3-(2,3-dimethylphenyl)-5-isoxazolyl]phenyl] Acetamide; MW=375 confirmed by LC-MS, $t_r$=37.62 min (Method W) MH$^+$=374–378

Compound 165: 2,2-Dichloro-N-[3-[3-(2,6-dichlorophenyl)-5-isoxazolyl]-6-methylphenyl] Acetamide; MW=430 confirmed by LC-MS, $t_r$=36.48 min (Method W) MH$^+$=429–433

Compound 167: 2,2-Dichloro-N-[3-[3-(2,6-dichlorophenyl)-5-isoxazolyl]-2-methylphenyl] Acetamide; MW=430 confirmed by LC-MS, $t_r$=35.85 min (Method W) MH$^+$=429–433

Compound 169: 2,2-Dichloro-N-[3-[3-(2,6-dichlorophenyl)-5-isoxazolyl] [6-(N-morpholino)phenyl] Acetamide; MW=501 confirmed by LC-MS, $t_r$=39.10 min (Method W) MH$^+$=500–504

Compound 171: 2,2-Dichloro-N-[3-[3-(2,6-dichlorophenyl)-5-isoxazolyl]-6-(N-morpholino-2-ethyleneoxy)phenyl]Acetamide; MW=545 confirmed by LC-MS, $t_r$=27.77 min (Method W) MH$^+$=544–548

Compound 173: 2,2-Dichloro-N-[3-[3-(2,6-dichlorophenyl)-5-isoxazolyl]-6-methoxyphenyl] Acetamide; MW=446 confirmed by LC-MS, $t_r$=20.80 min (Method X) MH$^+$=445–449

Compound 175: 2,2-Dichloro-N-[3-[3-[2-chloro-6-[4-(N-piperidinyl)-N-piperidinyl]phenyl]-5-isoxazolyl]phenyl] Acetamide; MW=548 confirmed by LC-MS, $t_r$=27.95 min (Method W) MH$^+$=547–551

Compound 177: 2,2-Dichloro-N-[3-[3-(2-chlorophenyl)-5-isoxazolyl]phenyl] Acetamide; MW=382 confirmed by LC-MS, $t_r$=15.45 min (Method Y) MH$^+$=381–385

Compound 179: 2,2-Dichloro-N-[3-[3-(2-bromophenyl)-5-isoxazolyl]phenyl] Acetamide; MW=426 confirmed by LC-MS, $t_r$=15.59 min (Method Y) MH$^+$=425–429

Compound 181: 2,2-Dichloro-N-[3-[3-(2-chloro-6-nitrophenyl)-5-isoxazolyl]phenyl] Acetamide; MW=426 confirmed by LC-MS, $t_r$=14.47 min (Method Y) MH$^+$=425–429

Compound 183: 2,2-Dichloro-N-[3-[3-(2-methoxyphenyl)-5-isoxazolyl]phenyl] Acetamide; MW=377 confirmed by LC-MS, $t_r$=14.90 min (Method Y) MH$^+$=376–380

Compound 185: 2,2-Dichloro-N-[3-[3-(2-bromo-6-chlorophenyl)-5-isoxazolyl]phenyl] Acetamide; MW=461 confirmed by LC-MS, $t_r$=15.58 min (Method Y) MH$^+$=460–464

Compound 187: 2,2-Dichloro-N-[3-[3-(2-chloro-6-(4-amino-N-piperidinyl)phenyl]-5-isoxazolyl] phenyl] Acetamide; MW=480 confirmed by LC-MS, $t_r$=10.90 min (Method Y) MH$^+$=479–483

Preparation of 1,2,4-Oxadiazoles

2,2-Dichloro-N-[3-[3-(2,6-dichlorophenyl)-5-(1,2,4 oxadiazolyl)]phenyl] Acetamide (Compound 25)

Step 1

2,6-Dichlorobenzamidoxime (1.0 g) was dissolved in pyridine and m-nitrobenzoyl chloride (0.91 gm, 1.0 molar equivalent) was added. The solution was stirred at room temperature for 1 h under nitrogen, then heated at 90° C. for 4 h. The solution was cooled to room temperature, and poured into ice water. The pH of the solution was adjusted to approximately pH 10 with 2M aqueous sodium carbonate solution. The mixture was extracted with ether and the organic layer was dried over anhydrous sodium sulfate, filtered and concentrated under reduced pressure to dryness. The residue was dissolved in ethyl acetate. Addition of hexanes to the solution gave 3-(2,6-dichlorophenyl)-5-(3-nitrophenyl)-1,2,4-oxadiazole as a white solid (0.69 g). NMR (300 MHz, DMSO-$d_6$): 8.52 (s, 1H), 8.38 (d, 1H), 8.18 (d, 1H), 7.78 (t, 1H), 7.57 ppm (m, 3H). LC-MS $t_r$=38.2 min (Method W) MH$^+$+NA=359

Step 2

The nitro oxadiazole prepared in Step 1 (200 mg) was dissolved in ethyl acetate (20 mL) and tin (II) chloride dihydrate (162 mg, 1.2 molar equivalent) was added. The mixture was stirred at room temperature for 1 h. An additional 1.2 molar equivalents of tin (II) chloride was added. After a further 4 h at room temperature, the reaction mixture was diluted with ethyl acetate and washed three times with water. The organic layer was dried over anhydrous sodium sulfate, filtered and concentrated under reduced pressure to give the desired 3-(2,6-dichlorophenyl)-5-(3-aminophenyl)-1,2,4-oxadiazole as a white solid in quantitative yield. NMR (300 MHz, DMSO-$d_6$): 7.70 (m, 3H), 7.36 (s, 1H), 7.24 (d, 2H), 6.91 (m, 1H), 5.57 ppm (broad s, 2H). LC-MS $t_r$=33.1 min (Method W) MH$^+$=307

Step 3

The aminophenyl oxadiazole prepared in Step 2 (200 mg) was dissolved in 5 mL of dichloromethane, triethylamine (90 μL, 1.0 molar equivalent) was added, and the mixture was cooled in an ice-bath under nitrogen. Then dichloroacetyl chloride (65 μL, 1.0 molar equivalent) was added and the mixture was allowed to stir for 2 h at 0° C. The solution was diluted with dichloromethane and then washed with saturated aqueous sodium bicarbonate followed by brine. The organic layer was dried over anhydrous sodium sulfate, filtered and concentrated under reduced pressure to give a brown oil. Purification by column chromatography on silica gel, eluting with 8:1 hexanes-ethyl acetate, gave a colorless oil. Trituration of the oil with hexanes-ethyl acetate gave the title compound, 2,2-dichloro-N-[3-[3-(2,6-dichlorophenyl)-5-(1,2,4-oxadiazolyl)]phenyl] acetamide, as a white solid (70 mg). NMR (300 MHz, CDCl$_3$): 8.34 (m, 2H), 8.05 (d, 1H), 8.00 (d, 1H), 7.59 (t, 1H), 7.44 (m, 3H), 6.09 ppm (s, 1H). LC-MS $t_r$=20.71 min (Method X) MH$^+$=418

Preparation of Pyrazoles

2,2Dichloro-N-[3-[3-(2,6-dichlorphenyl)-5-(pyrazolyl)]phenyl] Acetamide (Compound 189)

Step 1

To a stirred solution of lithium bis(trimethylsilyl)amide (1.0 molar in tetrahydrofuran, 11 mL, 1.1 mole equivalent) cooled at −70 under nitrogen was added dropwise a solution of 2,6 dichloroacetophenone (965 mg, 1.0 molar equivalent) in anhydrous tetrahydrofuran. The resulting mixture was stirred at −20° C. for 2 h. The reaction mixture was re-cooled to −70° C., and a solution of 3-nitrobenzoylcyanide (900 mg, 1.0 molar equivalent) in tetrahydrofuran was added dropwise. The 3-nitrobenzoylcyanide was prepared according to the procedures of S. Yamaguchi et. al. in, Bull. Chem. Soc. Jpn. 1989, 62,3036–3037. The mixture was allowed to warm to room temp over 1 h and was stirred at room temperature for 2 h. The reaction was quenched by the addition of saturated aqueous ammonium chloride. The reaction mixture was extracted with ethyl acetate. The organic layer was dried over anhydrous sodium sulfate, filtered, and concentrated under reduced pressure to dryness. The crude solid product was purified by column chromatography over silica gel using hexanes and ethyl acetate to give the desired 1-(2,6-dichlorophenyl)-3-(3-nitrophenyl)-1,3 propanedione. NMR 300 MHz (CDCL$_3$) 8.75 (m, 1H), 8.40 (m, 1H), 8.28 (m, 1H), 7.69 (t, 1H), 7.39 (m, 2H), 6.43 (s, 2H)

Step 2

The diketone prepared in Step 1 (100 mg) was dissolved in ethanol. To this solution was added hydrazine monohydrate (5 molar equivalents) and 1 drop of concentrated hydrochloric acid. The mixture was then heated at 80–90° C. overnight. The solvent was removed under reduced pressure. The residue was dissolved in ethyl acetate and washed with saturated sodium bicarbonate solution. The organic layer was dried over anhydrous sodium sulfate, filtered, and concentrated under reduced pressure to give the desired pyrazole as a white solid (57 mg). NMR (300 MHz, CDCl$_3$): 8.69 (t, 1H), 8.22 (m, 2H), 7.62 (t, 1H), 7.44 (d, 2H), 7.33 (m, 1H), 6.86 ppm (s, 1H). LC-MS $t_r$=14.53 min (Method Y) MH$^+$=333–337

Step 3

The 3-(2,6-dichlorophenyl)-5-(3-nitrophenyl) pyrazole prepared in Step 2 (57 mg) was dissolved in 50% aqueous ethanol and treated with iron powder (57 mg, 6 molar equivalents), and ammonium chloride (18.2 mg, 2 molar equivalents). The mixture was heated at 70–80° C. for 4 h. The reaction mixture was cooled to room temperature then filtered and the filtrate was concentrated to dryness under reduced pressure. The residue was dissolved in ethyl acetate and washed with water and brine. The organic layer was dried over anhydrous sodium sulfate, filtered and concentrated under reduced pressure to give 3-(2,6-dichlorophenyl)-5-(3-aminophenyl)pyrazole as a white solid (27 mg). NMR (300 MHz, CDCl$_3$): 7.40 (d, 2H), 7.25 (t, 1H), 7.20 (m, 1H), 7.11 (m, 2H), 6.68 ppm (m, 2H). LC-MS $t_r$=5.66 min (Method Z) MH$^+$=303–307

Step 4

Dichloroacetic acid (13 mg, 1.1 molar equivalents), O-(7-azabenzotriazol-1-yl)-N,N,N',N'-tetramethyluronium hexafluorophosphate (HATU) (38 mg, 1.1 molar equivalent), and N-methylmorpholine (22 μL, 2.2 molar equivalents) were dissolved in anhydrous dichloromethane and stirred for 5 minutes. Then the 3-(2,6-dichlorophenyl)-5-(3-aminophenyl)pyrazole prepared in Step 3 was added, and the mixture stirred at room temperature overnight. The reaction mixture was diluted with ethyl acetate and washed with 1M aqueous hydrochloric acid, saturated sodium bicarbonate solution, then brine. The organic layer was dried over anhydrous sodium sulfate, filtered, and concentrated under reduced pressure. The crude product was purified by column chromatagraphy eluting with 25% ethyl acetate in hexanes to give 2,2-Dichloro-N-[3-[3-(2,6-dichlorophenyl)-5-(pyrazolyl)]phenyl] acetamide as a white solid. NMR (300 MHz, CDCl$_3$): 8.40 (broad s, 1H), 8.00 (broad s, 1H), 7.62

(t, 2H), 7.43 (m, 3H), 7.30 (m, 2H), 6.78 (broad s, 1H), 6.07 ppm (s, 1H). LC-MS $t_r$=13.75 min (Method Y) MH$^+$= 415–419.

7.2 Exemplary Compounds of the Invention Inhibit HCV Translation or Replication

7.2.1 Replicon Assay

The inhibitory activity of certain exemplary compounds of the invention was confirmed using an HCV replicon assay. The HCV replicon can include such features as the HCV 5' untranslated region including the HCV IRES, the HCV 3' untranslated region, selected HCV genes encoding HCV polypeptides, selectable markers, and a reporter gene such as luciferase, GFP, etc. In the assay, actively dividing 5-2 Luc replicon-comprising cells (obtained from Rolf Bartenschlager; see Lohmann et al., 1999, Science 285:110–113) were seeded at a density of between about 5,000 and 7,500 cells/well onto 96 well plates (about 90 μl of cells per well) and incubated at 37° C. and 5% $CO_2$ for 24 hours. Then, the test compound (in a volume of about 10 μl) was added to the wells at various concentrations and the cells were incubated for an additional 24 hours before luciferase assay. The media was aspirated from each well and Bright-Glo (Promega, Madison, Wis.) luciferase assay reagents were added to each well according to the manufacturer's instructions. Briefly, the Bright-Glo reagent was diluted 1:1 with PBS and 100 μl of diluted reagent was added to each well. After 5 min of incubation at room temperature, luciferin emission was quantified with a luminometer. In this assay, the amount of test compound that yielded a 50% reduction in luciferase emission ($IC_{50}$) was determined.

7.2.2 Western Blot Assay

Certain exemplary compounds of the invention were also tested for their ability to inhibit HCV replication using a quantitative Western blot analysis with antibodies specific for the HCV nonstructural protein NS5A. Actively dividing 9–13 replicon cells were seeded into 6-well plates at a density of $1\times10^5$ cells/well in a volume of 2 ml/well and incubated at 37° C. and 5% $CO_2$ for 24 hours. Various concentrations of test compounds (in a volume of 10 ul) were added to the wells and the cells incubated for another 48 hours. Protein samples were prepared from the cultured cells, resolved on a SDS-PAGE gel and transferred to a nitrocellulose membrane. The membrane was blocked with 5% non-fat milk in PBS for 1 hour at room temperature. Primary antibody (anti NS5A antibody; BIODESIGN International, Saco, Me.) incubation was performed for 1 hour at room temperature, after which the membrane was washed 3 times (for 15 min per time) with PBST (PBS plus 0.1% Tween 20). Horseradish peroxidase conjugated secondary antibody incubation was performed for 1 hour at room temperature and the membrane was washed 3 times (for 15 min per time) with PBST. The membrane was then soaked in substrate solution (Pierce) and exposed to a film or quantified using an imager. In this assay, the amount of test compound that yielded a 50% reduction in the amount of NS5A protein translated as compared to a control sample ($IC_{50}$) was determined.

The results of the Replicon and Western blot assays are provided in TABLE 1, below. In TABLE 1, a value of "+" indicates an $IC_{50}$ of 10 μM or less in the specified assay; a value of "−" indicates an $IC_{50}$ of greater than 10 μM in the specified assay. Many of the compounds exhibited $IC_{50}$s in the Replicon assay in the nanomolar range.

TABLE 1

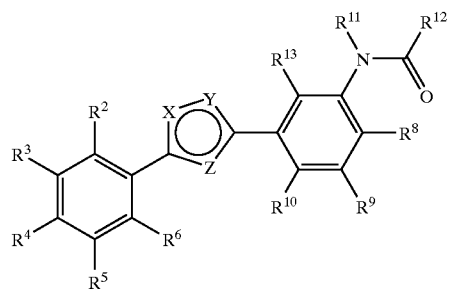

| Cmpd | Replicon/ Western | X | Y | Z | $R^2$ | $R^3$ | $R^4$ | $R^5$ |
|---|---|---|---|---|---|---|---|---|
| 1 | +/+ | N | O | CH | Cl | H | H | H |
| 3 | −/+ | N | O | CH | Cl | Cl | H | H |
| 5 | +/+ | O | N | CH | Cl | H | H | H |
| 7 | +/+ | N | O | CH | Cl | H | H | H |
| 9 | +/+ | N | O | CH | Cl | H | H | H |
| 11 | +/+ | N | O | CH | F | H | H | H |
| 13 | +/+ | N | O | CH | Cl | H | H | H |
| 15 | +/+ | N | O | CH | F | H | H | Me |
| 21 | +/+ | N | O | CH | F | H | H | H |
| 23 | + | N | O | CH | Me | H | 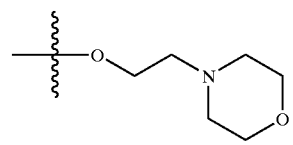 | H |
| 25 | | N | O | N | Cl | H | H | H |
| 27 | +/+ | N | O | CH | Cl | H | H | H |
| 29 | + | N | O | CH | Cl | H | H | H |

TABLE 1-continued

| | | | | | | | | |
|---|---|---|---|---|---|---|---|---|
| 31 | + | N | O | CH | Cl | H | H | H |
| 33 | + | N | O | CH | CF₃ | H | H | H |
| 35 | + | N | O | CH | CF₃ | H | H | H |
| 37 | +/+ | N | O | CH | CF₃ | H | H | H |
| 39 | + | N | O | CH | Cl | H | H | H |
| 41 | + | N | O | CH | CF₃ | H | H | H |
| 43 | + | N | O | CH | F | H | H | H |
| 45 | + | N | O | CH | OCHF₂ | H | H | H |
| 47 | + | N | O | CH | Me | H | H | H |
| 49 | + | N | O | CH | I | H | H | H |
| 51 | + | N | O | CH | F | Me | H | H |
| 53 | + | N | O | CH | F | H | H | F |
| 57 | + | N | O | CH | Cl | H | H | H |
| 61 | + | N | O | CH | OEt | H | H | H |
| 63 | + | N | O | CH | iPr | H | H | H |
| 65 | + | N | O | CH | Cl | H | N(Me)₂ | H |
| 67 | + | N | O | CH | Cl | H | H | H |
| 69 | + | N | O | CH | Me | H | Me | H |
| 73 | + | N | O | CH | Cl | H | 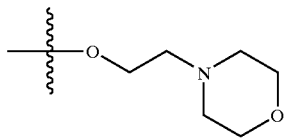 | H |
| 75 | −/+ | N | O | CH | Cl | H | 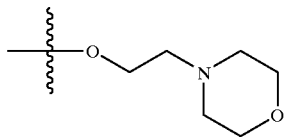 | H |
| 77 | + | N | O | CH | CF₃ | H | H | H |
| 79 | + | N | O | CH | Cl | H | H | H |
| 81 | + | N | O | CH | Cl | H | H | H |
| 83 | + | N | O | CH | Cl | H | H | H |
| 85 | + | N | O | CH | CF₃ | H | H | H |
| 87 | + | O | N | N | Cl | H | H | H |
| 89 | + | N | O | CH | CF₃ | H | H | H |
| 91 | + | N | O | CH | Me | H | H | H |
| 93 | + | N | O | CH | CF₃ | H | H | H |
| 95 | + | N | O | CH | Cl | H | H | H |
| 97 | + | N | O | CH | Cl | H | H | H |
| 99 | + | N | O | CH | Cl | H | H | H |
| 101 | +/− | N | O | CH | Cl | H | H | H |
| 103 | + | N | O | CH | Cl | H | H | H |
| 105 | + | N | O | CH | CF₃ | H | H | H |
| 107 | + | N | O | CH | Cl | H | H | H |
| 109 | + | N | O | CH | CF₃ | H | H | H |
| 111 | + | N | O | CH | Cl | H | H | H |
| 113 | + | N | O | CH | OCF₃ | H | H | H |
| 115 | + | N | O | CH | C(O)OMe | H | H | H |
| 117 | + | N | O | CH | Cl | H | H | H |
| 119 | + | N | O | CH | O-iPr | H | H | H |
| 121 | + | N | O | CH | iPr | H | H | H |
| 123 | + | N | O | CH | Ph | H | H | H |
| 125 | + | N | O | CH | Cl | H | 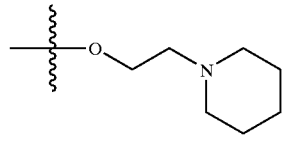 | H |
| 127 | + | N | O | CH | Cl | H | H | H |
| 129 | + | N | O | CH | 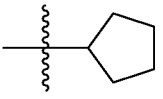 | H | H | H |
| 131 | + | N | O | CH | Cl | H | H | H |
| 132 | + | N | O | CH | Cl | H | H | H |
| 135 | −/− | N | O | CH | Cl | C(O)OMe | H | H |
| 137 | − | N | O | CH | Cl | H | H | Cl |
| 139 | − | N | O | CH | Cl | C(O)OH | H | H |

TABLE 1-continued

| 141 | − | N | O | CH | Cl | H | H | CF$_3$ |
|---|---|---|---|---|---|---|---|---|
| 143 | − | N | O | CH | Cl | H | Cl | H |
| 145 | − | N | O | CH | Cl | H | H | H |
| 149 | − | N | O | CH | F | Me | H | H |
| 151 | − | N | O | CH | Cl | H | H | H |
| 153 | − | N | O | CH | F | H | H | H |
| 155 | | N | O | CH | H | H | H | H |
| 157 | − | N | O | CH | C(O)OH | H | H | H |
| 159 | | N | O | CH | H | H | Cl | H |
| 161 | − | N | O | CH | H | H | H | H |
| 163 | −/− | N | O | CH | Me | Me | H | H |
| 165 | − | N | O | CH | Cl | H | H | H |
| 167 | − | N | O | CH | Cl | H | H | H |
| 169 | − | N | O | CH | Cl | H | H | H |
| 171 | − | N | O | CH | Cl | H | H | H |
| 173 | + | N | O | CH | Cl | H | H | H |
| 175 | | N | O | CH | Cl | H | H | H |
| 177 | | N | O | CH | Cl | H | H | H |
| 179 | | N | O | CH | Br | H | H | H |
| 181 | | N | O | CH | Cl | H | H | H |
| 183 | | N | O | CH | OMe | H | H | H |
| 185 | | N | O | CH | Br | H | H | H |
| 187 | | N | O | CH | Cl | H | H | H |
| 189 | | N | N | CH | Cl | H | H | H |

| Cmpd | R$^6$ | R$^8$ | R$^9$ | R$^{10}$ | R$^{11}$ | R$^{12}$ | R$^{13}$ |
|---|---|---|---|---|---|---|---|
| 1 | Cl | F | H | H | H | CHCl$_2$ | H |
| 3 | H | H | H | H | H | CHCl$_2$ | H |
| 5 | Cl | H | H | H | H | CHCl$_2$ | H |
| 7 | 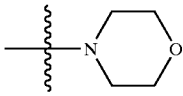 | H | H | H | H | CHCl$_2$ | H |
| 9 | Cl | H | H | H | H | CHCl$_2$ | H |
| 11 | SMe | H | H | H | H | CHCl$_2$ | H |
| 13 | Cl | H | H | F | H | CHCl$_2$ | H |
| 15 | Cl | H | H | H | H | CHCl$_2$ | H |
| 21 | 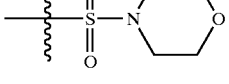 | H | H | H | H | CHCl$_2$ | H |
| 23 | Me | H | H | H | H | CHCl$_2$ | H |
| 25 | Cl | H | H | H | H | CHCl$_2$ | H |
| 27 | F | H | H | H | H | CHCl$_2$ | H |
| 29 | Cl | H | H | H | H | CHBr$_2$ | H |
| 31 | Me | H | H | H | H | CHCl$_2$ | H |
| 33 | H | H | H | H | H | CHCl$_2$ | H |
| 35 | OH | H | H | H | H | CHCl$_2$ | H |
| 37 | 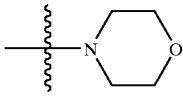 | H | H | H | H | CHCl$_2$ | H |
| 39 | iPr | H | H | H | H | CHCl$_2$ | H |
| 41 | F | H | H | H | H | CHCl$_2$ | H |
| 43 | OMe | H | H | H | H | CHCl$_2$ | H |
| 45 | H | H | H | H | H | CHCl$_2$ | H |
| 47 | Me | H | H | H | H | CHCl$_2$ | H |
| 49 | F | H | H | H | H | CHCl$_2$ | H |
| 51 | Cl | H | H | H | H | CHCl$_2$ | H |
| 53 | Cl | H | H | H | H | CHCl$_2$ | H |
| 57 | Cl | H | H | H | Me | CHCl$_2$ | H |
| 61 | H | H | H | H | H | CHCl$_2$ | H |
| 63 | H | H | H | H | H | CHCl$_2$ | H |
| 65 | Cl | H | H | H | H | CHCl$_2$ | H |
| 67 | Cl | H | H | H | H | CH$_2$Cl | H |
| 69 | Me | H | H | H | H | CHCl$_2$ | H |
| 73 | Cl | H | H | H | H | CHCl$_2$ | H |
| 75 | Cl | H | H | H | H | CHCl$_2$ | H |
| 77 | OMe | H | H | H | H | CHCl$_2$ | H |

TABLE 1-continued

| | | | | | | | | |
|---|---|---|---|---|---|---|---|---|
| 79 | 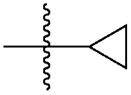 | H | H | H | H | CHCl$_2$ | H |
| 81 | OMe | H | H | H | H | CHCl$_2$ | H |
| 83 | OH | H | H | H | H | CHCl$_2$ | H |
| 85 | Me | H | H | H | H | CHCl$_2$ | H |
| 87 | Cl | H | H | H | H | CHCl$_2$ | H |
| 89 | 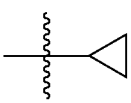 | H | H | H | H | CHCl$_2$ | H |
| 91 | OMe | H | H | H | H | CHCl$_2$ | H |
| 93 | iPr | H | H | H | H | CHCl$_2$ | H |
| 95 | 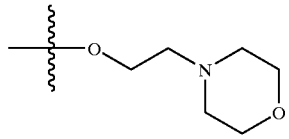 | H | H | H | H | CHCl$_2$ | H |
| 97 | 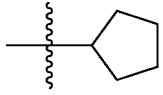 | H | H | H | H | CHCl$_2$ | H |
| 99 | 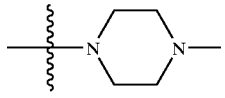 | H | H | H | H | CHCl$_2$ | H |
| 101 | Cl | H | H | H | H | CH$_2$I | H |
| 103 | nBu | H | H | H | H | CHCl$_2$ | H |
| 105 | 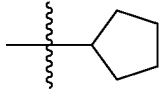 | H | H | H | H | CHCl$_2$ | H |
| 107 | Cl | H | H | 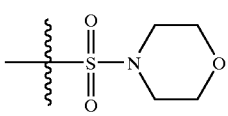 | H | CHCl$_2$ | H |
| 109 | 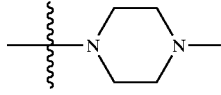 | H | H | H | H | CHCl$_2$ | H |
| 111 | 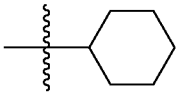 | H | H | H | H | CHCl$_2$ | H |
| 113 | H | H | H | H | H | CHCl$_2$ | H |
| 115 | H | H | H | H | H | CHCl$_2$ | H |
| 117 | 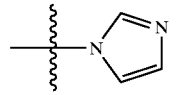 | H | H | H | H | CHCl$_2$ | H |
| 119 | H | H | H | H | H | CHCl$_2$ | H |
| 121 | iPr | H | H | H | H | CHCl$_2$ | H |
| 123 | H | H | H | H | H | CHCl$_2$ | H |
| 125 | H | H | H | H | H | CHCl$_2$ | H |
| 127 | Cl | H | H | OMe | H | CHCl$_2$ | H |
| 129 | H | H | H | H | H | CHCl$_2$ | H |

TABLE 1-continued

| # | R1 | R2 | R3 | R4 | R5 | R6 | R7 |
|---|---|---|---|---|---|---|---|
| 131 | ~N(Me)CH2CH2N(Me)2~ | H | H | H | H | CHCl2 | H |
| 132 | ~1-(3-dimethylaminopyrrolidinyl)~ | H | H | H | H | CHCl2 | H |
| 135 | Cl | H | H | H | H | CHCl2 | H |
| 137 | Cl | H | H | H | H | CHCl2 | H |
| 139 | Cl | H | H | H | H | CHCl2 | H |
| 141 | H | H | H | H | H | CHCl2 | H |
| 143 | ~O-CH2CH2-morpholinyl~ | H | H | H | H | CHCl2 | H |
| 145 | Cl | H | H | H | H | CHF2 | H |
| 149 | F | H | H | H | H | CHCl2 | H |
| 151 | ~1-(4-ethoxycarbonylpiperidinyl)~ | H | H | H | H | CHCl2 | H |
| 153 | SO2Me | H | H | H | H | CHCl2 | H |
| 155 | ~CH2-morpholinyl~ | H | H | H | H | CHCl2 | H |
| 157 | H | H | H | H | H | CHCl2 | H |
| 159 | Cl | H | H | H | H | CHCl2 | H |
| 161 | OBz | H | H | H | H | CHCl2 | H |
| 163 | H | H | H | H | H | CHCl2 | H |
| 165 | Cl | Me | H | H | H | CHCl2 | H |
| 167 | Cl | H | H | H | H | CHCl2 | Me |
| 169 | Cl | ~morpholinyl~ | H | H | H | CHCl2 | H |
| 171 | Cl | ~O-CH2CH2-morpholinyl~ | H | H | H | CHCl2 | H |
| 173 | Cl | OMe | H | H | H | CHCl2 | H |
| 175 | ~1-(4-piperidinyl)piperidinyl~ | H | H | H | H | CHCl2 | H |
| 177 | H | H | H | H | H | CHCl2 | H |
| 179 | H | H | H | H | H | CHCl2 | H |
| 181 | NO2 | H | H | H | H | CHCl2 | H |
| 183 | H | H | H | H | H | CHCl2 | H |
| 185 | Cl | H | H | H | H | CHCl2 | H |

TABLE 1-continued

| # | Structure | | | | | | |
|---|---|---|---|---|---|---|---|
| 187 | —N⟨ ⟩—NH₂ (piperidinyl-NH₂) | H | H | H | H | CHCl₂ | H |
| 189 | Cl | H | H | H | H | CHCl₂ | H |

7.2.3 Luciferase Counter Screen

A counter screen was used to identify non-specific inhibitors of the luciferase reporter gene. In the counter screen, a cell line carrying a construct such as a CMV-driven luciferase gene was used to identify compounds that inhibit the reporter gene, and not HCV. In these CMV-Luc cells, the DNA construct, which comprises a luciferase gene downstream of a CMV promoter, is permanently integrated into the chromosome of Huh7 cells. For the counter screen, actively dividing CMV-Luc cells were seeded at a density of 5000–7500 cells/well in a volume of 90 ul/well into 96 well plate(s). The cells were then incubated at 37° C. and 5% $CO_2$ for 24 hours. Various concentrations of test compounds (in a volume of 10 ul) were added to the wells and the cells were incubated for another 24 hours. Media was aspirated from each well and Bright-Glo (Pharmacia) luciferase assay reagents were added to each well according to the manufacturer's manual. Luciferin counts were taken using a luminometer. $IC_{50}$ values were greater than 10 μM in the counter screen luciferase inhibition assay for the compounds of TABLE 1 that were tested.

7.2.4 PCR Assay

A TaqMan RT-PCR assay (Roche Molecular Systems, Pleasanton, Calif.) was used to analyze HCV RNA copy numbers, which confirmed that the viral genome of HCV is not being replicated. Actively dividing 9–13 replicon cells were seeded at a density of $3 \times 10^4$ cells/well in a volume of 1 ml/well into 24-well plates. The cells were then incubated at 37° C. and 5% $CO_2$ for 24 hours. Various concentrations of test compounds (in a volume of 10 ul) were added to the wells and the cells were incubated for an additional 24–48 hours. Media was removed by aspiration and RNA samples prepared from each well. TaqMan one step RT-PCR (Roche Molecular Systems, Alameda, Calif.) was performed using the freshly prepared RNA samples according to the manufacturer's manual and analyzed on an ABI Prism 7700 Sequence Detector (Applied Biosystems). The ratio of HCV RNA to cellular GAPDH RNA was used as in indication of specificity of HCV inhibition to confirm that the viral genome was not replicated.

7.2.5 HCV Infection Assay

The activity of Compound 9 was also confirmed in an HCV infection assay. The assay was carried out essentially as described in Fournier et al., 1998, J. Gen. Virol. 79:2367–2374. Briefly, hepatocyte cells from a doner were plated on Day 1. On Day 3, the cells were inoculated with HCV virus and test compound was added. On Day 5, the medium was changed and test compound was added. On Day 7, the medium was changed and test compound was added. On Day 8, the RNA was isolated and the HCV RNA quantified using a Taqman assay. Compound 9 exhibited an $IC_{50}$ of less than 10 μM in this assay.

7.3 The Compounds are Non-Toxic in Cellular and Animal Models

7.3.1 Cytotoxicity

Compounds 67, 167, 169, 13, 1, 145, 29, 119, 63, 31, 39, 103, 123, 121, 97, 129, 79, 111, 85, 89, 109, 127, 131, 95, 47, 57, 69, 165, 161, 163, 3, 137, 15, 141, 41, 53, 33, 113, 93, 105, 77, 91, 81, 83, 35, 27, 65, 7, 135, 51, 139, 51, 49, 143, 5, 149, 11, 37, 21, 45, 61, 75, 23, 125, 73, 43, 171 and 101 were tested in a cytotoxicity assay with liver cells including an HCV replicon (5-2 Luc cells, 9–13 cells or Huh-7 cells). In the assay, cells were seeded onto 96-well plates (approx. 7500 cells/well in a volume of 90 μl) and grown for 24 hr at 37° C. On day 2, various concentrations of test compound (in a volume of 10 μl) were added to the wells and the cells were grown for an additional 24 hr at 37° C. On day 3, an ATP-dependent R-Luciferase assay (Cell Titer Glo assay) was performed to determine the number of viable cells. With the exception of compounds 67, 47, 69, 105, 27 and 23, all compounds tested exhibited an $IC_{50}$ of greater than 10 μM, confirming that the compounds are non-toxic. Of the remaining compounds, all but compound 69, which exhibited an $IC_{50}$ of 3 μM, had $IC_{50}$s greater than 5 μM, demonstrating that these compounds are well-tolerated, as well.

7.3.2 Animal Studies

The safety of compound 9 was evaluated in rats by both subcutaneous and intravenous administration in several experiments. Doses as high as 30 mg/kg/day were well tolerated. The experiments performed are summarized below.

In a first study the toxicity of compound 9 was evaluated either by the subcutaneous (SC) route or the intravenous (IV via jugular cannula) route of administration in Sprague Dawley rats. There were two male rats in each group. A dose escalation scheme was employed where compound 9 was delivered IV or SC for 3 consecutive days at a dose of 10 mg/kg (study Days 1–3) in a 80%:20%-PEG/water vehicle; delivered one day IV or SC dose of 30 mg/kg (study Day 4) in 100% PEG; and an IV dose of 60 mg/kg (study Day 5) in 100% PEG. Compound 9 was well tolerated at doses up to and including 30 mg/kg by both routes of administration. However, when the IV dose was increased to 60 mg/kg on Day 5 immediate clinical signs (collapsing, thrashing, dyspnea and reddish discolored urine) were observed. The symptoms were transient abating within 1 hour. Toxicokinetic determinations from the current study and what is known from an earlier experiment demonstrate high exposure from the IV route and much lower exposure via the subcutaneous route. As expected by the IV route Cmax is achieved rapidly at about two minutes with a T1/2 of about 5 minutes with measurable compound 9 still apparent after 2 hours. By the SC route Tmax is achieved at about 30 minutes and exposure remains sustained through 2 hours post-dosing.

In a second study compound 9 was administered by the IV route at doses of 10 and 30 mg/kg in 100% PEG. The volume administered for the 10 mg/kg dose was 0.67 ml/kg/day and volume given the 30 mg/kg group was 2 ml/kg/day. In addition, there were two control groups. One control received 100% PEG alone at a volume of 2 ml/kg/day while the other was an untreated sham control group. All groups (except for the untreated control with 3 male rats)

had 4 male rats each. Parameters of study included: clinical observations, body weights, hematology, clinical chemistry, gross necropsy, organ weights, bone marrow assessment and histopathology of selected organs. There were very slight decreases in red blood cells, hemoglobin and hematocrit at 30 mg/kg relative to the untreated control but not the vehicle control. Otherwise, there were no untoward findings in any other in life parameter, clinical pathology, bone marrow cytology, gross and/or microscopic morphological changes attributed to compound 9 observed in the study. A dose of 30 mg/kg was considered the NOAEL (no observed adverse effect level) by the IV route of administration during 7 days.

In a third study compound 9 was compared with two other compounds and administered at a dose of 10 and 30 mg/kg in 100% PEG and delivered by IV at a concentration of 1 ml/kg/day first via a jugular cannula and when the cannula failed by the lateral tail vein. A vehicle control group received the 100% PEG alone at the same volume. Groups comprised 3 males and 3 females each. Before reducing the dose to 10 and 30 mg/kg two rats received 100 mg/kg IV at a volume of 1 ml/kg. Both animals died within a minute or two of dosing acutely from apparent respiratory failure. Necropsy revealed only that a drug precipitate had formed at the terminal end of the cannula. Death may have been associated with an emboli formed by precipitated drug. Parameters of study included: clinical observations, body weights, hematology, clinical chemistry, gross necropsy, organ weights and histopathology of selected organs (including injection sites).

Clinical observations, body weights, hematology and clinical chemistry and organ weights were unaffected by treatment with compound 9 when compared with the vehicle control. At necropsy there were no gross or microscopic morphological changes associated with compound 9. There were, nevertheless, changes/lesions attributed to the irritancy of the 100% PEG vehicle. These changes included those associated with the injection site focal to the tissues surrounding or in proximity to the end of the cannula (several terminal ends of the cannulas were obstructed) and in the tail and/or changes associated with subacute IV administration of several animals in both the compound 9 and-vehicle control group. The NOAEL for intravenous administration of compound 9 during 14-days was judged to be 30 mg/kg.

7.4 Sustained Plasma Levels are Achieved

The pharmacokinetic properties of compound 9 were calculated in rats, monkeys and chimpanzees using the intravenous and subcutaneous routes of administration with a variety of different delivery vehicles. Sustained plasma levels were achieved with several different liposome suspension vehicles using subcutaneous administration: (i) 5 mg/ml compound 9 in water with 100 mg/ml lecithin; (ii) 5 mg/ml compound 9 in water with 200 mg/ml lecithin; and (iii) 5 mg/ml compound 9 in water with 100 mg/ml lecithin and 5 mg/ml cholesterol. Based on these results, it is expected that other liposome formulations as are well-known in the art may be used to administer the compounds of the invention All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A compound according to structural formula (I):

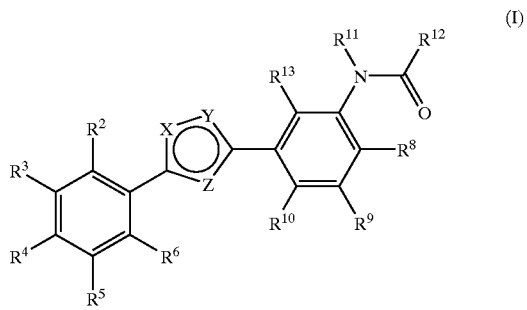

including the pharmaceutically acceptable salts, hydrates, solvates, N-oxides and prodrugs thereof, wherein:

X and Y are each, independently of one another, N or O, provided that X and Y are not both O;

Z is N or —CH—, provided that Z is —CH— when X and Y are both N;

$R^2$, $R^3$, $R^4$, $R^5$, $R^6$, $R^8$, $R^9$, $R^{10}$ and $R^{13}$ are each, independently of one another, selected from the group consisting of hydrogen, —OH, —SH, —CN, —NO$_2$, halo, fluoro, chloro, bromo, iodo, lower alkyl, substituted lower alkyl, lower heteroalkyl, substituted lower heteroalkyl, cycloalkyl, substituted cycloalkyl, cycloheteroalkyl, substituted cycloheteroalkyl, lower haloalkyl, monohalomethyl, dihalomethyl, trihalomethyl, trifluoromethyl, lower alkylthio, substituted lower alkylthio, lower alkoxy, substituted lower alkoxy, methoxy, substituted methoxy, lower heteroalkoxy, substituted lower heteroalkoxy, cycloalkoxy, substituted cycloalkoxy, cycloheteroalkoxy, substituted cycloheteroalkoxy, lower haloalkoxy, monohalomethoxy, dihalomethoxy, trihalomethoxy, trifluoromethoxy, amino, lower di- or monoalkylamino, substituted lower di- or monoalkylamino, aryl, substituted aryl, aryloxy, substituted aryloxy, phenoxy, substituted phenoxy, arylalkyl, substituted arylalkyl, arylalkyloxy, substituted arylalkyloxy, benzyl, benzyloxy, heteroaryl, substituted heteroaryl, heteroaryloxy, substituted heteroaryloxy, heteroarylalkyl, substituted heteroarylalkyl, heteroarylalkyloxy, substituted heteroarylalkyloxy, carboxyl, lower alkoxycarbonyl, substituted lower alkoxycarbonyl, aryloxycarbonyl, substituted aryloxycarbonyl, arylalkyloxycarbonyl, substituted arylalkyloxycarbonyl, carbamate, substituted carbamate, carbamoyl, substituted carbamoyl, sulfamoyl, substituted sulfamoyl and a group of the formula —L—$R^{14}$, where "L" is a linker and $R^{14}$ is cycloalkyl, substituted cycloalkyl, cycloheteroalkyl or substituted cycloheteroalkyl, provided that at least one of $R^2$ or $R^6$ is other than hydrogen;

$R^{11}$ is hydrogen or lower alkyl; and $R^{12}$ is monohalomethyl or dihalomethyl, wherein the compound is not 2,2-dichloro-N—[3-[3-(2,6-dichlorophenyl-5-isoxazolyluhenyl] acetamide or 2,2-dichloro-N—[3-[3-(2,4-dichlorophenyl)-5-isoxazolylkhenyl] acetamide.

2. The compound of claim 1 in which $R^{11}$ is hydrogen and $R^{12}$ is dichloromethyl or dibromomethyl.

3. The compound of claim 2 in which Z is CH.

4. The compound of claim 2 in which X is O and Y is N.

5. The compound of claim 2 in which X is N and Y is O.

6. The compound of claim 2 in which X and Y are each N.

7. A The compound of claim 1 in which Z is N.

8. The compound of any one of claims 1–7 in which $R^8$, $R^9$, $R^{10}$ and $R^{13}$ are each hydrogen.

9. The compound of any one of claims 1–7 in which $R^3$ and $R^5$ are each hydrogen.

10. The compound of claim 9 in which $R^4$ is —L—$R^{14}$.

11. The compound of claim 10 in which L is —O—$(CH_2)_{1-3}$— and $R^{14}$ is N-morpholinyl.

12. The compound of any one of claims 1–7 in which $R^3$, $R^4$ and $R^5$ are each hydrogen.

13. The compound of claim 12 in which $R^2$ and $R^6$ are each, independently of one another, selected from the group consisting of —OH, —$NO_2$, halo, fluoro, chloro, bromo, iodo, lower alkyl, methyl, lower heteroalkyl, (C3–C6) cycloalkyl, 5- or 6-membered cycloheteroalkyl, N-morpholinyl, N-methyl-N-piperazinyl, N-piperadinyl, substituted N-piperadinyl, 4-(N-piperadinyl)-N-piperadinyl, 4-amino-N-piperadinyl, lower alkoxy, methoxy, ethoxy, lower alkylthio, methylthio, lower haloalkyl, monohalomethyl, dihalomethyl, trihalomethyl, trifluoromethyl, lower haloalkyloxy, monohalomethoxy, dihalomethoxy, trihalomethoxy, trifluoromethoxy, aryl, phenyl, arylalkyl, benzyl, aryloxy, phenoxy, arylalkyloxy, benzyloxy, 5- or 6-membered heteroaryl, lower alkyloxycarbonyl, sulfamoyl and —L—$R^{14}$, where L is —$(CH_2)_{1-3}$— or —O—$(CH_2)_{1-3}$— and $R^{14}$ is a 5- or 6-membered cycloheteroalkyl or N-morpholinyl.

14. The compound of claim 1 in which $R^2$ is selected from the group consisting of Cl, F, Me, —$CF_3$, —$OCHF_2$, I, Br, —OEt, -iPr, —$OCF_3$, —C(O)OMe, —O-iPr, Ph,

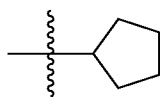

and COOH $R^3$ is selected from the group consisting of H, Cl, Me, —C(O)OMe, and COOH;

$R^4$ is selected from the group consisting of H, Cl,

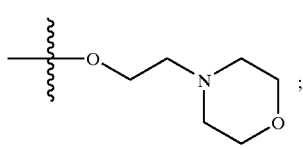

—$N(Me)_2$, Me and

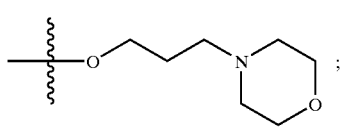

$R^5$ selected from the group consisting of H, Me, Cl, F and —$CF_3$;

$R^6$ is selected from the group consisting of H, Cl,

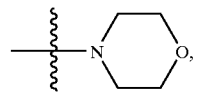

—SMe,

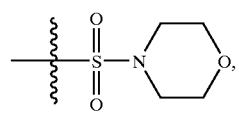

F, Me, OH, ipr, —OMe,

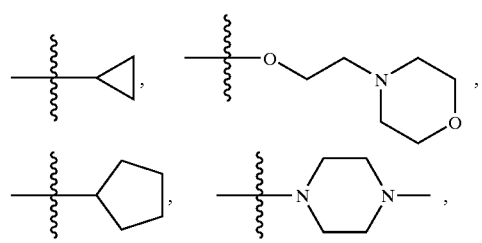

nBU

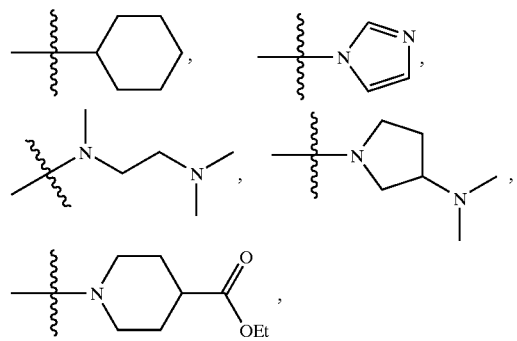

$SO_2Me$,

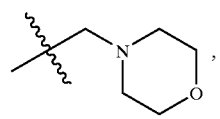

OBz,

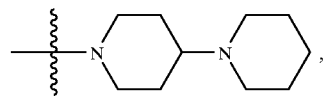

—$NO_2$ and

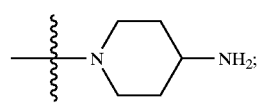

R⁸ is selected from the group consisting off, F, H, Me,

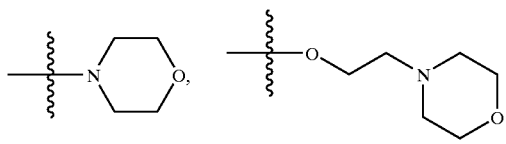

and —OMe;

R⁹ is H;

R¹⁰ is selected from the group consisting of H, F,

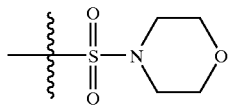

and —OMe;

R¹¹ is selected from the group consisting of H and Me;

R¹² is selected from the group consisting of —CHCl₂, —CH₂I₂, —CHBr₂ and —CHF₂; and R¹³ is selected from the group consisting of H and Me.

15. The compound of claim 14 in which the heterocyclic "B" ring is a pyrazole, isoxazole or oxadiazole analog or regioisomer thereof.

16. A composition comprising a pharmaceutically acceptable vehicle and a compound according to structural formula (I):

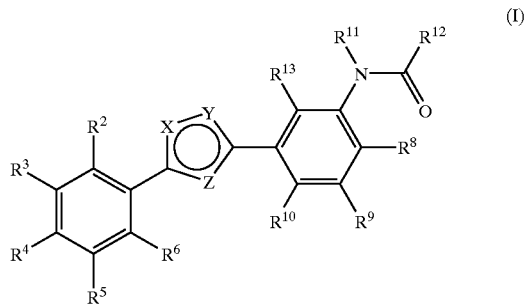

including the pharmaceutically acceptable salts, hydrates, solvates, N-oxides and prodrugs thereof, wherein:

X and Y are each, independently of one another, N or O, provided that X and Y are not both O;

Z is N or —CH—, provided that Z is —CH— when X and Y are both N;

R², R³, R⁴, R⁵, R⁶, R⁸, R⁹, R¹⁰ and R¹³ are each, independently of one another, selected from the group consisting of hydrogen, —OH, —SH, —CN, —NO₂, halo, fluoro, chloro, bromo, iodo, lower alkyl, substituted lower alkyl, lower heteroalkyl, substituted lower heteroalkyl, cycloalkyl, substituted cycloalkyl, cycloheteroalkyl, substituted cycloheteroalkyl, lower haloalkyl, monohalomethyl, dihalomethyl, trihalomethyl, trifluoromethyl, lower alkylthio, substituted lower alkylthio, lower alkoxy, substituted lower alkoxy, methoxy, substituted methoxy, lower heteroalkoxy, substituted lower heteroalkoxy, cycloalkoxy, substituted cycloalkoxy, cycloheteroalkoxy, substituted cycloheteroalkoxy, lower haloalkoxy, monohalomethoxy, dihalomethoxy, trihalomethoxy, trifluoromethoxy, amino, lower di- or monoalkylamino, substituted lower di- or monoalkylamino, aryl, substituted aryl, aryloxy, substituted aryloxy, phenoxy, substituted phenoxy, arylalkyl, substituted arylalkyl, arylalkyloxy, substituted arylalkyloxy, benzyl, benzyloxy, heteroaryl, substituted heteroaryl, heteroaryloxy, substituted heteroazyloxy, heteroarylalkyl, substituted heteroarylalkyl, heteroarylalkyloxy, substituted heteroarylalkyloxy, carboxyl, lower alkoxycarbonyl, substituted lower alkoxycarbonyl, aryloxycarbonyl, substituted aryloxycarbonyl, arylalkyloxycarbonyl, substituted arylalkyloxycarbonyl, carbamate, substituted carbamate, carbamoyl, substituted carbamoyl, sulfamoyl, substituted sulfamoyl and a group of the formula —L—R¹⁴, where "L" is a linker and R¹⁴ is cycloalkyl, substituted cycloalkyl, cycloheteroalkyl or substituted cycloheteroalkyl, provided that at least one of R² or R⁶ is other than hydrogen;

R¹¹ is hydrogen or lower alkyl; and

R¹² is monohalomethyl or dihalomethyl.

17. The composition of claim 16 which is a liposome suspension.

18. The composition of claim which comprises from about 0.5–30 mg/ml of the compound and about 100–200 mg/ml of a phospholipid in water.

19. The composition of claim 18 which further includes about 5 mg/ml of cholesterol.

20. A method of inhibiting replication and/or proliferation of a hepatitis C ("HC") virion, comprising the step of contacting an HC virion with an amount of a compound according to structural formula (I):

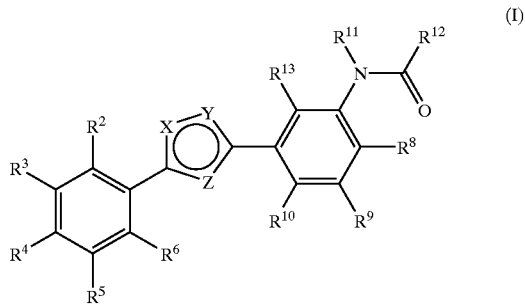

including the pharmaceutically acceptable salts, hydrates, solvates, N-oxides and prodrugs thereof, wherein:

X and Y are each, independently of one another, N or O, provided that X and Y are not both O;

Z is N or —CH—, provided that Z is —CH— when X and Y are both N;

R², R³, R⁴, R⁵, R⁶, R⁸, R⁹, R¹⁰ and R¹³ are each, independently of one another, selected from the group consisting of hydrogen, —OH, —SH, —CN, —NO₂, halo, fluoro, chloro, bromo, iodo, lower alkyl, substituted lower alkyl, lower heteroalkyl, substituted lower heteroalkyl, cycloalkyl, substituted cycloalkyl, cycloheteroalkyl, substituted cycloheteroalkyl, lower haloalkyl, monohalomethyl, dihalomethyl, trihalomethyl, trifluoromethyl, lower alkylthio, substituted lower alkylthio, lower alkoxy, substituted lower alkoxy, methoxy, substituted methoxy, lower heteroalkoxy, substituted lower heteroalkoxy, cycloalkoxy, substituted cycloalkoxy, cycloheteroalkoxy, substituted cycloheteroalkoxy, lower haloalkoxy, monohalomethoxy, dihalomethoxy, trihalomethoxy, trifluoromethoxy, amino, lower di- or monoalkylamino, substituted lower di- or monoalkylamino, aryl, substituted aryl, aryloxy, substituted aryloxy, phenoxy, substituted phenoxy, arylalkyl, substituted arylalkyl, arylalkyloxy, substituted arylalkyloxy, benzyl, benzyloxy, heteroaryl, substituted heteroaryl, heteroaryloxy, substituted heteroaryloxy, heteroarylalkyl, substituted heteroarylalkyl, heteroarylalkyloxy, substituted heteroarylalkyloxy, carboxyl, lower alkoxycarbonyl, substituted lower alkoxycarbonyl, aryloxycarbonyl, substituted aryloxycarbonyl, arylalkyloxycarbonyl, substituted arylalkyloxycarbonyl, carbamate, substituted carbamate, carbamoyl, substituted carbamoyl, sulfamoyl, substituted sulfamoyl and a group of the formula —L—$R^{14}$, where "L" is a linker and $R^{14}$ is cycloalkyl, substituted cycloalkyl, cycloheteroalkyl or substituted cycloheteroalkyl, provided that at least one of $R^2$ or $R^6$ is other than hydrogen;

$R^{11}$ is hydrogen or lower alkyl; and $R^{12}$ is monohalomethyl or dihalomethyl effective to inhibit replication and/or proliferation of the HC virion.

21. The method of claim 20 which is practiced in vitro.

22. The method of claim 20 which is practiced in viva.

23. A method of treating an HCV infection, comprising the step of administering to a subject infected with HCV an amount of a compound according to structural formula (I) effective to treat the infection:

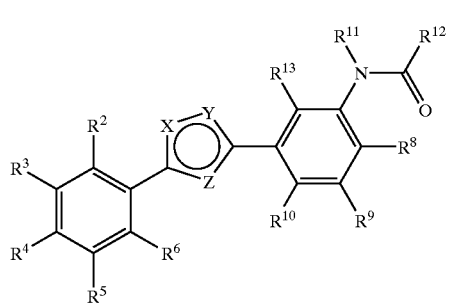

(I)

including the pharmaceutically acceptable salts, hydrates, solvates, N-oxides and prodrugs thereof, wherein:

X and Y are each, independently of one another, N or O, provided that X and Y are not both O;

Z is N or —CH—, provided that Z is —CH— when X and Y are both N;

$R^2$, $R^3$, $R^4$, $R^5$, $R^6$, $R^8$, $R^9$, $R^{10}$ and $R^{13}$ are each, independently of one another, selected from the group consisting of hydrogen, —OH, —SH, —CN, —$NO_2$, halo, fluoro, chloro, bromo, iodo, lower alkyl, substituted lower alkyl, lower heteroalkyl, substituted lower heteroalkyl, cycloalkyl, substituted cycloalkyl, cycloheteroalkyl, substituted cycloheteroalkyl, lower haloalkyl, monohalomethyl, dihalomethyl, trihalomethyl, trifluoromethyl, lower alkylthio, substituted lower alkylthio, lower alkoxy, substituted lower alkoxy, methoxy, substituted methoxy, lower heteroalkoxy, substituted lower heteroalkoxy, cycloalkoxy, substituted cycloalkoxy, cycloheteroalkoxy, substituted cycloheteroalkoxy, lower haloalkoxy, monohalomethoxy, dihalomethoxy, trihalomethoxy, trifluoromethoxy, amino, lower di- or monoalkylamino, substituted lower di- or monoalkylamino, aryl, substituted aryl, aryloxy, substituted aryloxy, phenoxy, substituted phenoxy, arylalkyl, substituted arylalkyl, arylalkyloxy, substituted arylalkyloxy, benzyl, benzyloxy, heteroaryl, substituted heteroaryl, heteroaryloxy, substituted heteroaryloxy, heteroarylalkyl, substituted heteroarylalkyl, heteroarylalkyloxy, substituted heteroarylalkyloxy, carboxyl, lower alkoxycarbonyl, substituted lower alkoxycarbonyl, aryloxycarbonyl, substituted aryloxycarbonyl, arylalkyloxycarbonyl, substituted arylalkyloxycarbonyl, carbamate, substituted carbamate, carbamoyl, substituted carbamoyl, sulfamoyl, substituted sulfamoyl and a group of the formula —L—$R^{14}$, where "L" is a linker and $R^{14}$ is cycloalkyl, substituted cycloalkyl, cycloheteroalkyl or substituted cycloheteroalkyl, provided that at least one of $R^2$ or $R^6$ is other than hydrogen;

$R^{11}$ is hydrogen or lower alkyl; and $R^{12}$ is monohalomethyl or dihalomethyl.

24. The method of claim 23, wherein the subject is a human.

25. The method of claim 23, wherein the compound is administered in an amount of about 0.1 mg/kg/day to 200 mg/kg/day.

26. The method of claim 23, wherein the compound is administered in an amount of about 10 mg/kg/day to 100 mg/kg/day.

27. The method of claim 23, wherein the compound is administered orally, intravenously or subcutaneously.

28. The method of claim 23 in which the compound is administered in the form of a pharmaceutical composition comprising the compound and a pharmaceutical vehicle.

29. The method of claim 28 in which the pharmaceutical composition is a liposome suspension.

30. The method of claim 29 in which the liposome suspension comprises from about 0.5–30 mg/l of the compound and about 100–200mg/ml of a phospholipid in water.

31. The method of claim 30 in which the liposome suspension further includes about 5 mg/ml cholesterol.

32. A method of synthesizing a substituted diphenyl heterocycle compound according to structural formula (I):

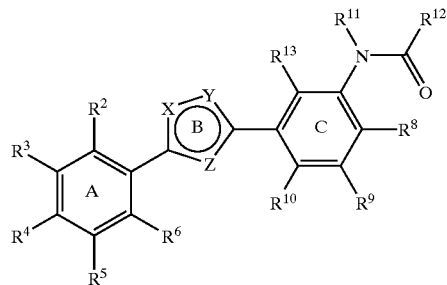

including the pharmaceutically acceptable salts, hydrates, solvates, N-oxides and prodrugs thereof, wherein:

X and Y are each, independently of one another, N or O, provided that X and Y are not both O;

Z is N or —CH—, provided that Z is —CH— when X and Y are both N;

$R^2$, $R^3$, $R^4$, $R^5$, $R^6$, $R^8$, $R^9$, $R^{10}$ and $R^{13}$ are each, independently of one another, selected from the group consisting of hydrogen, —OH, —SH, —CN, —$NO_2$, halo, fluoro, chloro, bromo, iodo, lower alkyl, substituted lower alkyl, lower heteroalkyl, substituted lower heteroalkyl, cycloalkyl, substituted cycloalkyl, cycloheteroalkyl, substituted cycloheteroalkyl, lower haloalkyl, monohalomethyl, dihalomethyl, trihalomethyl, trifluoromethyl, lower alkylthio, substituted lower alkylthio, lower alkoxy, substituted lower alkoxy, methoxy, substituted methoxy, lower heteroalkoxy, substituted lower heteroalkoxy, cycloalkoxy, substituted cycloalkoxy, cycloheteroalkoxy, substituted cycloheteroalkoxy, lower haloalkoxy, monohalomethoxy, dihalomethoxy, trihalomethoxy, trifluoromethoxy, amino, lower di- or monoalkylamino, substituted lower di- or monoalkylamino, aryl, substituted aryl, aryloxy, substituted aryloxy, phenoxy, substituted phenoxy, arylalkyl, substituted arylalkyl, arylalkyloxy, substituted arylalkyloxy, benzyl, benzyloxy, heteroaryl, substituted heteroaryl, heteroaryloxy, substituted heteroaryloxy, heteroarylalkyl, substituted heteroarylalkyl, heteroarylalkyloxy, substituted heteroarylalkyloxy, carboxyl, lower alkoxycarbonyl, substituted lower alkoxycarbonyl, aryloxycarbonyl, substituted aryloxycarbonyl, arylalkyloxycarbonyl, substituted arylalkyloxycarbonyl, carbamate, substituted carbamate, carbamoyl, substituted carbamoyl, sulfamoyl, substituted sulfamoyl and a group of the formula —L—$R^{14}$, where "L" is a linker and $R^{14}$ is cycloalkyl, substituted cycloalkyl, cycloheteroalkyl or substituted cycloheteroalkyl, provided that at least one of $R^2$ or $R^6$ is other than hydrogen;

$R^{11}$ is a lower alkyl; and $R^{12}$ is monohalomethyl or dihalomethyl, comprising the steps of (1) alkylating a compound according to structural formula:

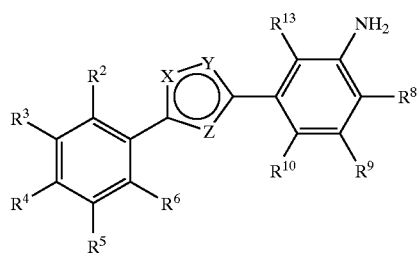

with $R^{11}$-halide and (2) acylating the product of (1) with LG—C(O)—$R^{12}$, where LG is a leaving group or an activating group, thereby yielding a compound according to structural formula (I).

33. A method of synthesizing a substituted diphenyl heterocycle compound according to structural formula (I):

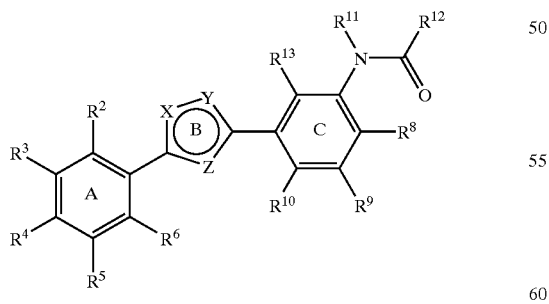

including the pharmaceutically acceptable salts, hydrates, solvates, N-oxides and prodrugs thereof, wherein:

X and Y are each, independently of one another, N or O, provided that X and Y are not both O;

Z is N or —CH—, provided that Z is —CH— when X and Y are both N;

$R^2$, $R^3$, $R^4$, $R^5$, $R^6$, $R^8$, $R^9$, $R^{10}$ and $R^{13}$ are each, independently of one another, selected from the group consisting of hydrogen, —OH, —SH, —ON, —$NO_2$, halo, fluoro, chloro, bromo, iodo, lower alkyl, substituted lower alkyl, lower heteroalkyl, substituted lower heteroalkyl, cycloalkyl, substituted cycloalkyl, cycloheteroalkyl, substituted cycloheteroalkyl, lower haloalkyl, monohalomethyl, dihalomethyl, trihalomethyl, trifluoromethyl, lower alkylthio, substituted lower alkylthio, lower alkoxy, substituted lower alkoxy, methoxy, substituted methoxy, lower heteroalkoxy, substituted lower heteroalkoxy, cycloalkoxy, substituted cycloalkoxy, cycloheteroalkoxy, substituted cycloheteroalkoxy, lower haloalkoxy, monohalomethoxy, dihalomethoxy, trihalomethoxy, trifluoromethoxy, amino, lower di- or monoalkylamino, substituted lower di- or monoalkylamino, aryl, substituted aryl, aryloxy, substituted aryloxy, phenoxy, substituted phenoxy, arylalkyl, substituted arylalkyl, arylalkyloxy, substituted arylalkyloxy, benzyl, benzyloxy, heteroaryl, substituted heteroaryl, heteroaryloxy, substituted heteroaryloxy, heteroarylalkyl, substituted heteroarylalkyl, heteroarylalkyloxy, substituted heteroarylalkyloxy, carboxyl, lower alkoxycarbonyl, substituted lower alkoxycarbonyl, aryloxycarbonyl, substituted aryloxycarbonyl, arylalkyloxycarbonyl, substituted arylalkyloxycarbonyl, carbamate, substituted carbamate, carbamoyl, substituted carbamoyl, sulfamoyl, substituted sulfamoyl and a group of the formula —L—$R^{14}$, where "L" is a linker and $R^{14}$ is cycloalkyl, substituted cycloalkyl, cycloheteroalkyl or substituted cycloheteroalkyl, provided that at least one of $R^2$ or $R^6$ is other than hydrogen;

$R^{11}$ is hydrogen; and $R^{12}$ is monohalomethyl or dihalomethyl, comprising the steps of (1) acylating a compound according to structural formula:

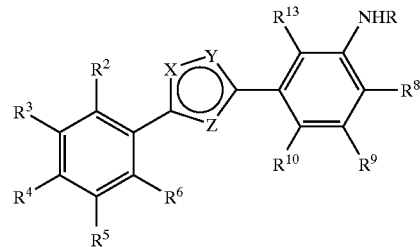

wherein R is a protecting group;

with LG—C(O)—$R^{12}$, where LG is a leaving group or an activating group and (2) deprotecting the product of step (1), thereby yielding a compound according to structural formula (I).

34. A compound according to structural formula (I):

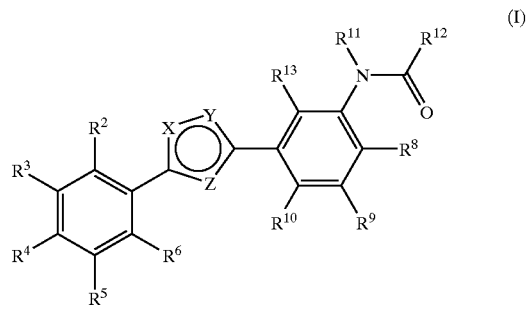

(I)

le;2qwherein X, Y, Z, $R^2$, $R^3$, $R^4$, $R^5$, $R^6$, $R^8$, $R^9$, $R^{10}$, $R^{11}$, $R^{12}$ and $R^{13}$ are as defined in Table 1 including the pharmaceutically acceptable salts, hydrates, solvates, N-oxides and prodrugs thereof wherein Table 1 comprises:

TABLE 1

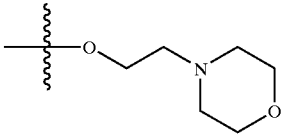

| Cmpd | Replicon/Western | X | Y | Z | $R^2$ | $R^3$ | $R^4$ | $R^5$ |
|---|---|---|---|---|---|---|---|---|
| 1 | +/+ | N | O | CH | Cl | H | H | H |
| 3 | −/+ | N | O | CH | Cl | Cl | H | H |
| 5 | +/+ | O | N | CH | Cl | H | H | H |
| 7 | +/+ | N | O | CH | Cl | H | H | H |
| 9 | +/+ | N | O | CH | Cl | H | H | H |
| 11 | +/+ | N | O | CH | F | H | H | H |
| 13 | +/+ | N | O | CH | Cl | H | H | H |
| 15 | +/+ | N | O | CH | F | H | H | Me |
| 21 | +/+ | N | O | CH | F | H | H | H |
| 23 | + | N | O | CH | Me | H | 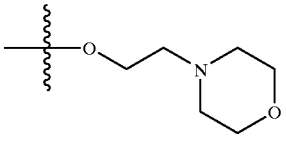 | H |
| 25 | | N | O | N | Cl | H | H | H |
| 27 | +/+ | N | O | CH | Cl | H | H | H |
| 29 | + | N | O | CH | Cl | H | H | H |
| 31 | + | N | O | CH | Cl | H | H | H |
| 33 | + | N | O | CH | $CF_3$ | H | H | H |
| 35 | + | N | O | CH | $CF_3$ | H | H | H |
| 37 | +/+ | N | O | CH | $CF_3$ | H | H | H |
| 39 | + | N | O | CH | Cl | H | H | H |
| 41 | + | N | O | CH | $CF_3$ | H | H | H |
| 43 | + | N | O | CH | F | H | H | H |
| 45 | + | N | O | CH | $OCHF_2$ | H | H | H |
| 47 | + | N | O | CH | Me | H | H | H |
| 49 | + | N | O | CH | I | H | H | H |
| 51 | + | N | O | CH | F | Me | H | H |
| 53 | + | N | O | CH | F | H | H | F |
| 57 | + | N | O | CH | Cl | H | H | H |
| 61 | + | N | O | CH | OEt | H | H | H |
| 63 | + | N | O | CH | iPr | H | H | H |
| 65 | + | N | O | CH | Cl | H | $N(Me)_2$ | H |
| 67 | + | N | O | CH | Cl | H | H | H |
| 69 | + | N | O | CH | Me | H | Me | H |
| 73 | + | N | O | CH | Cl | H | 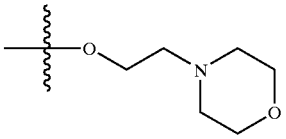 | H |
| 75 | −/+ | N | O | CH | Cl | H | 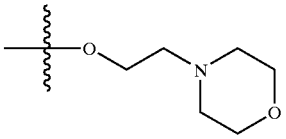 | H |
| 77 | + | N | O | CH | $CF_3$ | H | H | H |
| 79 | + | N | O | CH | Cl | H | H | H |

TABLE 1-continued

| | | | | | | | | |
|---|---|---|---|---|---|---|---|---|
| 81 | + | N | O | CH | Cl | H | H | H |
| 83 | + | N | O | CH | Cl | H | H | H |
| 85 | + | N | O | CH | $CF_3$ | H | H | H |
| 87 | + | O | N | N | Cl | H | H | H |
| 89 | + | N | O | CH | $CF_3$ | H | H | H |
| 91 | + | N | O | CH | Me | H | H | H |
| 93 | + | N | O | CH | $CF_3$ | H | H | H |
| 95 | + | N | O | CH | Cl | H | H | H |
| 97 | + | N | O | CH | Cl | H | H | H |
| 99 | + | N | O | CH | Cl | H | H | H |
| 101 | +/− | N | O | CH | Cl | H | H | H |
| 103 | + | N | O | CH | Cl | H | H | H |
| 105 | + | N | O | CH | $CF_3$ | H | H | H |
| 107 | + | N | O | CH | Cl | H | H | H |
| 109 | + | N | O | CH | $CF_3$ | H | H | H |
| 111 | + | N | O | CH | Cl | H | H | H |
| 113 | + | N | O | CH | $OCF_3$ | H | H | H |
| 115 | + | N | O | CH | C(O)OMe | H | H | H |
| 117 | + | N | O | CH | Cl | H | H | H |
| 119 | + | N | O | CH | O-iPr | H | H | H |
| 121 | + | N | O | CH | iPr | H | H | H |
| 123 | + | N | O | CH | Ph | H | H | H |
| 125 | + | N | O | CH | Cl | H | 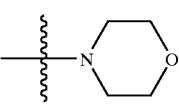 | H |
| 127 | + | N | O | CH | Cl | H | H | H |
| 129 | + | N | O | CH | 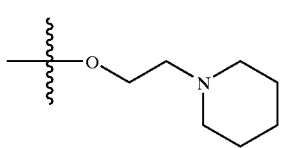 | H | H | H |
| 131 | + | N | O | CH | Cl | H | H | H |
| 132 | + | N | O | CH | Cl | H | H | H |
| 135 | −/− | N | O | CH | Cl | C(O)OMe | H | H |
| 137 | − | N | O | CH | Cl | H | H | Cl |
| 139 | − | N | O | CH | Cl | C(O)OH | H | H |
| 141 | − | N | O | CH | Cl | H | H | $CF_3$ |
| 143 | − | N | O | CH | Cl | H | Cl | H |
| 145 | − | N | O | CH | Cl | H | H | H |
| 149 | − | N | O | CH | F | Me | H | H |
| 151 | − | N | O | CH | Cl | H | H | H |
| 153 | − | N | O | CH | F | H | H | H |
| 155 | | N | O | CH | H | H | H | H |
| 157 | − | N | O | CH | C(O)OH | H | H | H |
| 159 | | N | O | CH | H | H | Cl | H |
| 161 | | N | O | CH | H | H | H | H |
| 163 | −/− | N | O | CH | Me | Me | H | H |
| 165 | − | N | O | CH | Cl | H | H | H |
| 167 | − | N | O | CH | Cl | H | H | H |
| 169 | − | N | O | CH | Cl | H | H | H |
| 171 | − | N | O | CH | Cl | H | H | H |
| 173 | + | N | O | CH | Cl | H | H | H |
| 175 | | N | O | CH | Cl | H | H | H |
| 177 | | N | O | CH | Cl | H | H | H |
| 179 | | N | O | CH | Br | H | H | H |
| 181 | | N | O | CH | Cl | H | H | H |
| 183 | | N | O | CH | OMe | H | H | H |
| 185 | | N | O | CH | Br | H | H | H |
| 187 | | N | O | CH | Cl | H | H | H |
| 189 | | N | N | CH | Cl | H | H | H |

| Cmpd | $R^6$ | $R^8$ | $R^9$ | $R^{10}$ | $R^{11}$ | $R^{12}$ | $R^{13}$ |
|---|---|---|---|---|---|---|---|
| 1 | Cl | F | H | H | H | $CHCl_2$ | H |
| 3 | H | H | H | H | H | $CHCl_2$ | H |
| 5 | Cl | H | H | H | H | $CHCl_2$ | H |
| 7 | 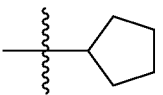 | H | H | H | H | $CHCl_2$ | H |

TABLE 1-continued

| # | R1 | | | | | | |
|---|---|---|---|---|---|---|---|
| 9 | Cl | H | H | H | H | CHCl$_2$ | H |
| 11 | SMe | H | H | H | H | CHCl$_2$ | H |
| 13 | Cl | H | H | F | H | CHCl$_2$ | H |
| 15 | Cl | H | H | H | H | CHCl$_2$ | H |
| 21 | ⸻S(=O)$_2$-N-morpholine | H | H | H | H | CHCl$_2$ | H |
| 23 | Me | H | H | H | H | CHCl$_2$ | H |
| 25 | Cl | H | H | H | H | CHCl$_2$ | H |
| 27 | F | H | H | H | H | CHCl$_2$ | H |
| 29 | Cl | H | H | H | H | CHBr$_2$ | H |
| 31 | Me | H | H | H | H | CHCl$_2$ | H |
| 33 | H | H | H | H | H | CHCl$_2$ | H |
| 35 | OH | H | H | H | H | CHCl$_2$ | H |
| 37 | ⸻N-morpholine | H | H | H | H | CHCl$_2$ | H |
| 39 | iPr | H | H | H | H | CHCl$_2$ | H |
| 41 | F | H | H | H | H | CHCl$_2$ | H |
| 43 | OMe | H | H | H | H | CHCl$_2$ | H |
| 45 | H | H | H | H | H | CHCl$_2$ | H |
| 47 | Me | H | H | H | H | CHCl$_2$ | H |
| 49 | F | H | H | H | H | CHCl$_2$ | H |
| 51 | Cl | H | H | H | H | CHCl$_2$ | H |
| 53 | Cl | H | H | H | H | CHCl$_2$ | H |
| 57 | Cl | H | H | H | Me | CHCl$_2$ | H |
| 61 | H | H | H | H | H | CHCl$_2$ | H |
| 63 | H | H | H | H | H | CHCl$_2$ | H |
| 65 | Cl | H | H | H | H | CHCl$_2$ | H |
| 67 | Cl | H | H | H | H | CH$_2$Cl | H |
| 69 | Me | H | H | H | H | CHCl$_2$ | H |
| 73 | Cl | H | H | H | H | CHCl$_2$ | H |
| 75 | Cl | H | H | H | H | CHCl$_2$ | H |
| 77 | OMe | H | H | H | H | CHCl$_2$ | H |
| 79 | ⸻cyclopropyl | H | H | H | H | CHCl$_2$ | H |
| 81 | OMe | H | H | H | H | CHCl$_2$ | H |
| 83 | OH | H | H | H | H | CHCl$_2$ | H |
| 85 | Me | H | H | H | H | CHCl$_2$ | H |
| 87 | Cl | H | H | H | H | CHCl$_2$ | H |
| 89 | ⸻cyclopropyl | H | H | H | H | CHCl$_2$ | H |
| 91 | OMe | H | H | H | H | CHCl$_2$ | H |
| 93 | iPr | H | H | H | H | CHCl$_2$ | H |
| 95 | ⸻O-CH$_2$CH$_2$-N-morpholine | H | H | H | H | CHCl$_2$ | H |
| 97 | ⸻cyclopentyl | H | H | H | H | CHCl$_2$ | H |

TABLE 1-continued

| | | | | | | | | |
|---|---|---|---|---|---|---|---|---|
| 99 | 4-methylpiperazin-1-yl | H | H | H | H | CHCl$_2$ | H |
| 101 | Cl | H | H | H | H | CH$_2$I | H |
| 103 | nBu | H | H | H | H | CHCl$_2$ | H |
| 105 | cyclopentyl | H | H | H | H | CHCl$_2$ | H |
| 107 | Cl | H | H | morpholin-4-ylsulfonyl | H | CHCl$_2$ | H |
| 109 | 4-methylpiperazin-1-yl | H | H | H | H | CHCl$_2$ | H |
| 111 | cyclohexyl | H | H | H | H | CHCl$_2$ | H |
| 113 | H | H | H | H | H | CHCl$_2$ | H |
| 115 | H | H | H | H | H | CHCl$_2$ | H |
| 117 | imidazol-1-yl | H | H | H | H | CHCl$_2$ | H |
| 119 | H | H | H | H | H | CHCl$_2$ | H |
| 121 | iPr | H | H | H | H | CHCl$_2$ | H |
| 123 | H | H | H | H | H | CHCl$_2$ | H |
| 125 | H | H | H | H | H | CHCl$_2$ | H |
| 127 | Cl | H | H | OMe | H | CHCl$_2$ | H |
| 129 | H | H | H | H | H | CHCl$_2$ | H |
| 131 | N-methyl-N-(2-dimethylaminoethyl)amino | H | H | H | H | CHCl$_2$ | H |
| 132 | 3-(dimethylamino)pyrrolidin-1-yl | H | H | H | H | CHCl$_2$ | H |
| 135 | Cl | H | H | H | H | CHCl$_2$ | H |
| 137 | Cl | H | H | H | H | CHCl$_2$ | H |
| 139 | Cl | H | H | H | H | CHCl$_2$ | H |
| 141 | H | H | H | H | H | CHCl$_2$ | H |
| 143 | 2-(morpholin-4-yl)ethoxy | H | H | H | H | CHCl$_2$ | H |
| 145 | Cl | H | H | H | H | CHF$_2$ | H |
| 149 | F | H | H | H | H | CHCl$_2$ | H |

TABLE 1-continued

| | | | | | | | | |
|---|---|---|---|---|---|---|---|---|
| 151 | *piperidine-N-CO2Et* | H | H | H | H | CHCl$_2$ | H |
| 153 | SO$_2$Me | H | H | H | H | CHCl$_2$ | H |
| 155 | *CH$_2$-morpholine* | H | H | H | H | CHCl$_2$ | H |
| 157 | H | H | H | H | H | CHCl$_2$ | H |
| 159 | Cl | H | H | H | H | CHCl$_2$ | H |
| 161 | OBz | H | H | H | H | CHCl$_2$ | H |
| 163 | H | H | H | H | H | CHCl$_2$ | H |
| 165 | Cl | Me | H | H | H | CHCl$_2$ | H |
| 167 | Cl | H | H | H | H | CHCl$_2$ | Me |
| 169 | Cl | *morpholine* | H | H | H | CHCl$_2$ | H |
| 171 | Cl | *OCH$_2$CH$_2$-morpholine* | H | H | H | CHCl$_2$ | H |
| 173 | Cl | OMe | H | H | H | CHCl$_2$ | H |
| 175 | *4-piperidinopiperidine* | H | H | H | H | CHCl$_2$ | H |
| 177 | H | H | H | H | H | CHCl$_2$ | H |
| 179 | H | H | H | H | H | CHCl$_2$ | H |
| 181 | NO$_2$ | H | H | H | H | CHCl$_2$ | H |
| 183 | H | H | H | H | H | CHCl$_2$ | H |
| 185 | Cl | H | H | H | H | CHCl$_2$ | H |
| 187 | *4-aminopiperidine* | H | H | H | H | CHCl$_2$ | H |
| 189 | Cl | H | H | H | H | CHCl$_2$ | H |

\* \* \* \* \*

UNITED STATES PATENT AND TRADEMARK OFFICE
CERTIFICATE OF CORRECTION

PATENT NO.       : 6,759,538 B2  
APPLICATION NO.  : 10/286017  
DATED            : July 6, 2004  
INVENTOR(S)      : Rajinder Singh et al.

Page 1 of 12

It is certified that error appears in the above-identified patent and that said Letters Patent is hereby corrected as shown below:

Replace Table 1 in claim 34 with the following Table 1:

TABLE 1

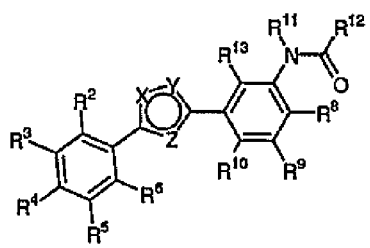

| Cmpd | X | Y | Z  | $R^2$ | $R^3$ | $R^4$ | $R^5$ | $R^6$          | $R^8$       | $R^9$ | $R^{10}$ | $R^{11}$ | $R^{12}$ | $R^{13}$ |
|------|---|---|----|-------|-------|-------|-------|----------------|-------------|-------|----------|----------|----------|----------|
| 1    | N | O | CH | Cl    | H     | H     | H     | Cl             | F           | H     | H        | H        | $CHCl_2$ | H        |
| 3    | N | O | CH | Cl    | Cl    | H     | H     | H              | H           | H     | H        | H        | $CHCl_2$ | H        |
| 5    | O | N | CH | Cl    | H     | H     | H     | Cl             | H           | H     | H        | H        | $CHCl_2$ | H        |
| 7    | N | O | CH | Cl    | H     | H     | H     | -N(morpholine) | H           | H     | H        | H        | $CHCl_2$ | H        |
| 11   | N | O | CH | F     | H     | H     | H     | SMe            | H           | H     | H        | H        | $CHCl_2$ | H        |
| 13   | N | O | CH | Cl    | H     | H     | H     | Cl             | H           | H     | F        | H        | $CHCl_2$ | H        |
| 15   | N | O | CH | F     | H     | H     | Me    | Cl             | H           | H     | H        | H        | $CHCl_2$ | H        |
| 21   | N | O | CH | F     | H     | H     | H     | $SO_2$-morpholine | H        | H     | H        | H        | $CHCl_2$ | H        |
| 23   | N | O | CH | Me    | H     | morpholinoethoxy | H | Me          | H           | H     | H        | H        | $CHCl_2$ | H        |
| 25   | N | O | N  | Cl    | H     | H     | H     | Cl             | H           | H     | H        | H        | $CHCl_2$ | H        |

UNITED STATES PATENT AND TRADEMARK OFFICE
CERTIFICATE OF CORRECTION

PATENT NO. : 6,759,538 B2
APPLICATION NO. : 10/286017
DATED : July 6, 2004
INVENTOR(S) : Rajinder Singh et al.

It is certified that error appears in the above-identified patent and that said Letters Patent is hereby corrected as shown below:

| 27 | N | O | CH | Cl | H | H | H | F | H | H | H | CHCl$_2$ | H |
|---|---|---|---|---|---|---|---|---|---|---|---|---|---|
| 29 | N | O | CH | Cl | H | H | H | Cl | H | H | H | CHBr$_2$ | H |
| 31 | N | O | CH | Cl | H | H | H | Me | H | H | H | CHCl$_2$ | H |
| 33 | N | O | CH | CF$_3$ | H | H | H | H | H | H | H | CHCl$_2$ | H |
| 35 | N | O | CH | CF$_3$ | H | H | H | OH | H | H | H | CHCl$_2$ | H |
| 37 | N | O | CH | CF$_3$ | H | H | H |  | H | H | H | CHCl$_2$ | H |
| 39 | N | O | CH | Cl | H | H | H | iPr | H | H | H | CHCl$_2$ | H |
| 41 | N | O | CH | CF$_3$ | H | H | H | F | H | H | H | CHCl$_2$ | H |
| 43 | N | O | CH | F | H | H | H | OMe | H | H | H | CHCl$_2$ | H |
| 45 | N | O | CH | OCHF$_2$ | H | H | H | H | H | H | H | CHCl$_2$ | H |
| 47 | N | O | CH | Me | H | H | H | Me | H | H | H | CHCl$_2$ | H |
| 49 | N | O | CH | I | H | H | H | F | H | H | H | CHCl$_2$ | H |
| 51 | N | O | CH | F | Me | H | H | Cl | H | H | H | CHCl$_2$ | H |
| 53 | N | O | CH | F | H | H | F | Cl | H | H | H | CHCl$_2$ | H |
| 57 | N | O | CH | Cl | H | H | H | Cl | H | H | Me | CHCl$_2$ | H |
| 61 | N | O | CH | OEt | H | H | H | H | H | H | H | CHCl$_2$ | H |
| 63 | N | O | CH | iPr | H | H | H | H | H | H | H | CHCl$_2$ | H |
| 65 | N | O | CH | Cl | H | N(Me)$_2$ | H | Cl | H | H | H | CHCl$_2$ | H |
| 67 | N | O | CH | Cl | H | H | H | Cl | H | H | H | CH$_2$Cl | H |
| 69 | N | O | CH | Me | H | Me | H | Me | H | H | H | CHCl$_2$ | H |

UNITED STATES PATENT AND TRADEMARK OFFICE
CERTIFICATE OF CORRECTION

PATENT NO.       : 6,759,538 B2
APPLICATION NO.  : 10/286017
DATED            : July 6, 2004
INVENTOR(S)      : Rajinder Singh et al.

It is certified that error appears in the above-identified patent and that said Letters Patent is hereby corrected as shown below:

| 73 | N | O | CH | Cl | H |  | H | Cl | H | H | H | H | CHCl$_2$ | H |
|---|---|---|---|---|---|---|---|---|---|---|---|---|---|---|
| 75 | N | O | CH | Cl | H | 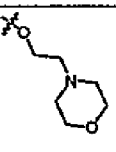 | H | Cl | H | H | H | H | CHCl$_2$ | H |
| 77 | N | O | CH | CF$_3$ | H | H | H | OMe | H | H | H | H | CHCl$_2$ | H |
| 79 | N | O | CH | Cl | H | H | H |  | H | H | H | H | CHCl$_2$ | H |
| 81 | N | O | CH | Cl | H | H | H | OMe | H | H | H | H | CHCl$_2$ | H |
| 83 | N | O | CH | Cl | H | H | H | OH | H | H | H | H | CHCl$_2$ | H |
| 85 | N | O | CH | CF$_3$ | H | H | H | Me | H | H | H | H | CHCl$_2$ | H |
| 87 | O | N | N | Cl | H | H | H | Cl | H | H | H | H | CHCl$_2$ | H |
| 89 | N | O | CH | CF$_3$ | H | H | H |  | H | H | H | H | CHCl$_2$ | H |
| 91 | N | O | CH | Me | H | H | H | OMe | H | H | H | H | CHCl$_2$ | H |
| 93 | N | O | CH | CF$_3$ | H | H | H | iPr | H | H | H | H | CHCl$_2$ | H |
| 95 | N | O | CH | Cl | H | H | H | 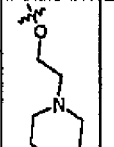 | H | H | H | H | CHCl$_2$ | H |
| 97 | N | O | CH | Cl | H | H | H |  | H | H | H | H | CHCl$_2$ | H |

UNITED STATES PATENT AND TRADEMARK OFFICE
CERTIFICATE OF CORRECTION

PATENT NO. : 6,759,538 B2
APPLICATION NO. : 10/286017
DATED : July 6, 2004
INVENTOR(S) : Rajinder Singh et al.

It is certified that error appears in the above-identified patent and that said Letters Patent is hereby corrected as shown below:

| | | | | | | | | | | | | | |
|---|---|---|---|---|---|---|---|---|---|---|---|---|---|
| 99 | N | O | CH | Cl | H | H | H |  | H | H | H | H | CHCl$_2$ | H |
| 101 | N | O | CH | Cl | H | H | H | Cl | H | H | H | H | CH$_2$I | H |
| 103 | N | O | CH | Cl | H | H | H | nBu | H | H | H | H | CHCl$_2$ | H |
| 105 | N | O | CH | CF$_3$ | H | H | H |  | H | H | H | H | CHCl$_2$ | H |
| 107 | N | O | CH | Cl | H | H | H | Cl | H | H | 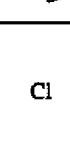 | H | CHCl$_2$ | H |
| 109 | N | O | CH | CF$_3$ | H | H | H |  | H | H | H | H | CHCl$_2$ | H |
| 111 | N | O | CH | Cl | H | H | H |  | H | H | H | H | CHCl$_2$ | H |
| 113 | N | O | CH | OCF$_3$ | H | H | H | H | H | H | H | H | CHCl$_2$ | H |
| 115 | N | O | CH | C(O)OMe | H· | H | H | H | H | H | H | H | CHCl$_2$ | H |
| 117 | N | O | CH | Cl | H | H | H |  | H | H | H | H | CHCl$_2$ | H |
| 119 | N | O | CH | O-iPr | H | H | H | H | H | H | H | H | CHCl$_2$ | H |
| 121 | N | O | CH | iPr | H | H | H | iPr | H | H | H | H | CHCl$_2$ | H |
| 123 | N | O | CH | Ph | H | H | H | H | H | H | H | H | CHCl$_2$ | H |

UNITED STATES PATENT AND TRADEMARK OFFICE
CERTIFICATE OF CORRECTION

PATENT NO. : 6,759,538 B2  Page 5 of 12
APPLICATION NO. : 10/286017
DATED : July 6, 2004
INVENTOR(S) : Rajinder Singh et al.

It is certified that error appears in the above-identified patent and that said Letters Patent is hereby corrected as shown below:

| 125 | N | O | CH | Cl | H |  | H | H | H | H | H | H | CHCl$_2$ | H |
| --- | --- | --- | --- | --- | --- | --- | --- | --- | --- | --- | --- | --- | --- | --- |
| 127 | N | O | CH | Cl | H | H | H | Cl | H | H | OMe | H | CHCl$_2$ | H |
| 129 | N | O | CH |  | H | H | H | H | H | H | H | H | CHCl$_2$ | H |
| 131 | N | O | CH | Cl | H | H | H |  | H | H | H | H | CHCl$_2$ | H |
| 132 | N | O | CH | Cl | H | H | H |  | H | H | H | H | CHCl$_2$ | H |
| 135 | N | O | CH | Cl | C(O)OMe | H | H | Cl | H | H | H | H | CHCl$_2$ | H |
| 137 | N | O | CH | Cl | H | H | Cl | Cl | H | H | H | H | CHCl$_2$ | H |
| 139 | N | O | CH | Cl | C(O)OH | H | H | Cl | H | H | H | H | CHCl$_2$ | H |
| 141 | N | O | CH | Cl | H | H | CF$_3$ | H | H | H | H | H | CHCl$_2$ | H |
| 143 | N | O | CH | Cl | H | Cl | H |  | H | H | H | H | CHCl$_2$ | H |

UNITED STATES PATENT AND TRADEMARK OFFICE
CERTIFICATE OF CORRECTION

PATENT NO. : 6,759,538 B2
APPLICATION NO. : 10/286017
DATED : July 6, 2004
INVENTOR(S) : Rajinder Singh et al.

It is certified that error appears in the above-identified patent and that said Letters Patent is hereby corrected as shown below:

| 145 | N | O | CH | Cl | H | H | H | Cl | H | H | H | H | CHF$_2$ | H |
|---|---|---|---|---|---|---|---|---|---|---|---|---|---|---|
| 149 | N | O | CH | F | Me | H | H | F | H | H | H | H | CHCl$_2$ | H |
| 151 | N | O | CH | Cl | H | H | H | 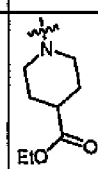 | H | H | H | H | CHCl$_2$ | H |
| 153 | N | O | CH | F | H | H | H | SO$_2$Me | H | H | H | H | CHCl$_2$ | H |
| 155 | N | O | CH | H | H | H | H | 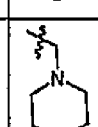 | H | H | H | H | CHCl$_2$ | H |
| 157 | N | O | CH | C(O)OH | H | H | H | H | H | H | H | H | CHCl$_2$ | H |
| 161 | N | O | CH | H | H | H | H | OBz | H | H | H | H | CHCl$_2$ | H |
| 163 | N | O | CH | Me | Me | H | H | H | H | H | H | H | CHCl$_2$ | H |
| 165 | N | O | CH | Cl | H | H | H | Cl | Me | H | H | H | CHCl$_2$ | H |
| 167 | N | O | CH | Cl | H | H | H | Cl | H | H | H | H | CHCl$_2$ | Me |
| 169 | N | O | CH | Cl | H | H | H | Cl | 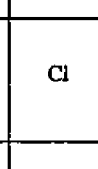 | H | H | H | CHCl$_2$ | H |
| 171 | N | O | CH | Cl | H | H | H | Cl | 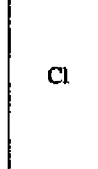 | H | H | H | CHCl$_2$ | H |
| 173 | N | O | CH | Cl | H | H | H | Cl | OMe | H | H | H | CHCl$_2$ | H |

UNITED STATES PATENT AND TRADEMARK OFFICE
CERTIFICATE OF CORRECTION

PATENT NO.      : 6,759,538 B2
APPLICATION NO. : 10/286017
DATED           : July 6, 2004
INVENTOR(S)     : Rajinder Singh et al.

It is certified that error appears in the above-identified patent and that said Letters Patent is hereby corrected as shown below:

| 175 | N | O | CH | Cl | H | H | H |  | H | H | H | H | CHCl₂ | H |
|---|---|---|---|---|---|---|---|---|---|---|---|---|---|---|
| 177 | N | O | CH | Cl | H | H | H | H | H | H | H | H | CHCl₂ | H |
| 179 | N | O | CH | Br | H | H | H | H | H | H | H | H | CHCl₂ | H |
| 181 | N | O | CH | Cl | H | H | H | NO₂ | H | H | H | H | CHCl₂ | H |
| 183 | N | O | CH | OMe | H | H | H | H | H | H | H | H | CHCl₂ | H |
| 185 | N | O | CH | Br | H | H | H | Cl | H | H | H | H | CHCl₂ | H |
| 187 | N | O | CH | Cl | H | H | H |  | H | H | H | H | CHCl₂ | H |
| 189 | N | N | CH | Cl | H | H | H | Cl | H | H | H | H | CHCl₂ | H |

Add claim 35 as follows:
    35.    The composition of claim 16 in which the compound is selected from the group consisting of:
        Compound 1: 2,2-Dichloro-N-[3-[3-(2,6-dichlorophenyl)-5-isoxazolyl]-6-fluorophenyl] Acetamide;
        Compound 3: 2,2-Dichloro-N-[3-[3-(2,3-dichlorophenyl)-5-isoxazolyl]phenyl] Acetamide;
        Compound 5: 2,2-Dichloro-N-[3-[5-(2,6-dichlorophenyl)-3-isoxazolyl]phenyl] Acetamide;
        Compound 7: 2,2-Dichloro-N-[3-[3-[2-chloro-6-(N-morpholino)phenyl)-5-isoxazolyl]phenyl] Acetamide;

UNITED STATES PATENT AND TRADEMARK OFFICE
CERTIFICATE OF CORRECTION

| | | |
|---|---|---|
| PATENT NO. | : 6,759,538 B2 | |
| APPLICATION NO. | : 10/286017 | |
| DATED | : July 6, 2004 | |
| INVENTOR(S) | : Rajinder Singh et al. | |

It is certified that error appears in the above-identified patent and that said Letters Patent is hereby corrected as shown below:

Compound 9: 2,2-Dichloro-N-[3-[3-(2,6-dichlorophenyl)-5-isoxazolyl]phenyl] Acetamide;
      Compound 11: 2,2-Dichloro-N-[3-[3-(2-fluoro-6-thiomethylphenyl)-5-isoxazolyl]phenyl] Acetamide;
      Compound 13: 2,2-Dichloro-N-[3-[3-(2,6-dichlorophenyl)-5-isoxazolyl]-4-fluorophenyl] Acetamide;
      Compound 15: 2,2-Dichloro-N-[3-[3-(2-chloro-6-fluoro-3-methylphenyl)-5-isoxazolyl]phenyl] Acetamide;
      Compound 21: 2,2-Dichloro-N-[3-[3-[2-fluoro-(6-N-morpholinosulfamoyl)phenyl]-5-isoxazolyl]-phenyl] Acetamide;
      Compound 23: 2,2-Dichloro-N-[3-[3-[2,6-dimethyl-4-(N-morpholino-2-ethyleneoxy)phenyl]-5-isoxazolyl]phenyl] Acetamide;
      Compound 25: 2,2-Dichloro-N-[3-[3-(2,6-dichlorophenyl)-5-(1,2,4-oxadiazolyl)]phenyl] Acetamide;
      Compound 27: 2,2-Dichloro-N-[3-[3-(2-chloro-6-fluorophenyl)-5-isoxazolyl]phenyl] Acetamide;
      Compound 29: 2,2-Dibromo-N-[3-[3-(2,6-dichlorophenyl)-5-isoxazolyl]phenyl] Acetamide;
      Compound 31: 2,2-Dichloro-N-[3-[3-(2-chloro-6-methylphenyl)-5-isoxazolyl]phenyl] Acetamide;
      Compound 33: 2,2-Dichloro-N-[3-[3-(2-trifluoromethylphenyl)-5-isoxazolyl]phenyl] Acetamide;
      Compound 35: 2,2-Dichloro-N-[3-[3-(2-hydroxy-6-trifluoromethylphenyl)-5-isoxazolyl]phenyl] Acetamide;
      Compound 37: 2,2-Dichloro-N-[3-[3-[2-(N-morpholino)-6-trifluoromethylphenyl)-5-isoxazolyl]phenyl] Acetamide;
      Compound 39: 2,2-Dichloro-N-[3-[3-(2-chloro-6-isopropylphenyl)-5-isoxazolyl]phenyl] Acetamide;
      Compound 41: 2,2-Dichloro-N-[3-[3-(2-fluoro-6-trifluoromethylphenyl)-5-isoxazolyl]phenyl] Acetamide;
      Compound 43: 2,2-Dichloro-N-[3-[3-(2-fluoro-6-methoxyphenyl)-5-isoxazolyl]phenyl] Acetamide;
      Compound 45: 2,2-Dichloro-N-[3-[3-(2-difluoromethoxyphenyl)-5-isoxazolyl]phenyl] Acetamide;
      Compound 47: 2,2-Dichloro-N-[3-[3-(2,6-dimethylphenyl)-5-isoxazolyl]phenyl] Acetamide;

Compound 49: 2,2-Dichloro-N-[3-[3-(2-fluoro-6-iodophenyl)-5-isoxazolyl]phenyl] Acetamide;

UNITED STATES PATENT AND TRADEMARK OFFICE
CERTIFICATE OF CORRECTION

PATENT NO.         : 6,759,538 B2
APPLICATION NO. : 10/286017
DATED                  : July 6, 2004
INVENTOR(S)       : Rajinder Singh et al.

It is certified that error appears in the above-identified patent and that said Letters Patent is hereby corrected as shown below:

Compound 51: 2,2-Dichloro-N-[3-[3-(6-chloro-2-fluoro-3-methylphenyl)-5-isoxazolyl]phenyl] Acetamide;

Compound 53: 2,2-Dichloro-N-[3-[3-(2-chloro-3,6-difluorophenyl)-5-isoxazolyl]phenyl] Acetamide;

Compound 57: 2,2-Dichloro-N-[3-[3-(2,6-dichlorophenyl)-5-isoxazolyl]phenyl]-N-methyl Acetamide;

Compound 61: 2,2-Dichloro-N-[3-[3-(2-ethoxyphenyl)-5-isoxazolyl]phenyl] Acetamide;

Compound 63: 2,2-Dichloro-N-[3-[3-(2-isopropylphenyl)-5-isoxazolyl]phenyl] Acetamide;

Compound 65: 2,2-Dichloro-N-[3-[3-(2,6-dichloro-4-dimethylaminophenyl)-5-isoxazolyl]phenyl] Acetamide;

Compound 67; 2-Chloro-N-[3-[3-(2,6-dichlorophenyl)-5-isoxazolyl]phenyl] Acetamide;

Compound 69: 2,2-Dichloro-N-[3-[3-(2,4,6-trimethylphenyl)-5-isoxazolyl]phenyl] Acetamide;

Compound 73: 2,2-Dichloro-N-[3-[3-[2,6-dichloro-4-(N-morpholinopropyleneoxy)phenyl]-5-isoxazolyl]-phenyl] Acetamide;

Compound 75: 2,2-Dichloro-N-[3-[3-[2,6-dichloro –4-(N-morpholinoethyleneoxy)phenyl]-5-isoxazolyl]-phenyl] Acetamide;

Compound 77: 2,2-Dichloro-N-[3-[3-(2-methoxy-6-trifluoromethylphenyl)-5-isoxazolyl]phenyl] Acetamide;

Compound 79: 2,2-Dichloro-N-[3-[3-(2-chloro-6-cyclopropylphenyl)-5-isoxazolyl]phenyl] Acetamide;

Compound 81: 2,2-Dichloro-N-[3-[3-(2-chloro-6-methoxyphenyl)-5-isoxazolyl]phenyl] Acetamide;

Compound 83: 2,2-Dichloro-N-[3-[3-(2-chloro-6-hydroxyphenyl)-5-isoxazolyl]phenyl] Acetamide;

Compound 85: 2,2-Dichloro-N-[3-[3-(2-methyl-6-trifluoromethylphenyl)-5-isoxazolyl]phenyl] Acetamide;

Compound 87: 2,2-Dichloro-N-[3-[5-(2,6-dichlorophenyl)-3-(1,2,4-oxadiazolyl)]phenyl] Acetamide;

Compound 89: 2,2-Dichloro-N-[3-[3-(2-cyclopropyl-6-trifluoromethylphenyl)-5-isoxazolyl]phenyl] Acetamide;

Compound 91: 2,2-Dichloro-N-[3-[3-(2-methoxy-6-methylphenyl)-5-isoxazolyl]phenyl] Acetamide;

Compound 93: 2,2-Dichloro-N-[3-[3-(2-isopropyl-6-trifluoromethylphenyl)-5-isoxazolyl]phenyl] Acetamide;

UNITED STATES PATENT AND TRADEMARK OFFICE
CERTIFICATE OF CORRECTION

PATENT NO. : 6,759,538 B2
APPLICATION NO. : 10/286017
DATED : July 6, 2004
INVENTOR(S) : Rajinder Singh et al.

It is certified that error appears in the above-identified patent and that said Letters Patent is hereby corrected as shown below:

Compound 95: 2,2-Dichloro-N-[3-[3-[2-chloro-6-(N-morpholino-2-ethyleneoxy)phenyl]-5-isoxazolyl]-phenyl] Acetamide;

Compound 97: 2,2-Dichloro-N-[3-[3-(2-chloro-6-cyclopentylphenyl)-5-isoxazolyl]phenyl] Acetamide;

Compound 99: 2,2-Dichloro-N-[3-[3-[2-chloro-6-(4-methylpiperazino)phenyl]-5-isoxazolyl]phenyl] Acetamide;

Compound 101: 2-Iodo-N-[3-[3-(2,6-dichlorophenyl)-5-isoxazolyl]phenyl] Acetamide;

Compound 103: 2,2-Dichloro-N-[3-[3-(2-chloro-6-n-butylphenyl)-5-isoxazolyl]phenyl] Acetamide;

Compound 105: 2,2-Dichloro-N-[3-[3-(2-cyclopentyl-6-trifluoromethylphenyl)-5-isoxazolyl]phenyl] Acetamide;

Compound 107: 2,2-Dichloro-N-[3-[3-(2,6-dichlorophenyl)-5-isoxazolyl]-4-(N-morpholinosulfamoyl)-phenyl] Acetamide;

Compound 109: 2,2-Dichloro-N-[3-[3-[2-trifluoromethyl-6-(4-methylpiperazino)phenyl]-5-isoxazolyl]-phenyl] Acetamide;

Compound 111: 2,2-Dichloro-N-[3-[3-(2-chloro-6-cyclohexylphenyl)-5-isoxazolyl]phenyl] Acetamide;

Compound 113: 2,2-Dichloro-N-[3-[3-(2-trifluoromethoxyphenyl)-5-isoxazolyl]phenyl] Acetamide;

Compound 115: 2,2-Dichloro-N-[3-[3-(2-carbomethoxy)phenyl-5-isoxazolyl]phenyl] Acetamide;

Compound 117: 2,2-Dichloro-N-[3-[3-[2-chloro-6-(N-imidazolyl)phenyl]-5-isoxazolyl]phenyl] Acetamide;

Compound 119: 2,2-Dichloro-N-[3-[3-(2-isopropyloxyphenyl)-5-isoxazolyl]phenyl] Acetamide;

Compound 121: 2,2-Dichloro-N-[3-[3-(2,6-diisopropylphenyl)-5-isoxazolyl]phenyl] Acetamide;

Compound 123: 2,2-Dichloro-N-[3-[3-(2-phenyl)phenyl-5-isoxazolyl]phenyl] Acetamide;

Compound 125: 2,2-Dichloro-N-[3-[3-[2,6-dichloro-4-(N-piperidinylethylenoxy)phenyl]-5-isoxazolyl]-phenyl] Acetamide;

Compound 127: 2,2-Dichloro-N-[3-[3-(2,6-dichlorophenyl)-5-isoxazolyl]-4-methoxyphenyl] Acetamide;

Compound 129: 2,2-Dichloro-N-[3-[3-(2-cyclopentylphenyl)-5-isoxazolyl]phenyl] Acetamide;

Compound 131: 2-Dichloro-N-[3-[3-[2-chloro-6-(N,N-dimethylethylene-N'-methylamino)phenyl]-5-isoxazolyl]-phenyl] Acetamide;

UNITED STATES PATENT AND TRADEMARK OFFICE
CERTIFICATE OF CORRECTION

PATENT NO. : 6,759,538 B2
APPLICATION NO. : 10/286017
DATED : July 6, 2004
INVENTOR(S) : Rajinder Singh et al.

It is certified that error appears in the above-identified patent and that said Letters Patent is hereby corrected as shown below:

Compound 132: (±)-2,2-Dichloro-N-[3-[3-[2-chloro-6-(3-dimethylamino-N-pyrrolidino)phenyl]-5-isoxazolyl]-phenyl] Acetamide;
Compound 135: 2,2-Dichloro-N-[3-[3-(3-carbomethoxy-2,6-dichlorophenyl)-5-isoxazolyl]phenyl] Acetamide;
Compound 137: 2,2-Dichloro-N-[3-[3-(2,3,6-trichlorophenyl)-5-isoxazolyl]phenyl] Acetamide;
Compound 139: 2,2-Dichloro-N-[3-[3-(3-carboxy-2,6-dichlorophenyl)-5-isoxazolyl]phenyl] Acetamide;
Compound 141: 2,2-Dichloro-N-[3-[3-(2-chloro-5-trifluoromethylphenyl)-5-isoxazolyl]phenyl] Acetamide;
Compound 143: 2,2-Dichloro-N-[3-[3-[2,4-dichloro-6-(N-morpholino-2-ethyleneoxy)phenyl]-5-isoxazolyl]-phenyl] Acetamide;
Compound 145: 2,2-Difluoro-N-[3-[3-(2,6-dichlorophenyl)-5-isoxazolyl]phenyl] Acetamide;
Compound 149: 2,2-Dichloro-N-[3-[3-(2,6-difluoro-3-methylphenyl)-5-isoxazolyl]phenyl] Acetamide;
Compound 151: 2,2-Dichloro-N-[3-[3-[2-chloro-6-(4-carboethoxypiperidino)phenyl]-5-isoxazolyl]-phenyl] Acetamide;
Compound 153: 2,2-Dichloro-N-[3-[3-(2-fluoro-6-methylsulfonyl)phenyl-5-isoxazolyl]phenyl] Acetamide;
Compound 155: 2,2-Dichloro-N-[3-[3-[2-(N-morpholinomethyl)phenyl]-5-isoxazolyl]phenyl] Acetamide;
Compound 157: 2,2-Dichloro-N-[3-[3-(2-carboxyphenyl)-5-isoxazolyl]phenyl] Acetamide;
Compound 159: 2,2-Dichloro-N-[3-[3-(2,4-dichlorophenyl)-5-isoxazolyl]phenyl] Acetamide;
Compound 161: 2,2-Dichloro-N-[3-[3-(2-benzyloxyphenyl)-5-isoxazolyl]phenyl] Acetamide;
Compound 163: 2,2-Dichloro-N-[3-[3-(2,3-dimethylphenyl-5-isoxazolyl]phenyl] Acetamide;
Compound 165: 2,2-Dichloro-N-[3-[3-(2,6-dichlorophenyl)-5-isoxazolyl]-6-methylphenyl] Acetamide;
Compound 167: 2,2-Dichloro-N-[3-[3-(2,6-dichlorophenyl)-5-isoxazolyl]-2-methylphenyl) Acetamide;
Compound 169: 2,2-Dichloro-N-[3-[3-(2,6-dichlorophenyl)-5-isoxazolyl][6-(N-morpholino)phenyl] Acetamide;
Compound 171: 2,2-Dichloro-N-[3-[3-(2,6-dichlorophenyl)-5-isoxazolyl]-6-(N-morpholino-2-ethyleneoxy)phenyl] Acetamide;

UNITED STATES PATENT AND TRADEMARK OFFICE
CERTIFICATE OF CORRECTION

PATENT NO. : 6,759,538 B2
APPLICATION NO. : 10/286017
DATED : July 6, 2004
INVENTOR(S) : Rajinder Singh et al.

It is certified that error appears in the above-identified patent and that said Letters Patent is hereby corrected as shown below:

Compound 173: 2,2-Dichloro-N-[3-[3-(2,6-dichlorophenyl)-5-isoxazolyl]-6-methoxyphenyl] Acetamide;
    Compound 175: 2,2-Dichloro-N-[3-[3-[2-chloro-6-[4-(N-piperidinyl)-N-piperidinyl]phenyl]-5-isoxazolyl]phenyl] Acetamide;
    Compound 177: 2,2-Dichloro-N-[3-[3-(2-chlorophenyl)-5-isoxazolyl]phenyl] Acetamide;
    Compound 179: 2,2-Dichloro-N-[3-[3-(2-bromophenyl)-5-isoxazolyl]phenyl] Acetamide;
    Compound 181: 2,2-Dichloro-N-[3-[3-(2-chloro-6-nitrophenyl)-5-isoxazolyl] phenyl] Acetamide;
    Compound 183: 2,2-Dichloro-N-[3-[3-(2-methoxyphenyl)-5-isoxazolyl] phenyl] Acetamide;
    Compound 185: 2,2-Dichloro-N-[3-[3-(2-bromo-6-chlorophenyl)-5-isoxazolyl]phenyl] Acetamide; and
    Compound 187: 2,2-Dichloro-N-[3-[3-(2-chloro-6-(4-amino-N-piperidinyl) phenyl]-5-isoxazolyl] phenyl] Acetamide.

Add claim 36 as follows:
    36. The composition of claim 16 in which the compound is 2,2-dichloro-N-[3-[3-(2,6-dichlorophenyl-5-isoxazolylluhenyl] acetamide.

Signed and Sealed this

Twenty-sixth Day of December, 2006

JON W. DUDAS
*Director of the United States Patent and Trademark Office*